(12) United States Patent
Huh et al.

(10) Patent No.: US 11,542,258 B2
(45) Date of Patent: Jan. 3, 2023

(54) HETEROCYCLIC COMPOUND AND ORGANIC LIGHT EMITTING DEVICE COMPRISING THE SAME

(71) Applicant: LG CHEM, LTD., Seoul (KR)

(72) Inventors: Jungoh Huh, Daejeon (KR); Dong Hoon Lee, Daejeon (KR); Boon Jae Jang, Daejeon (KR); Dong Uk Heo, Daejeon (KR); Miyeon Han, Daejeon (KR); Junghoon Yang, Daejeon (KR)

(73) Assignee: LG CHEM, LTD., Seoul (KR)

( * ) Notice: Subject to any disclaimer, the term of this patent is extended or adjusted under 35 U.S.C. 154(b) by 433 days.

(21) Appl. No.: 16/625,589

(22) PCT Filed: May 30, 2018

(86) PCT No.: PCT/KR2018/006166
§ 371 (c)(1),
(2) Date: Dec. 20, 2019

(87) PCT Pub. No.: WO2019/004612
PCT Pub. Date: Jan. 3, 2019

(65) Prior Publication Data
US 2020/0262825 A1 Aug. 20, 2020

(30) Foreign Application Priority Data
Jun. 29, 2017 (KR) .......... 10-2017-0082779
May 25, 2018 (KR) .......... 10-2018-0059817

(51) Int. Cl.
*C07D 409/14* (2006.01)
*C07D 405/04* (2006.01)
(Continued)

(52) U.S. Cl.
CPC ......... *C07D 409/14* (2013.01); *C07D 405/04* (2013.01); *C07D 405/14* (2013.01);
(Continued)

(58) Field of Classification Search
CPC .. C07D 409/14; C07D 405/04; C07D 405/14; C07D 411/14; C07D 413/14;
(Continued)

(56) References Cited

U.S. PATENT DOCUMENTS

2004/0251816 A1  12/2004  Leo et al.
2014/0346483 A1  11/2014  Yu et al.
(Continued)

FOREIGN PATENT DOCUMENTS

CN   101440082   5/2009
CN   102786508   11/2012
(Continued)

OTHER PUBLICATIONS

Computer-generated English-language translation of WO-2018080066-A1.*

*Primary Examiner* — Vu A Nguyen
(74) *Attorney, Agent, or Firm* — Dentons US LLP

(57) ABSTRACT

Provided is a novel heterocyclic compound of Chemical Formula 1:

(Continued)

Chemical Formula 1

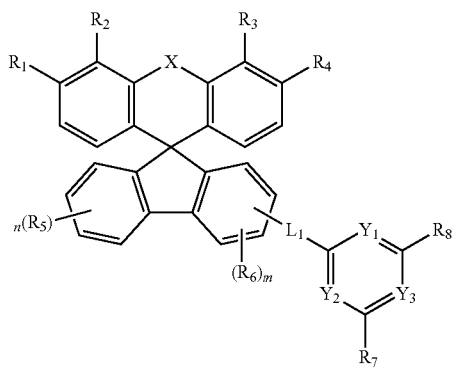

and to an organic light emitting device including the same.

14 Claims, 1 Drawing Sheet

(51) Int. Cl.
C07D 405/14 (2006.01)
C07D 413/14 (2006.01)
C07D 417/14 (2006.01)
C07F 7/08 (2006.01)
H01L 51/00 (2006.01)
H01L 51/50 (2006.01)
C07D 411/14 (2006.01)

(52) U.S. Cl.
CPC .......... C07D 411/14 (2013.01); C07D 413/14 (2013.01); C07D 417/14 (2013.01); C07F 7/0812 (2013.01); H01L 51/0067 (2013.01); *H01L 51/0072* (2013.01); *H01L 51/0073* (2013.01); *H01L 51/0074* (2013.01); *H01L 51/0094* (2013.01); *H01L 51/5072* (2013.01); *H01L 51/5092* (2013.01)

(58) Field of Classification Search
CPC .............. C07D 417/14; H01L 51/0067; H01L 51/0072; H01L 51/0073; H01L 51/0074; H01L 51/0094; H01L 51/5072; H01L 51/5092; C07F 7/0812
See application file for complete search history.

(56) References Cited

U.S. PATENT DOCUMENTS

| | | | |
|---|---|---|---|
| 2015/0115241 A1 | 4/2015 | Zoellner et al. | |
| 2015/0295181 A1 | 10/2015 | Mujica-Fernaud et al. | |
| 2017/0222157 A1* | 8/2017 | Jatsch | C07D 235/18 |

FOREIGN PATENT DOCUMENTS

| | | | |
|---|---|---|---|
| CN | 104263351 | 1/2015 | |
| JP | 2009191232 | 8/2009 | |
| JP | 4843889 | 12/2011 | |
| JP | 5416906 | 2/2014 | |
| KR | 10-20130073537 | 7/2013 | |
| KR | 10-1593368 | 2/2016 | |
| KR | 1593368 B1 * | 2/2016 | |
| KR | 10-20170032414 | 3/2017 | |
| KR | 10-1742436 | 5/2017 | |
| KR | 1742436 B1 * | 5/2017 | |
| KR | 10-20180046150 | 5/2018 | |
| WO | 2003012890 | 2/2003 | |
| WO | 2014072017 | 5/2014 | |
| WO | 2016012075 | 1/2016 | |
| WO | 2017105041 | 6/2017 | |
| WO | WO-2018080066 A1 * | 5/2018 | C07D 209/82 |

* cited by examiner

【FIG. 1】
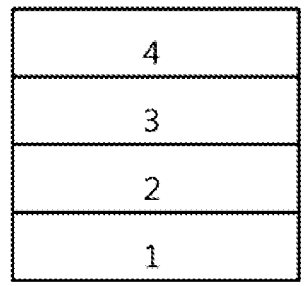
【FIG. 2】
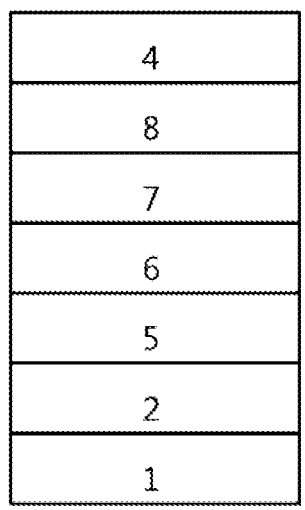
【FIG. 3】
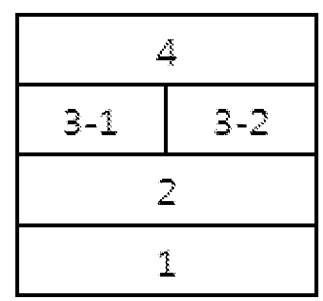

HETEROCYCLIC COMPOUND AND ORGANIC LIGHT EMITTING DEVICE COMPRISING THE SAME

CROSS-REFERENCE TO RELATED APPLICATION(S)

This application is a National Stage Application of International Application No. PCT/KR2018/006166, filed on May 30, 2018, which claims priority to and the benefit of the filing dates of Korean Patent Application No. 10-2017-0082779 filed with Korean Intellectual Property Office on Jun. 29, 2017, and Korean Patent Application No. 10-2018-0059817 filed with Korean Intellectual Property Office on May 25, 2018, the entire contents of which are incorporated herein by reference.

TECHNICAL FIELD

The present invention relates to a novel heterocyclic compound and to an organic light emitting device comprising the same.

BACKGROUND

In general, an organic light emitting phenomenon refers to a phenomenon where electric energy is converted into light energy by using an organic material. The organic light emitting device using the organic light emitting phenomenon has characteristics such as a wide viewing angle, an excellent contrast, a fast response time, an excellent luminance, driving voltage and response speed, and thus many studies have proceeded.

The organic light emitting device generally has a structure which comprises an anode, a cathode, and an organic material layer interposed between the anode and the cathode. The organic material layer frequently has a multilayered structure that comprises different materials in order to enhance efficiency and stability of the organic light emitting device, and for example, the organic material layer can be formed of a hole injection layer, a hole transport layer, a light emitting layer, an electron transport layer, an electron injection layer and the like. In the structure of the organic light emitting device, if a voltage is applied between two electrodes, the holes are injected from an anode into the organic material layer and the electrons are injected from the cathode into the organic material layer, and when the injected holes and electrons meet each other, an exciton is formed, and light is emitted when the exciton falls to a ground state again.

There is a continuing need for the development of new materials for the organic materials used in these organic light emitting devices.

PRIOR ART LITERATURE

Patent Literature (Patent Literature 0001) Korean Patent Laid-open Publication No. 10-2013-073537

SUMMARY OF THE INVENTION

It is an object of the present invention to provide a novel heterocyclic compound and an organic light emitting device including the same.

In one aspect of the invention, there is provided a compound of Chemical Formula 1:

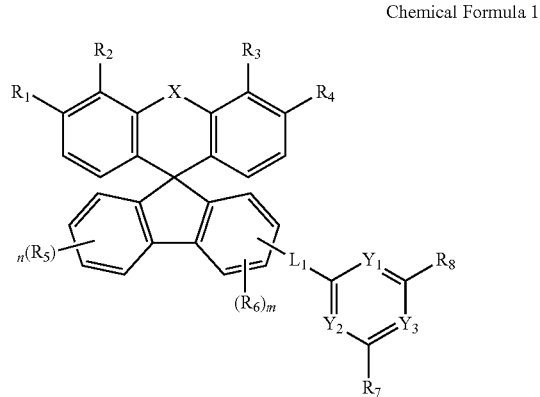

Chemical Formula 1 wherein, in Chemical Formula 1:

X is O or S;

$Y_1$, $Y_2$ and $Y_3$ are each independently N or CR', with the proviso that at least two of them are N;

R' is hydrogen, or can be connected with adjacent $R_6$ and $R_7$ to form a substituted or unsubstituted $C_{6-60}$ aryl;

$R_1$, $R_2$, $R_3$ and $R_4$ can be each independently hydrogen, deuterium, a substituted or unsubstituted $C_{1-60}$ alkyl, or a substituted or unsubstituted $C_{6-60}$ aryl, or they can be combined with adjacent substituents to form a substituted or unsubstituted benzene ring;

$R_5$ and $R_6$ are each independently hydrogen, deuterium, a substituted or unsubstituted $C_{1-60}$ alkyl, or a substituted or unsubstituted $C_{6-60}$ aryl;

n is an integer of 1 to 4;

m is an integer of 1 to 3;

$L_1$ is a direct bond, a substituted or unsubstituted $C_{6-60}$ arylene, or a substituted or unsubstituted $C_{5-60}$ heteroarylene containing one or more heteroatoms selected from the group consisting of N, O and S; and $R_7$ and $R_8$ are each independently a substituted or unsubstituted $C_{6-60}$ aryl, a substituted or unsubstituted silyl, or a substituted or unsubstituted $C_{5-60}$ heteroaryl containing one or more heteroatoms selected from the group consisting of N, O, S and Si, with the proviso that at least one of $R_7$ and $R_8$ is a compound of Chemical Formula 2:

Chemical Formula 2 wherein, in Chemical Formula 2:

$L_2$ is a direct bond, a substituted or unsubstituted $C_{6-60}$ arylene, or a substituted or unsubstituted $C_{5-60}$ heteroarylene containing one or more heteroatoms selected from the group consisting of N, O and S; and Het is a silyl unsubstituted or substituted with at least one $C_{1-60}$ alkyl or $C_{6-60}$ aryl, a $C_{6-60}$ aryl substituted with at least one —CN or —$CF_3$, or a substituted or unsubstituted $C_{5-60}$ heteroaryl containing one or more heteroatoms selected from the group consisting of N, O, S and Si.

In another aspect of the invention, there is provided an organic light emitting device including a first electrode; a second electrode provided opposite to the first electrode; and one or more organic material layers provided between the first electrode and the second electrode, wherein one or more layers of the organic material layers include the compound of the present invention described above.

The compound of Chemical Formula 1 described above can be used as a material of an organic material layer of an organic light emitting device and can improve the efficiency, achieve low driving voltage and/or improve lifetime characteristics in the organic light emitting device. In particular, the compound of Chemical Formula 1 can be used as a hole injection material, hole transport material, hole injection and transport material, light emitting material, electron transport material, or electron injection material.

BRIEF DESCRIPTION OF THE DRAWINGS

FIGS. 1 and 3 show an example of an organic light emitting device comprising a substrate 1, an anode 2, a light emitting layer 3, and a cathode 4.

FIG. 2 shows an example of an organic light emitting device comprising a substrate 1, an anode 2, a hole injection layer 5, a hole transport layer 6, a light emitting layer 7, an electron transport layer 8 and a cathode 4.

DETAILED DESCRIPTION OF THE EMBODIMENTS

Hereinafter, embodiments of the present invention will be described in more detail to help understanding of the invention.

In one embodiment of the invention, there is provided a compound of Chemical Formula 1:

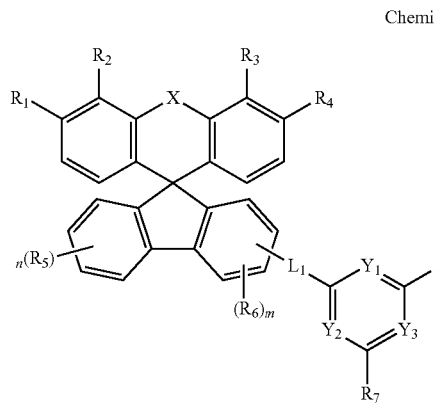

Chemical Formula 1 wherein, in Chemical Formula 1:

X is O or S;

$Y_1$, $Y_2$ and $Y_3$ are each independently N or CR', with the proviso that at least two of them are N, R' is hydrogen, or can be combined with adjacent $R_7$ and $R_8$ to form a substituted or unsubstituted $C_{6-60}$ aryl;

$R_1$, $R_2$, $R_3$, and $R_4$ can be each independently hydrogen, deuterium, a substituted or unsubstituted $C_{1-60}$ alkyl, or a substituted or unsubstituted $C_{6-60}$ aryl, or they can be combined with adjacent substituents to form a substituted or unsubstituted benzene ring;

$R_5$ and $R_6$ are each independently hydrogen, deuterium, a substituted or unsubstituted $C_{1-60}$ alkyl, or a substituted or unsubstituted $C_{6-60}$ aryl;

n is an integer of 1 to 4;

m is an integer of 1 to 3; $L_1$ is a direct bond, a substituted or unsubstituted $C_{6-60}$ arylene, or a substituted or unsubstituted $C_{5-60}$ heteroarylene containing one or more heteroatoms selected from the group consisting of N, O and S; and $R_7$ and $R_8$ are each independently a substituted or unsubstituted $C_{6-60}$ aryl, a substituted or unsubstituted silyl, or a substituted or unsubstituted $C_{5-60}$ heteroaryl containing one or more heteroatoms selected from the group consisting of N, O, S and Si, with the proviso that at least one of $R_7$ and $R_8$ is a compound of Chemical Formula 2:

\*-($L_2$-Het)    Chemical Formula 2 wherein, in Chemical Formula 2:

$L_2$ is a direct bond, a substituted or unsubstituted $C_{6-60}$ arylene, or a substituted or unsubstituted $C_{5-60}$ heteroarylene containing one or more heteroatoms selected from the group consisting of N, O and S; and Het is a silyl unsubstituted or substituted with at least one $C_{1-60}$ alkyl or $C_{6-60}$ aryl, a $C_{6-60}$ aryl substituted with at least one —CN or —CF$_3$, or a substituted or unsubstituted $C_{5-60}$ heteroaryl containing one or more heteroatoms selected from the group consisting of N, O, S and Si.

As used herein, the notation ⁓ and ⎮ mean a bond linked to another substituent group.

As used herein, the term "substituted or unsubstituted" means being unsubstituted or substituted with one or more substituents selected from the group consisting of deuterium, a halogen group, a nitrile group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, or a heterocyclic group containing at least one of N, O and S atoms, or being unsubstituted or substituted with a substituent to which two or more substituents are linked among the substituents exemplified above. For example, "the substituent to which two or more substituents are linked" can be a biphenyl group. That is, the biphenyl group can also be an aryl group and can be interpreted as a substituent to which two phenyl groups are linked.

In the present specification, the number of carbon atoms of a carbonyl group is not particularly limited, but is preferably 1 to 40. Specifically, the carbonyl group can be a compound having the following structural formulae but is not limited thereto:

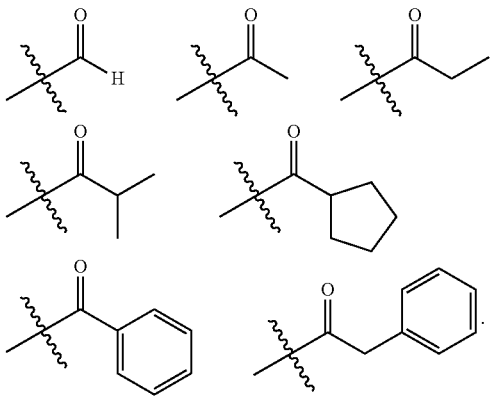

In the present specification, an ester group can have a structure in which oxygen of the ester group can be substituted by a straight-chain, branched-chain, or cyclic alkyl group having 1 to 25 carbon atoms, or an aryl group having 6 to 25 carbon atoms. Specifically, the ester group can be a compound having the following structural formulae, but is not limited thereto:

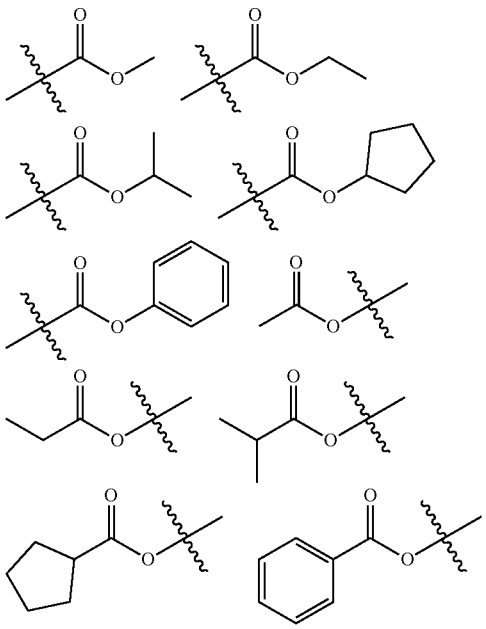

In the present specification, the number of carbon atoms of an imide group is not particularly limited, but is preferably 1 to 25. Specifically, the imide group can be a compound having the following structural formulae, but is not limited thereto:

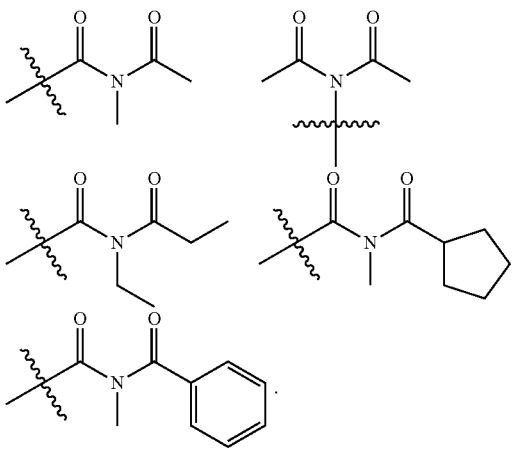

In the present specification, a silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but is not limited thereto.

In the present specification, a boron group specifically includes a trimethylboron group, a triethylboron group, a t-butyldimethylboron group, a triphenylboron group, and a phenylboron group, but is not limited thereto.

In the present specification, examples of a halogen group include fluorine, chlorine, bromine, or iodine.

In the present specification, the alkyl group can be a straight-chain or branched chain, and the number of carbon atoms thereof is not particularly limited, but is preferably 1 to 40. According to one embodiment, the number of carbon atoms of the alkyl group is 1 to 20. According to another embodiment, the number of carbon atoms of the alkyl group is 1 to 10. According to another embodiment, the number of carbon atoms of the alkyl group is 1 to 6. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentyl-methyl, cyclohectyl-methyl, octyl, n-octyl, tert-octyl, 1-methylheptyl, 2-ethylhexyl, 2-propylpentyl, n-nonyl, 2,2-dimethyl-heptyl, 1-ethyl-propyl, 1,1-dimethyl-propyl, isohexyl, 2-methylpentyl, 4-methylhexyl, 5-methylhexyl, and the like, but are not limited thereto.

In the present specification, the alkenyl group can be a straight chain or branched chain, and the number of carbon atoms thereof is not particularly limited, but is preferably 2 to 40. According to one embodiment, the number of carbon atoms of the alkenyl group is 2 to 20. According to another embodiment, the number of carbon atoms of the alkenyl group is 2 to 10. According to still another embodiment, the number of carbon atoms of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenyl-vinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, a cycloalkyl group is not particularly limited, but the number of carbon atoms thereof is preferably 3 to 60. According to one embodiment, the number of carbon atoms of the cycloalkyl group is 3 to 30. According to another embodiment, the number of carbon atoms of the cycloalkyl group is 3 to 20. According to still another embodiment, the number of carbon atoms of the cycloalkyl group is 3 to 6. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, an aryl group is not particularly limited, but preferably has 6 to 60 carbon atoms, and can be a monocyclic aryl group or a polycyclic aryl group. According to one embodiment, the number of carbon atoms of the aryl group is 6 to 30. According to one embodiment, the number of carbon atoms of the aryl group is 6 to 20. The aryl group can be a phenyl group, a biphenyl group, a terphenyl group or the like as the monocyclic aryl group, but is not limited thereto. Examples of the polycyclic aryl group include a naphthyl group, an anthracenyl group, a phenanthryl group, a pyrenyl group, a perylenyl group, a chrysenyl group, a fluorenyl group or the like, but is not limited thereto.

In the present specification, a fluorenyl group can be substituted, and two substituent groups can be connected with each other to form a spiro structure. In the case where the fluorenyl group is substituted,

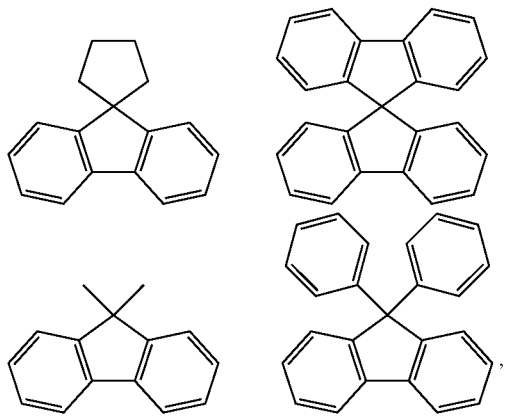

and the like can be formed. However, the structure is not limited thereto.

In the present specification, a heterocyclic group is a heterocyclic group including one or more of O, N, Si, and S as a heteroatom, and the number of carbon atoms thereof is not particularly limited, but is preferably 2 to 60. Examples of the heterocyclic group include a thiophene group, a furan group, a pyrrole group, an imidazole group, a thiazole group, an oxazol group, an oxadiazol group, a triazol group, a pyridyl group, a bipyridyl group, a pyrimidyl group, a triazine group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazol group, a benzocarbazole group, a benzothiophene group, a dibenzothiophene group, a benzofuranyl group, a phenanthroline group, a thiazolyl group, an isoxazolyl group, an oxadiazolyl group, an thiadiazolyl group, a benzothiazolyl group, a phenothiazinyl group, a dibenzofuranyl group, and the like, but are not limited thereto.

In the present specification, the aryl group in the aralkyl group, the aralkenyl group, the alkylaryl group, and the arylamine group is the same as the aforementioned examples of the aryl group. In the present specification, the alkyl group in the aralkyl group, the alkylaryl group and the alkylamine group is the same as the aforementioned examples of the alkyl group. In the present specification, the heteroaryl in the heteroarylamine can be applied to the aforementioned description of the heteroaryl. In the present specification, the alkenyl group in the aralkenyl group is the same as the aforementioned examples of the alkenyl group. In the present specification, the aforementioned description of the aryl group can be applied except that the arylene is a divalent group. In the present specification, the aforementioned description of the heteroaryl can be applied except that the heteroarylene is a divalent group. In the present specification, the aforementioned description of the aryl group or cycloalkyl group can be applied except that the hydrocarbon ring is not a monovalent group but formed by combining two substituent groups. In the present specification, the aforementioned description of the heteroaryl can be applied, except that the heterocycle is not a monovalent group but formed by combining two substituent groups.

Preferably, the compound of Chemical Formula 1 can be any one compound selected from compounds of the following Chemical Formulas 3 to 9:

[Chemical Formula 3]

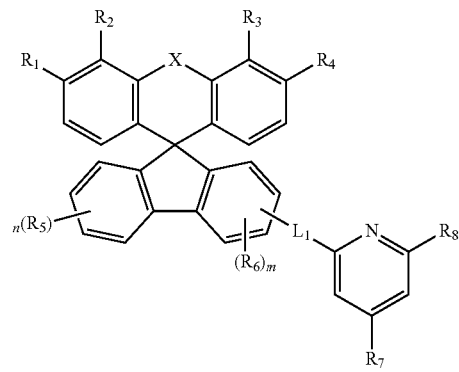

[Chemical Formula 4]

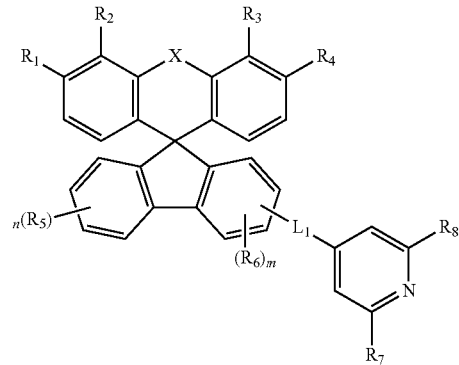

[Chemical Formula 5]

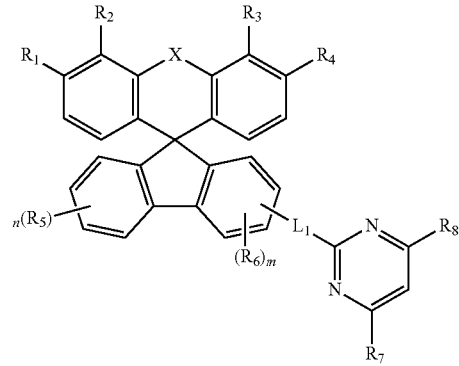

[Chemical Formula 6]

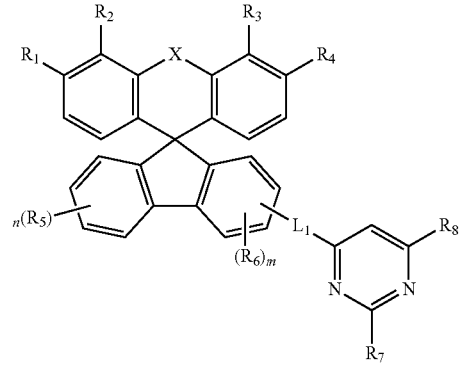

-continued

[Chemical Formula 7]

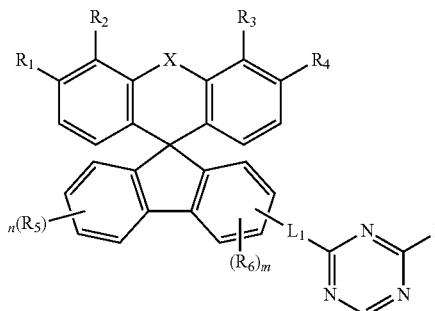

[Chemical Formula 8]

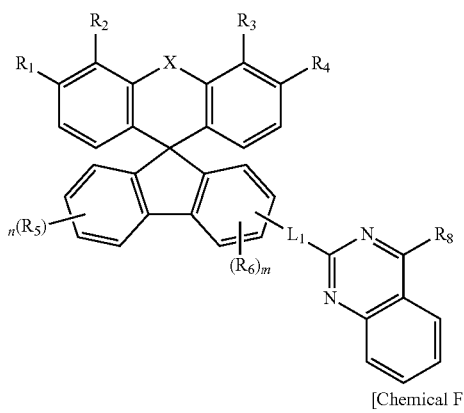

[Chemical Formula 9]

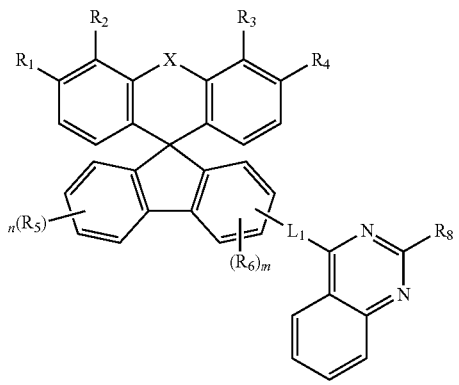

wherein, in Chemical Formulae 2 to 9:

X, $L_1$, $R_1$, $R_2$, $R_3$, $R_4$, $R_5$, $R_6$, $R_7$, $R_8$, n and m are as defined above, with the proviso that in Formulas 8 and 9, $R_8$ is a substituent of Chemical Formula 2:

*-($L_2$-Het)   Chemical Formula 2 wherein, in Chemical Formula 2:

$L_2$ is a direct bond, a substituted or unsubstituted $C_{6-60}$ arylene, or a substituted or unsubstituted $C_{5-60}$ heteroarylene containing one or more heteroatoms selected from the group consisting of N, O and S; and Het is a silyl unsubstituted or substituted with at least one $C_{1-60}$ alkyl or $C_{6-60}$ aryl, a $C_{6-60}$ aryl substituted with at least one —CN or —$CF_3$, or a substituted or unsubstituted $C_{5-60}$ heteroaryl containing one or more heteroatoms selected from the group consisting of N, O, S and Si.

Preferably, the compound of Chemical Formula 1 can be any one selected from compounds of the following Chemical Formulas 10 to 12:

[Chemical Formula 10]

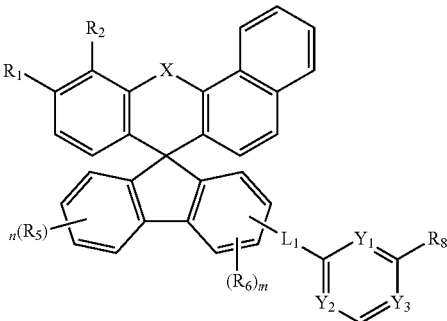

[Chemical Formula 11]

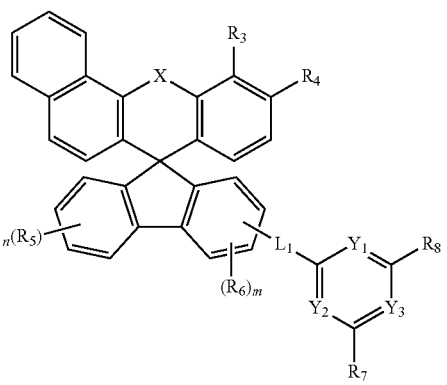

[Chemical Formula 12]

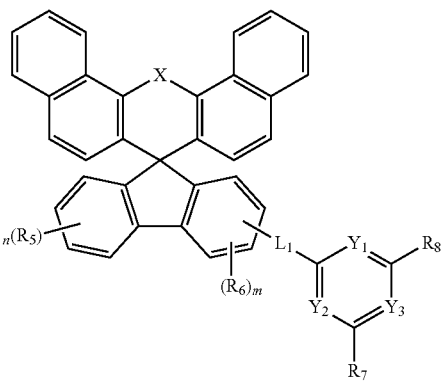

wherein, in Chemical Formulae 10 to 12:

X, $L_1$, $R_1$, $R_2$, $R_3$, $R_4$, $R_5$, $R_6$, $R_7$, $R_8$, n and m are as defined above;

$R_1$ and $R_2$ in Chemical Formula 10, and $R_3$ and $R_4$ in Chemical Formula 11 exclude cases where they are combined with an adjacent substituent to form a substituted or unsubstituted benzene ring, or in other words $R_1$ and $R_2$ in Chemical Formula 10, and $R_3$ and $R_4$ in Chemical Formula 11 do not combine with an adjacent substituent to form a substituted or unsubstituted benzene ring.

Preferably, the Het can be any one selected from compounds of the following Chemical Formulas [1-1] to [1-31]:
[1-1]
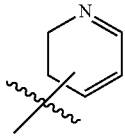
[1-2]
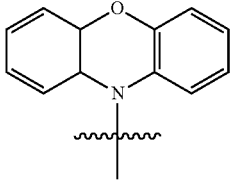
[1-3]
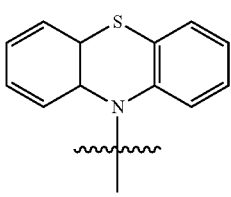
[1-4]
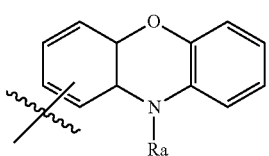
[1-5]
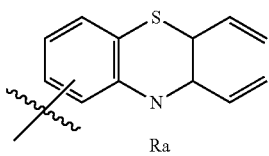
[1-6]
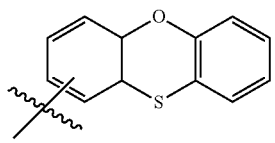
[1-7]
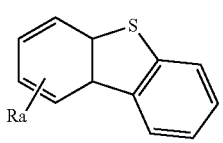
[1-8]
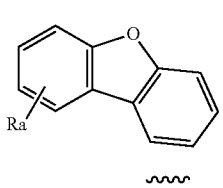
[1-9]
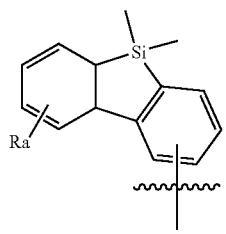
[1-10]
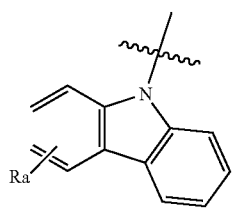
[1-11]
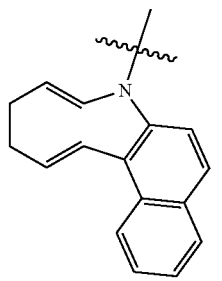
[1-12]
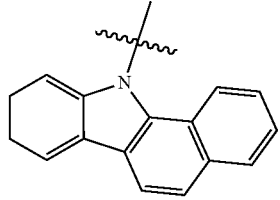
[1-13]
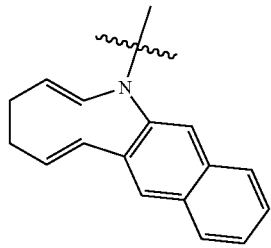
[1-14]
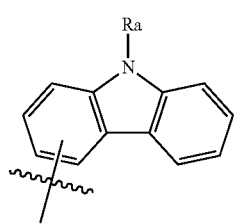

[1-15]
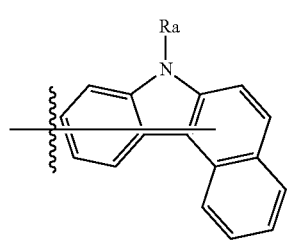
[1-16]
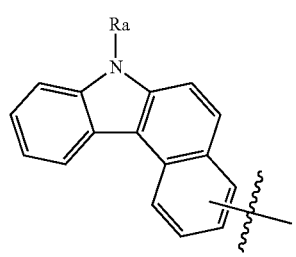
[1-17]
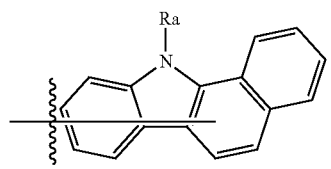
[1-18]
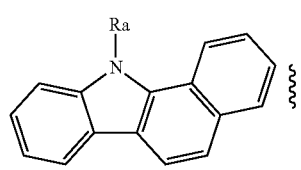
[1-19]
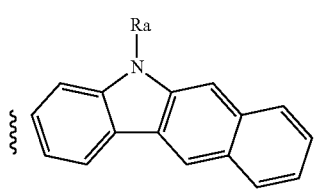
[1-20]
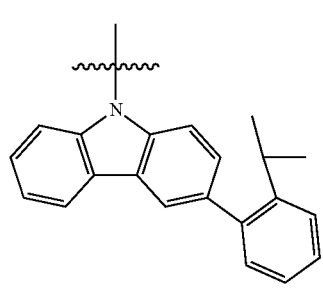
[1-21]
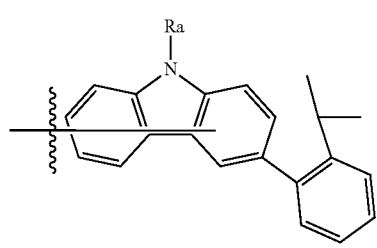
[1-22]
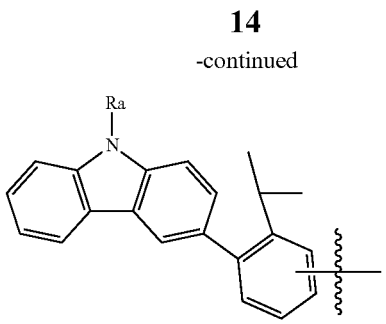
[1-23]
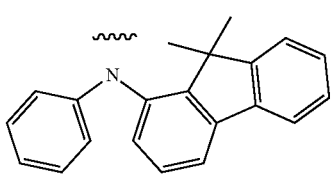
[1-24]
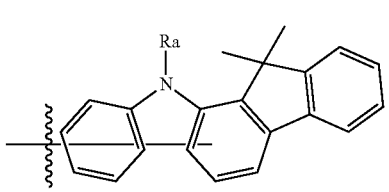
[1-25]
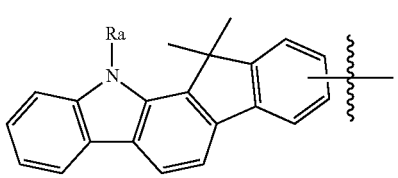
[1-26]
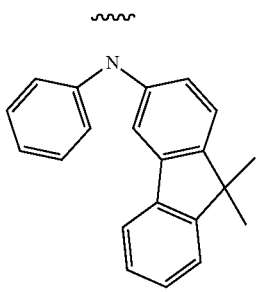
[1-27]
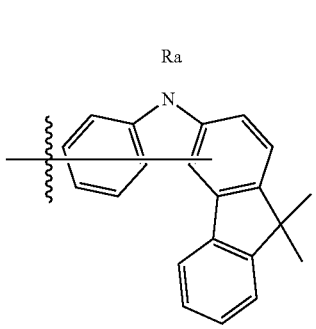

[1-28]

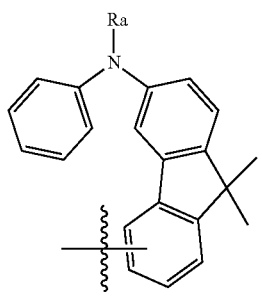

[1-29]

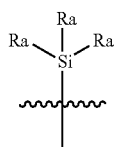

[1-30]

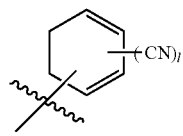

[1-31]

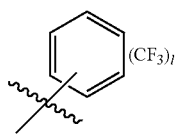

wherein, in Chemical Formulae [1-1] to [1-31]:

each Ra is independently hydrogen, a substituted or unsubstituted $C_{1-60}$ alkyl, or a substituted or unsubstituted $C_{6-60}$ aryl, and each l is independently an integer of 1 to 4.

Preferably, $R_1$, $R_2$, $R_3$ and $R_4$ can be each independently hydrogen, a methyl group, an ethyl group, a propyl group,

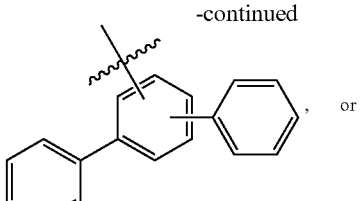

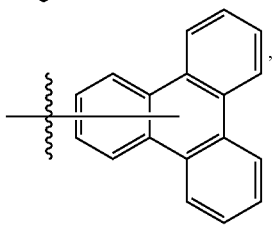

or, or they can be combined with adjacent substituents to form a benzene ring.

Preferably, $R_5$ and $R_6$ can be each independently hydrogen, methyl, ethyl, propyl,

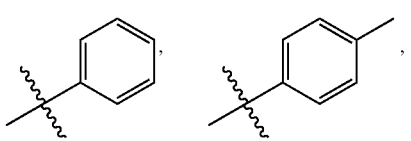

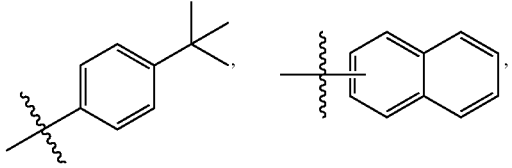

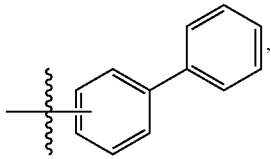

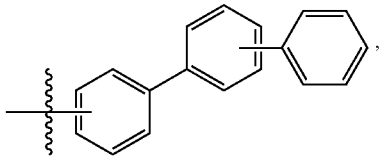

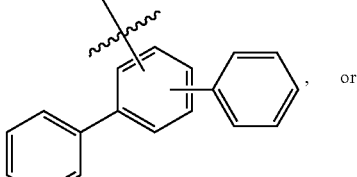

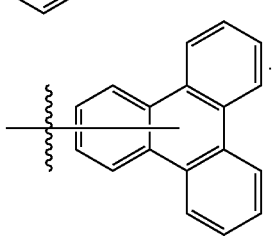

Preferably, n is 1 or 2, and m can be 0 or 1.

Preferably, $L_1$ and $L_2$ can be each independently a direct bond or any one selected from the group consisting of the following:
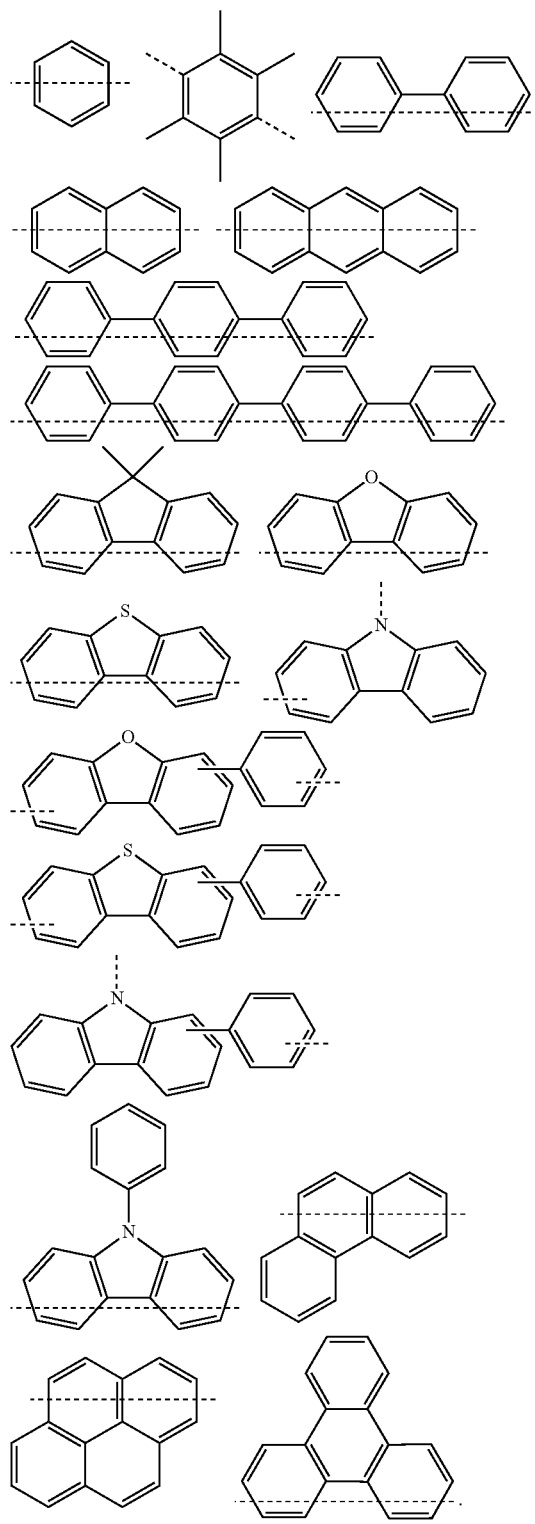
Preferably, the compound of Chemical Formula 1 can be any one selected from the group consisting of the following compounds:
Formula 1-A-1
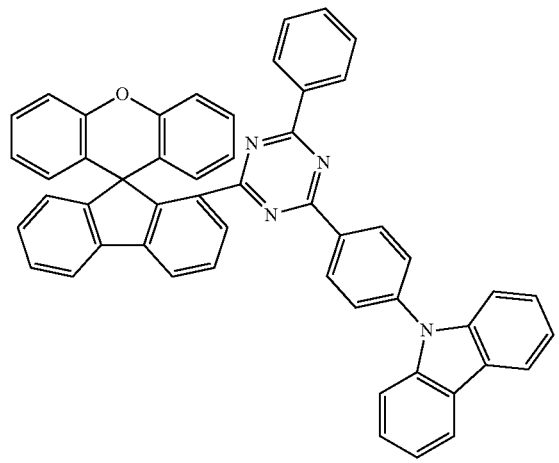
Formula 1-A-2
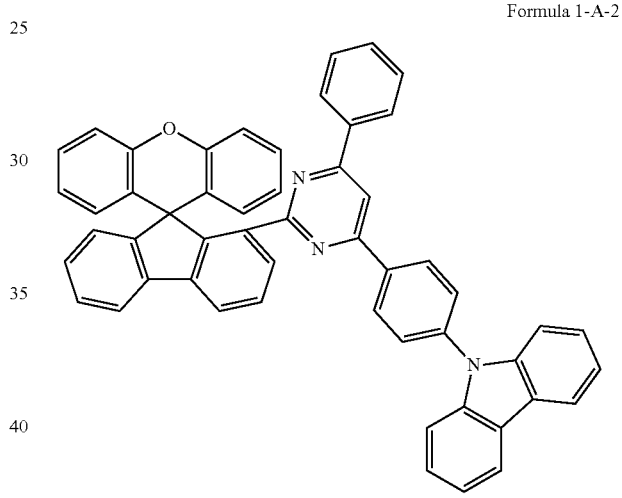
Formula 1-A-3
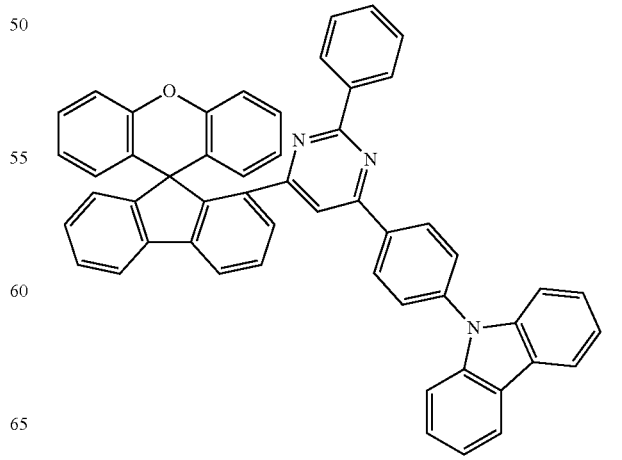

Formula 1-A-4
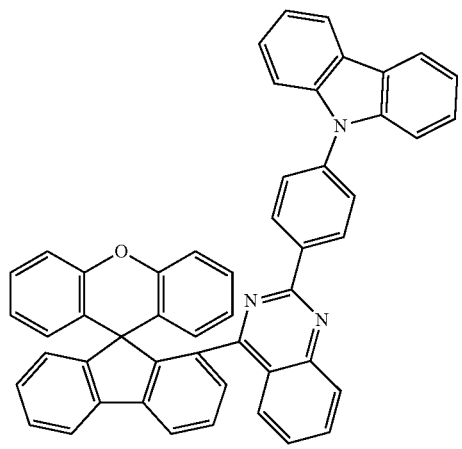
Formula 1-A-5
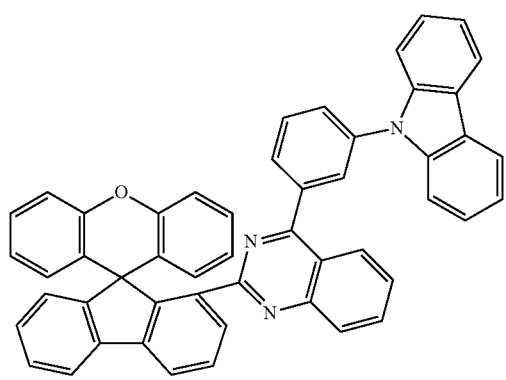
Formula 1-A-6
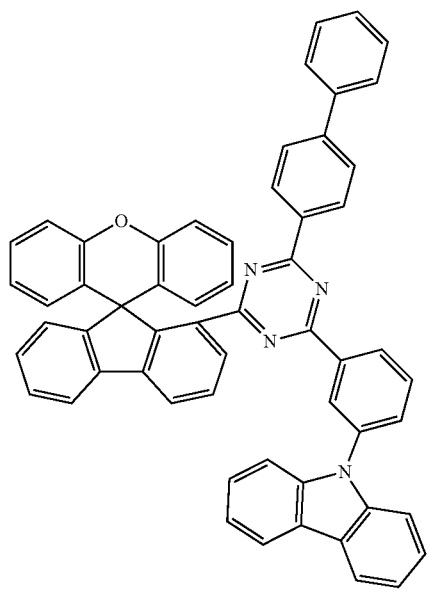
Formula 1-A-7
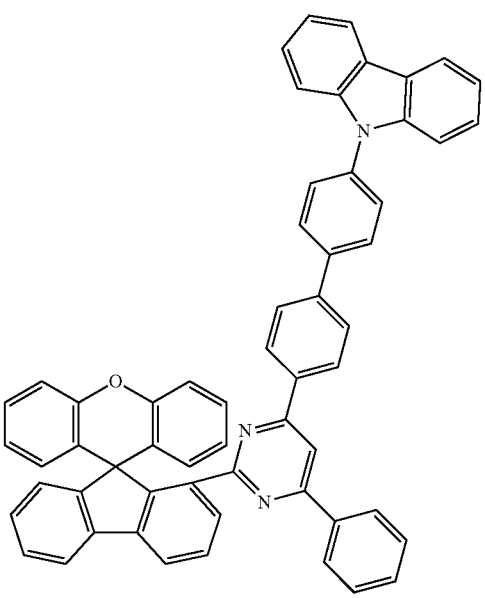
Formula 1-A-8
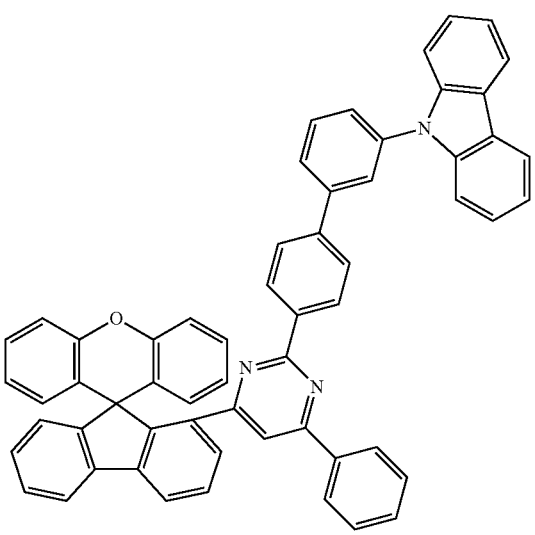

Formula 1-A-9
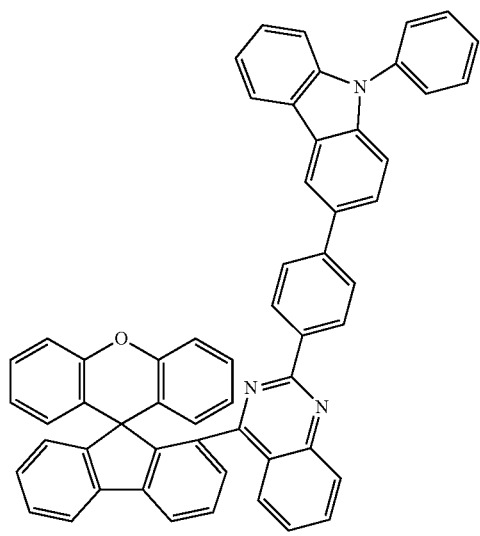
Formula 1-A-10
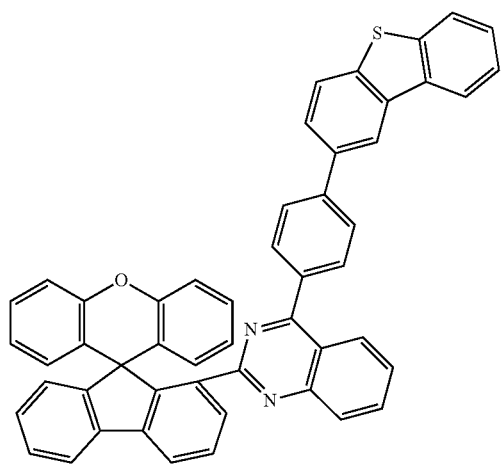
Formula 1-A-11
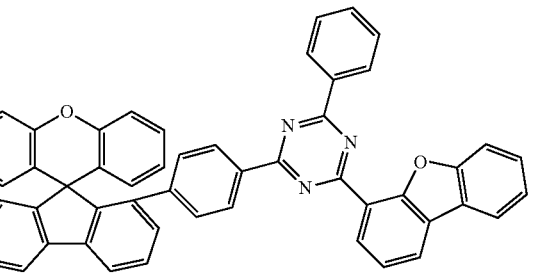
Formula 1-A-12
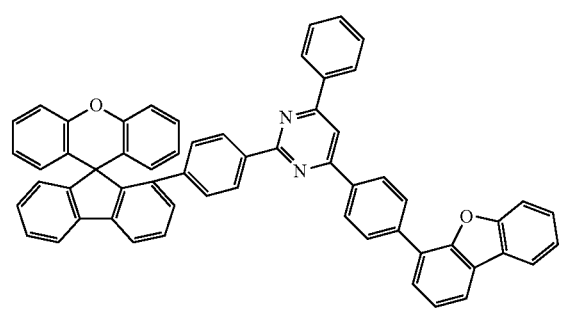
Formula 1-A-13
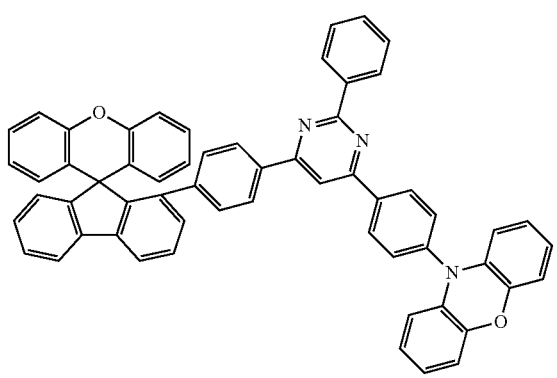
Formula 1-A-14
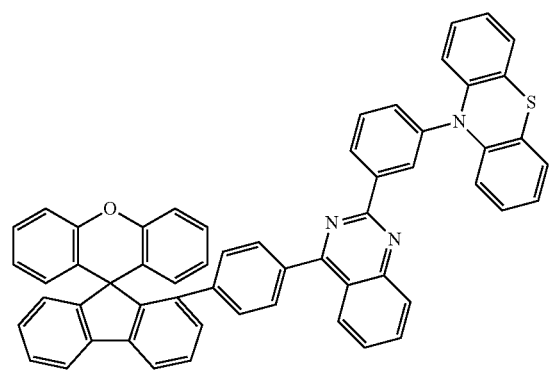
Formula 1-A-15
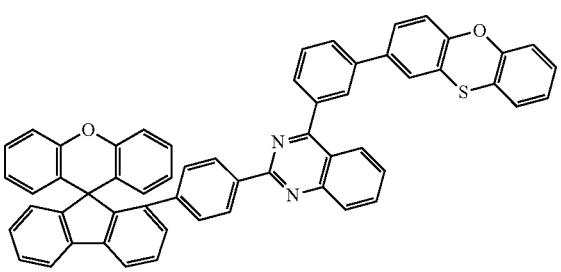
Formula 1-A-16
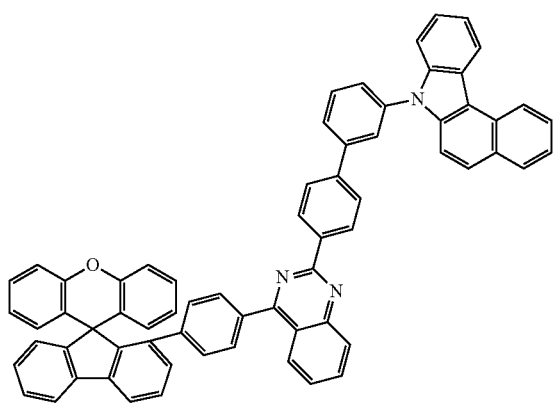

Formula 1-A-17
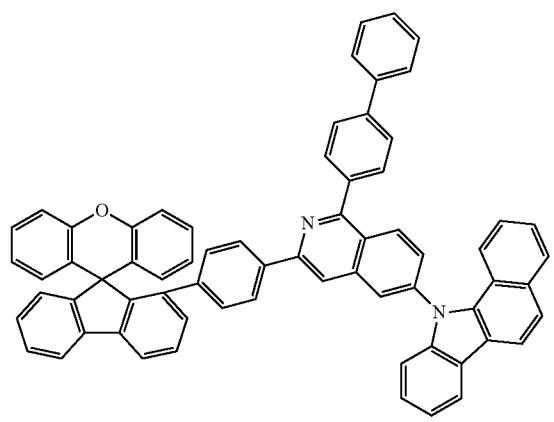
Formula 1-A-18
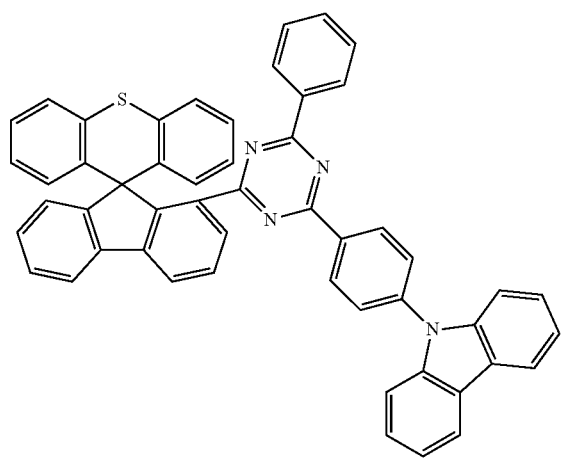
Formula 1-A-19
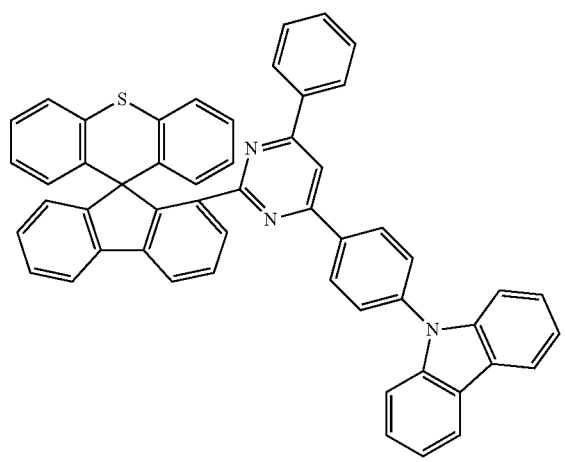
Formula 1-A-20
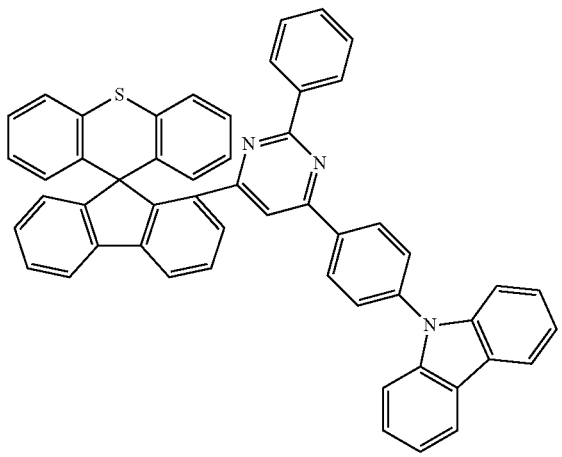
Formula 1-A-21
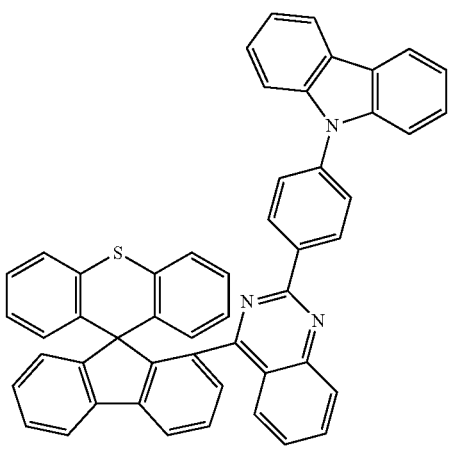
Formula 1-A-22
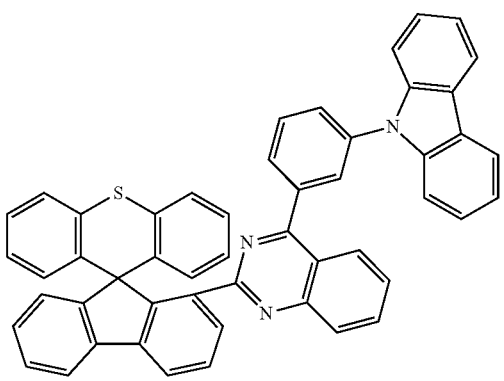

Formula 1-A-23
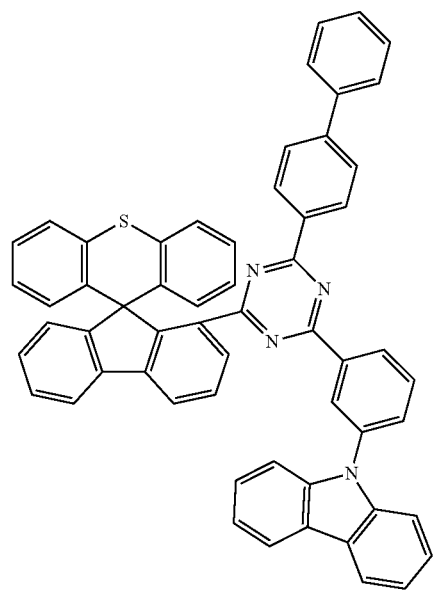
Formula 1-A-24
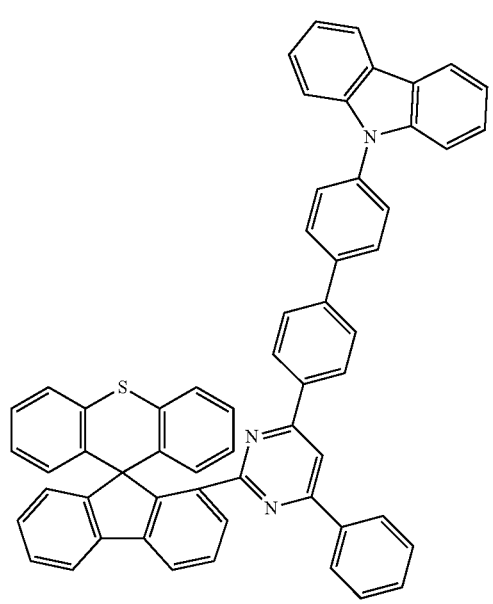
Formula 1-A-25
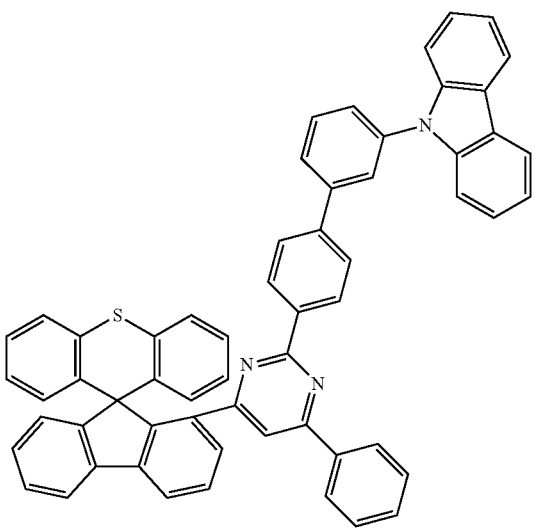
Formula 1-A-26
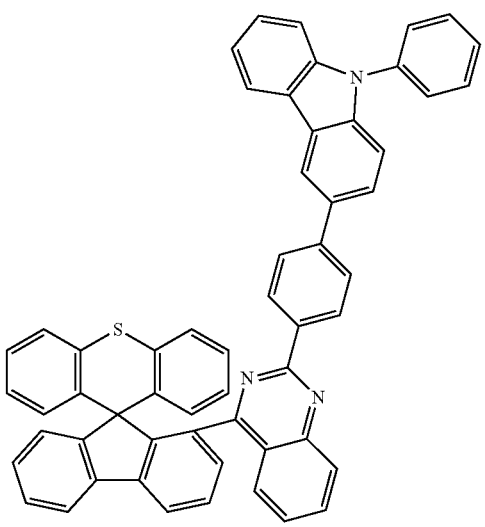
Formula 1-A-27
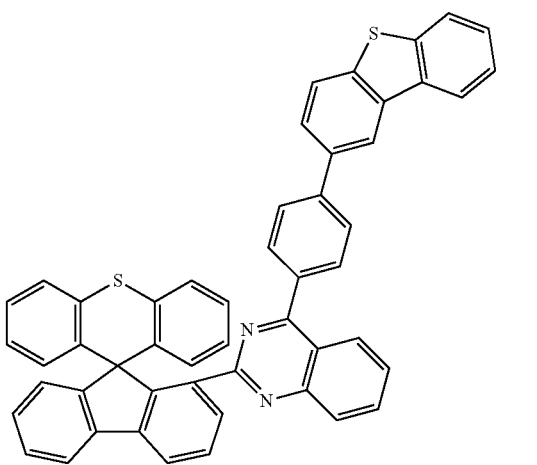

Formula 1-A-28
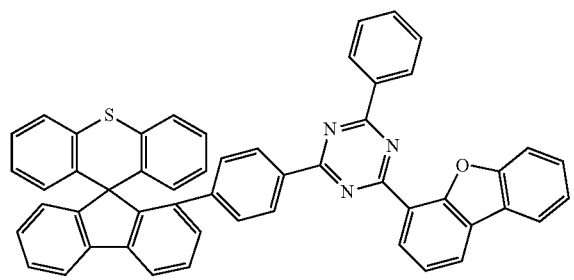
Formula 1-A-29
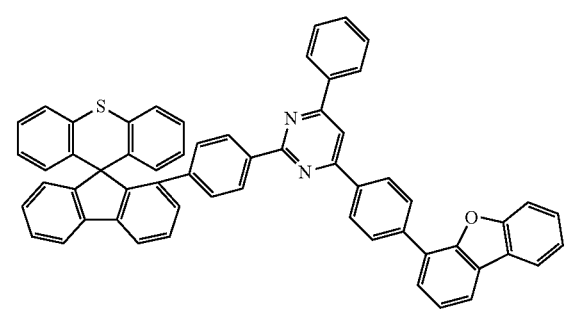
Formula 1-A-30
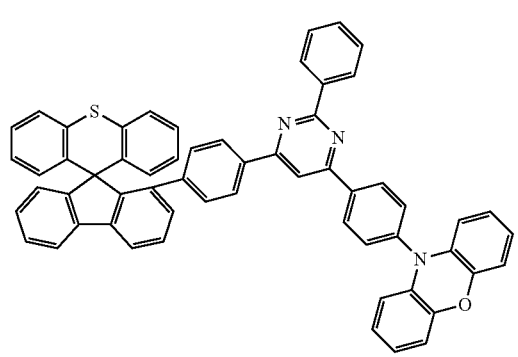
Formula 1-A-31
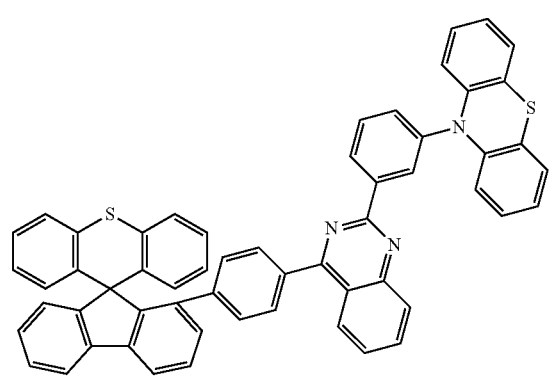
Formula 1-A-32
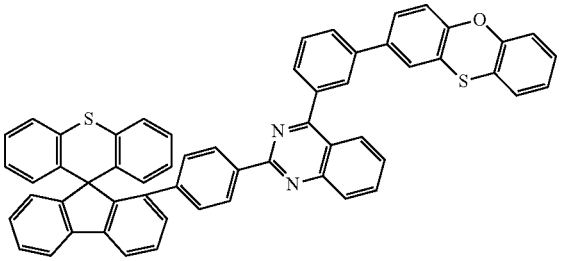
Formula 1-A-33
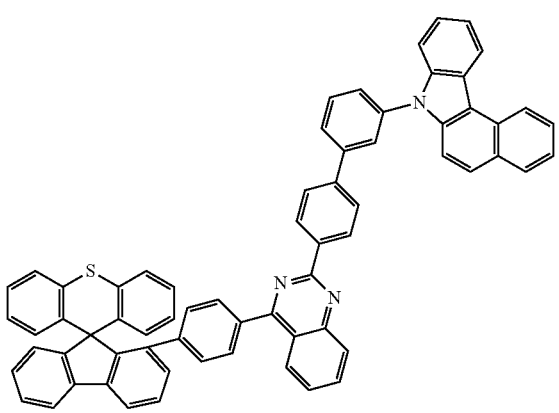
Formula 1-A-34
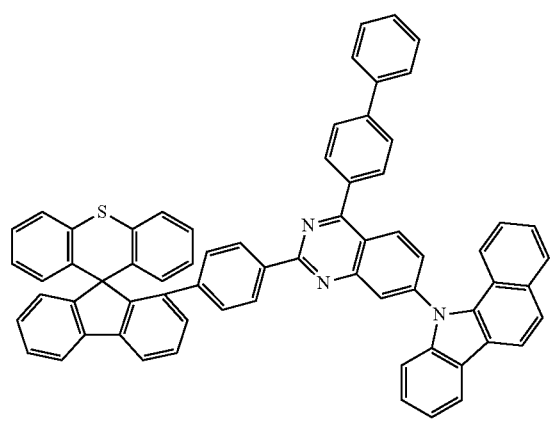
Formula 1-A-35
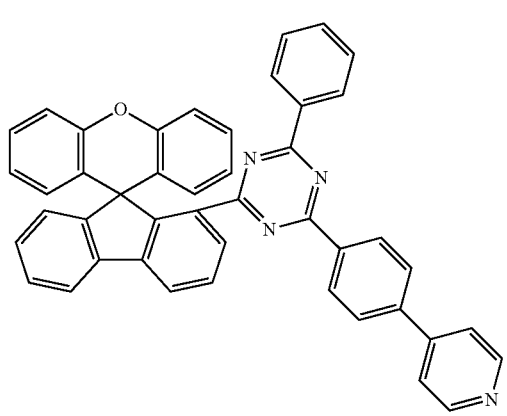

-continued
Formula 1-A-36
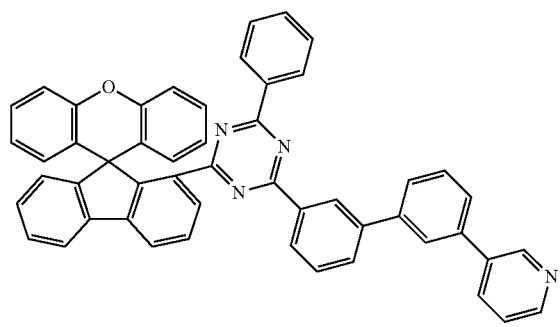
Formula 1-A-37
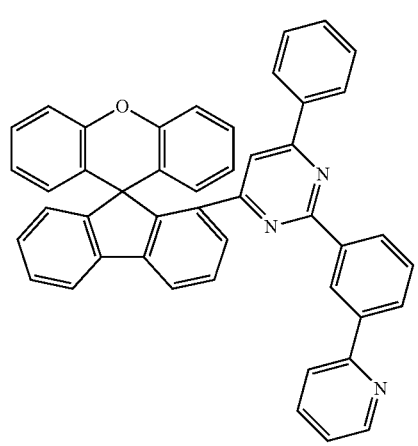
Formula 1-A-38
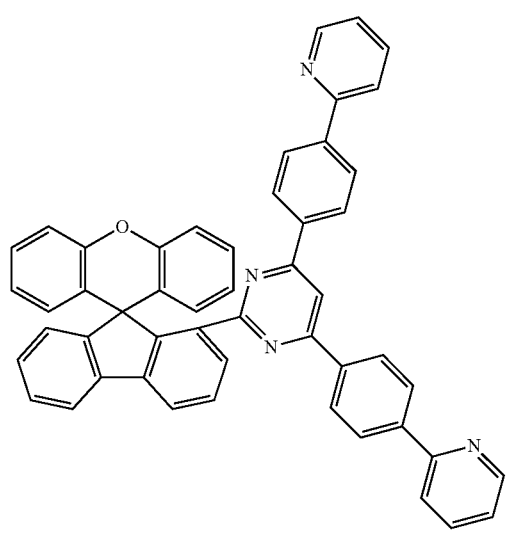
-continued
Formula 1-B-1
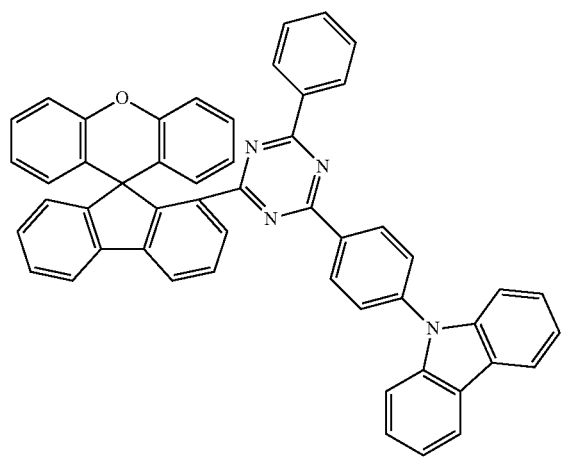
Formula 1-B-2
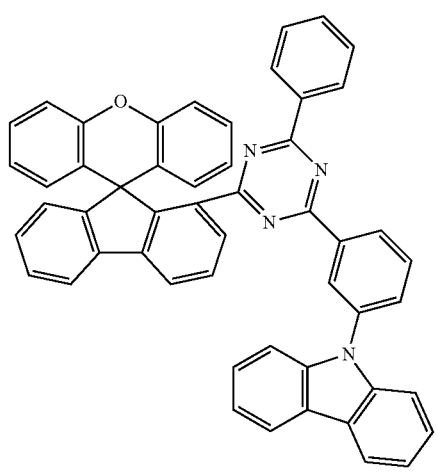
Formula 1-B-3
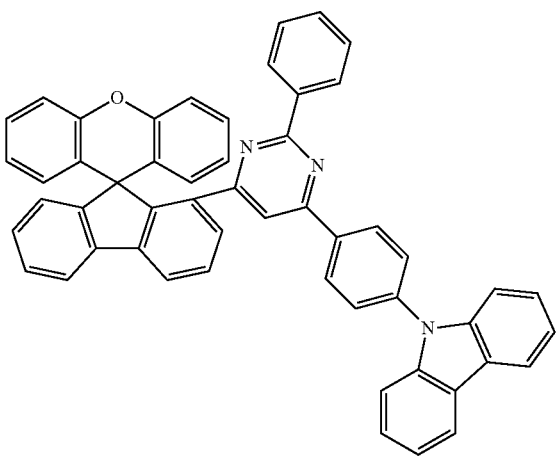

-continued
Formula 1-B-4
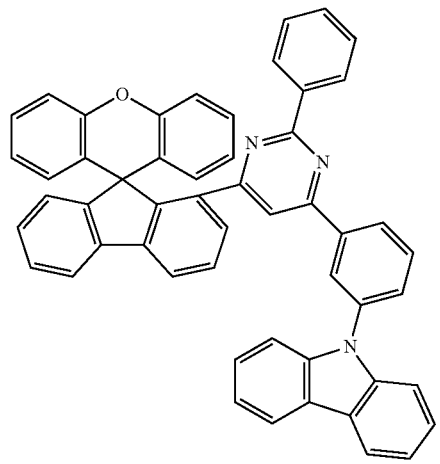
Formula 1-B-5
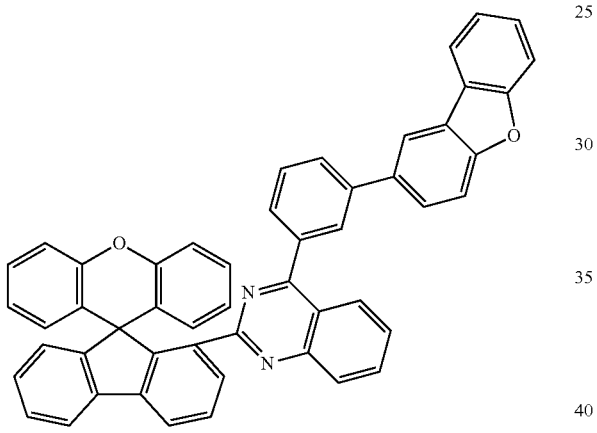
Formula 1-B-6
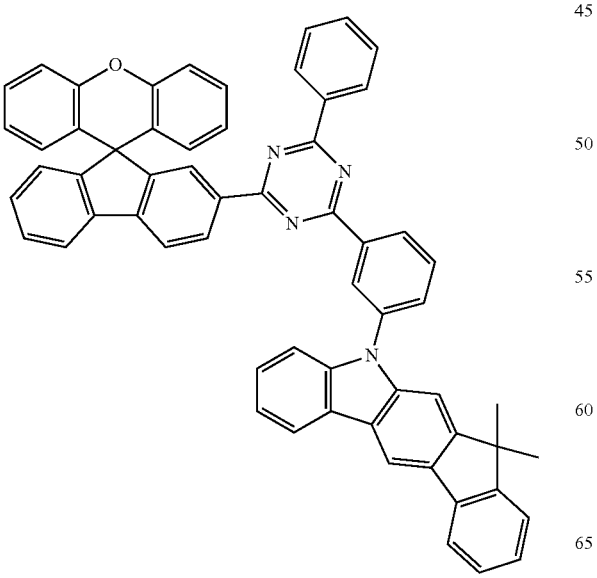
Formula 1-B-7
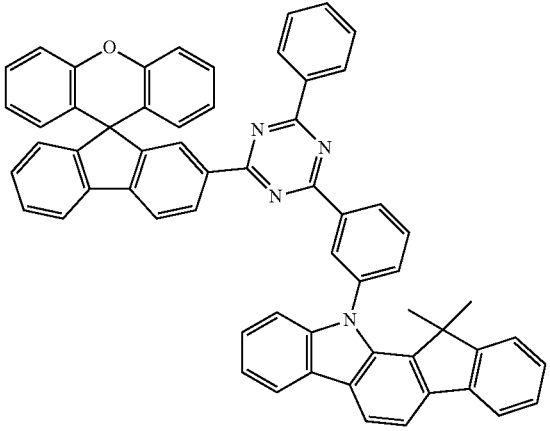
Formula 1-B-8
Formula 1-B-9
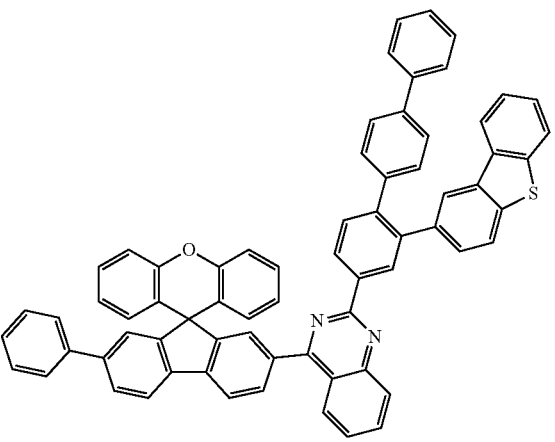

-continued
Formula 1-B-10
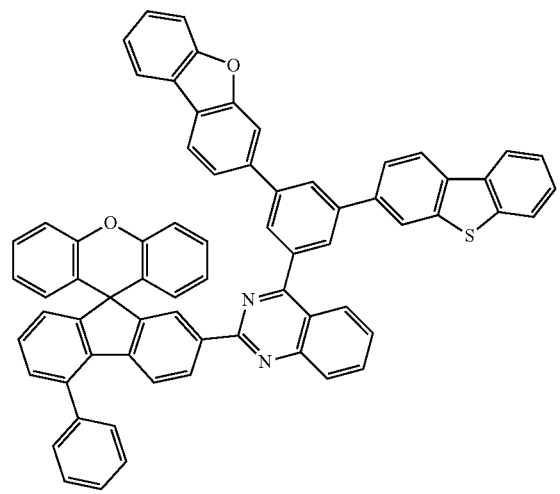
Formula 1-B-11
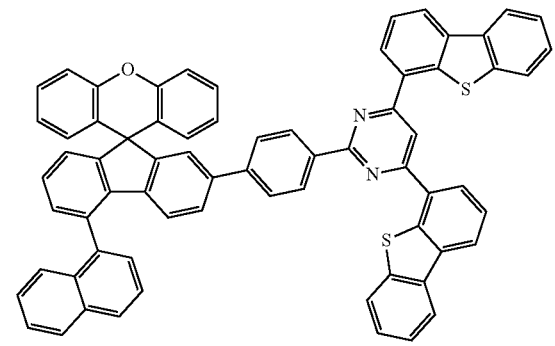
Formula 1-B-12
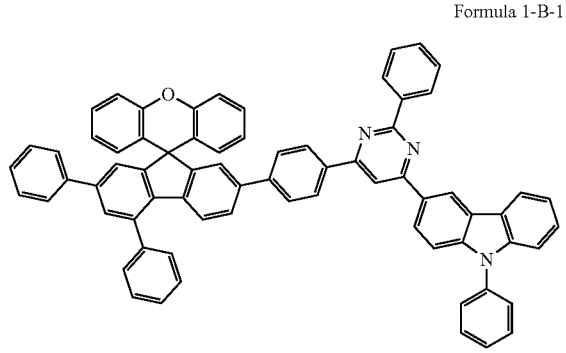
Formula 1-B-13
-continued
Formula 1-B-14
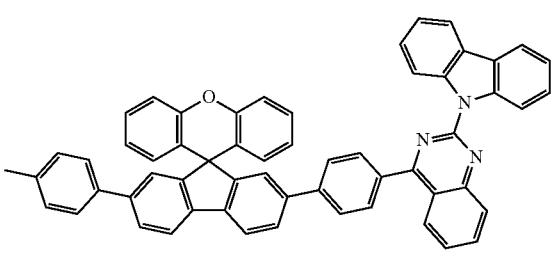
Formula 1-B-15
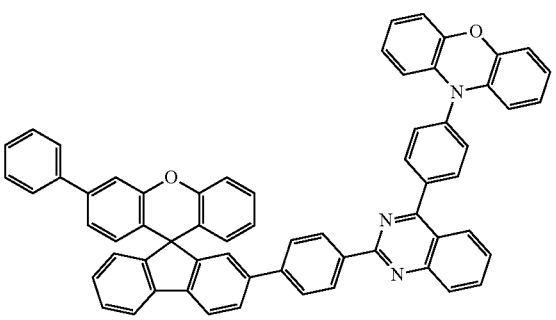
Formula 1-B-16
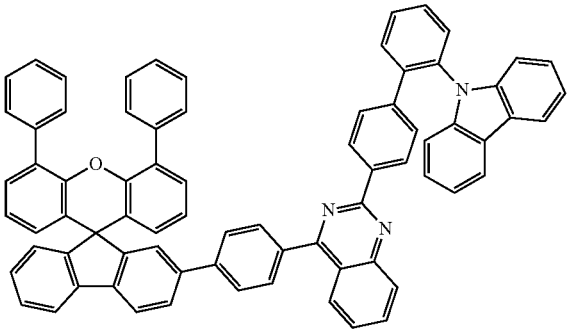
Formula 1-B-17
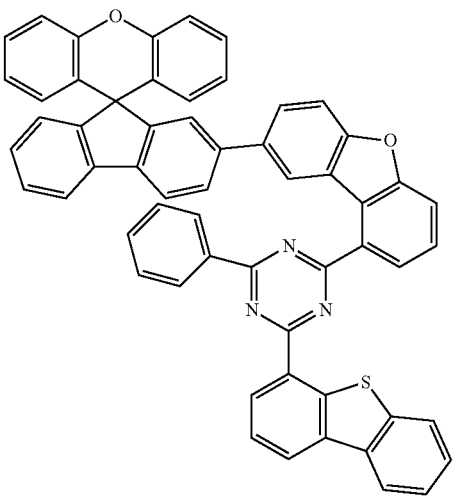

Formula 1-B-18
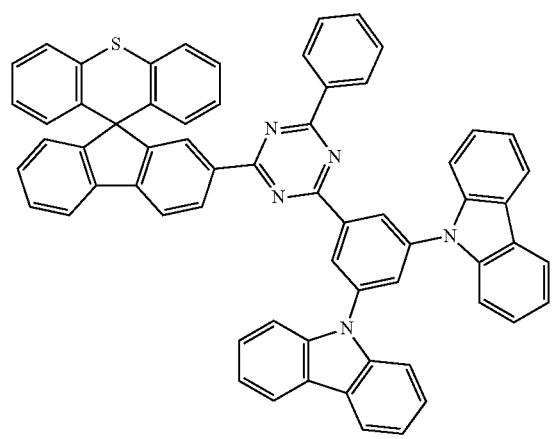
Formula 1-B-19
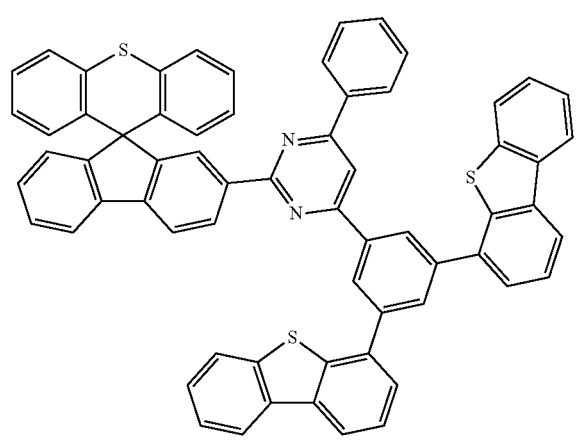
Formula 1-B-20
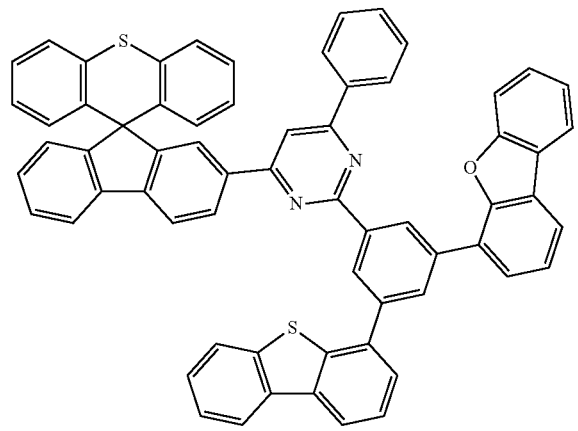
Formula 1-B-21
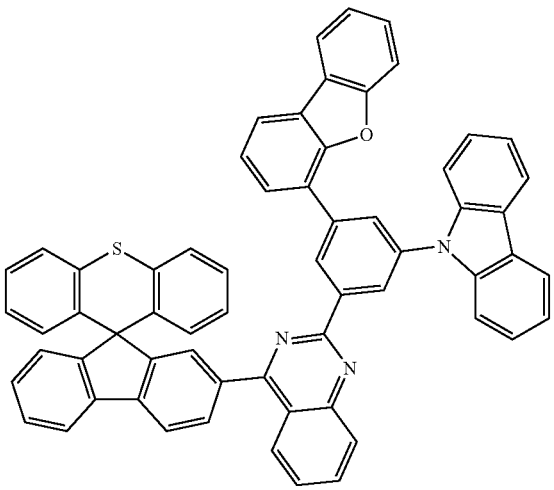
Formula 1-B-22
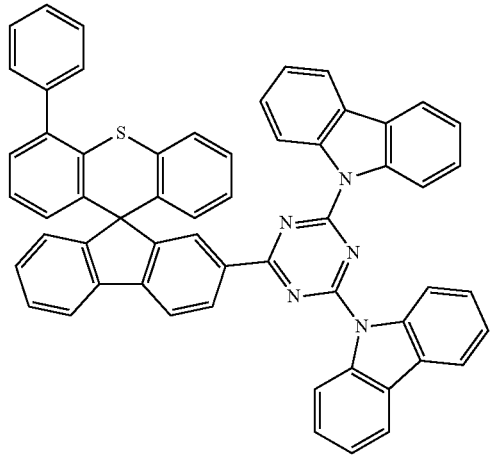
Formula 1-B-23
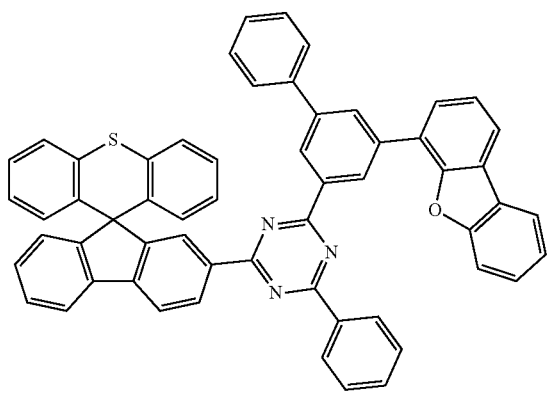

Formula 1-B-24
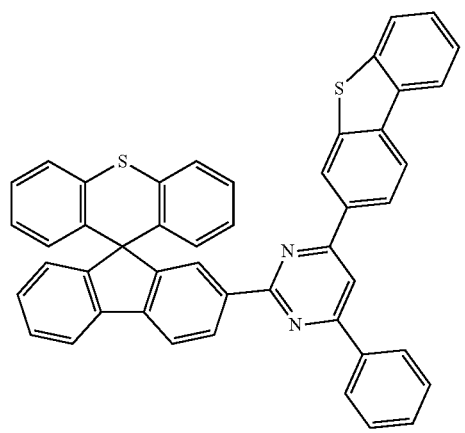
Formula 1-B-25
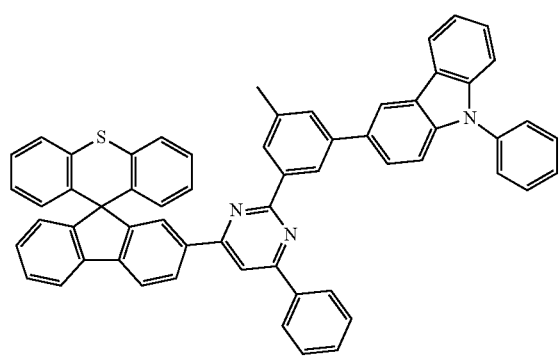
Formula 1-B-26
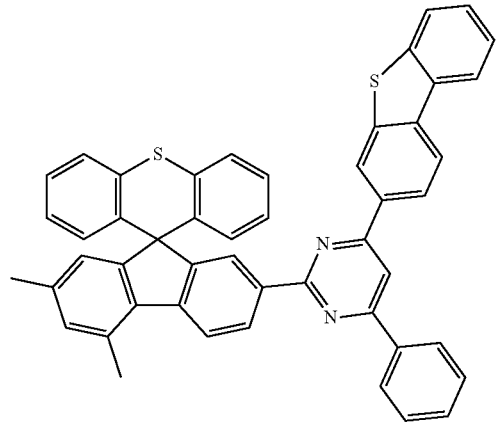
Formula 1-B-27
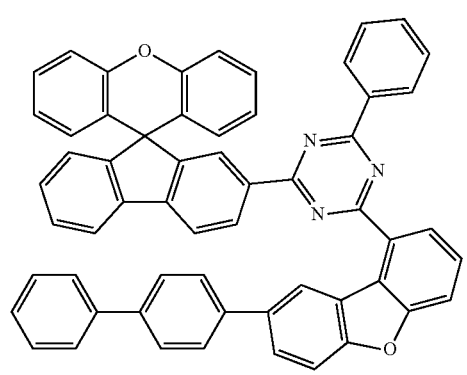
Formula 1-B-28
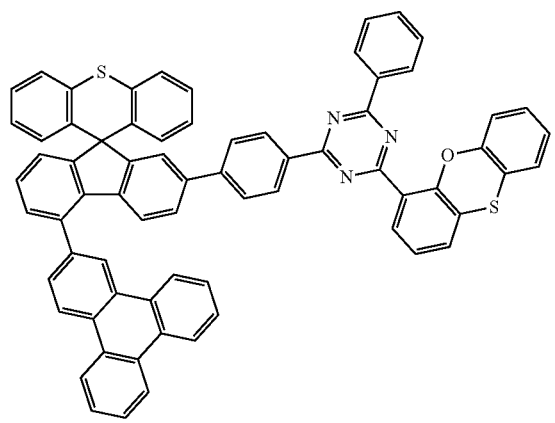
Formula 1-B-29
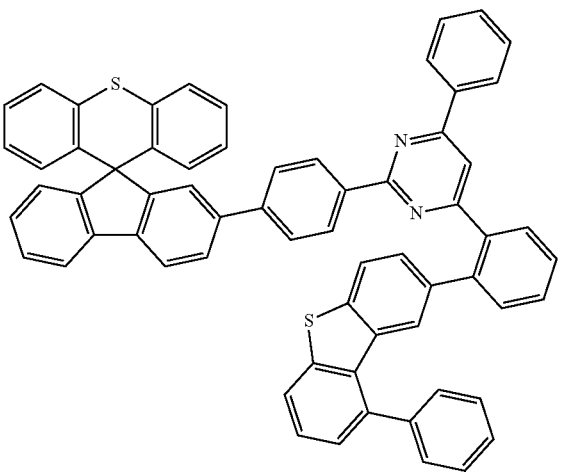
Formula 1-B-30
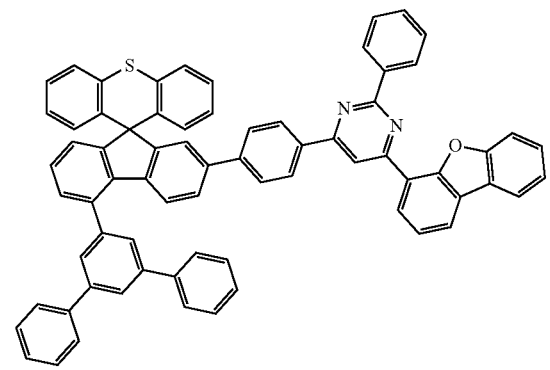

Formula 1-B-31
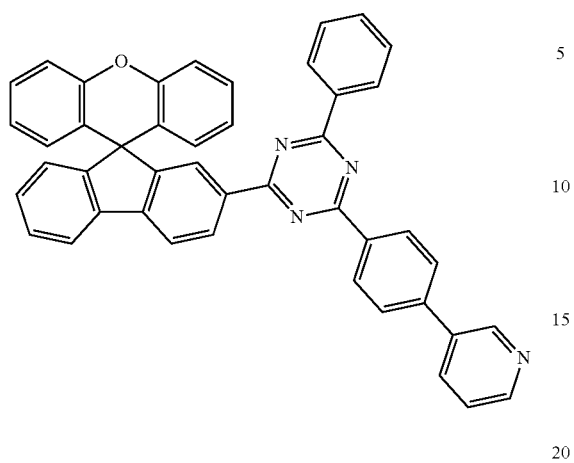
Formula 1-B-32
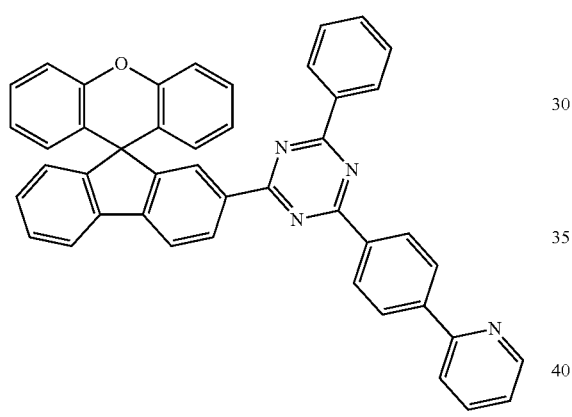
Formula 1-B-33
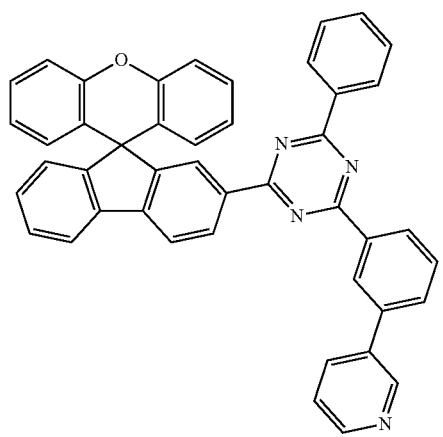
Formula 1-B-34
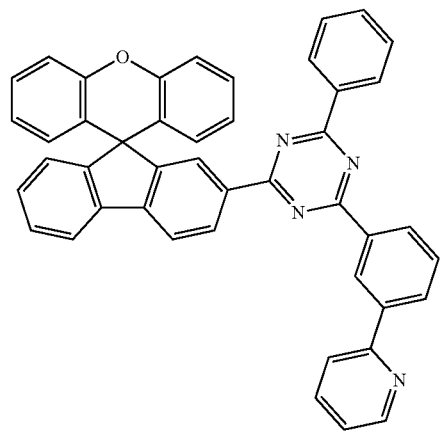
Formula 1-B-35
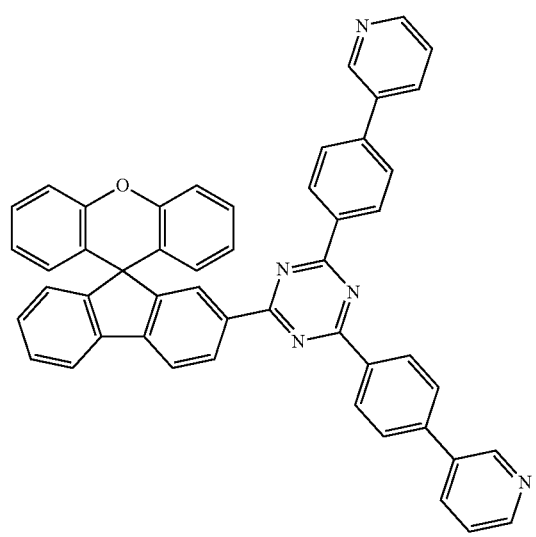
Formula 1-B-36
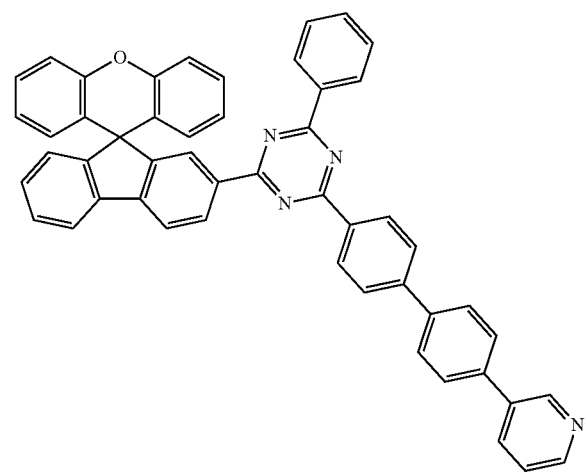

Formula 1-B-37
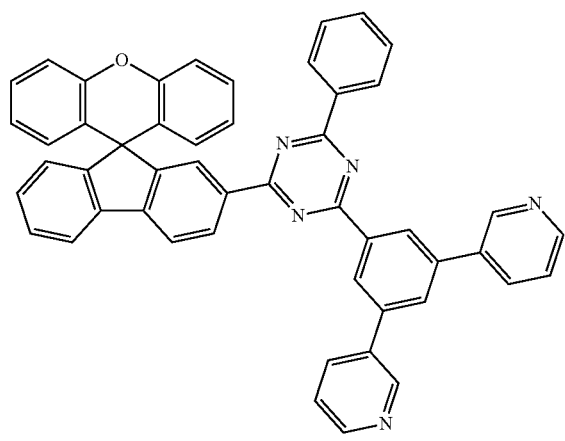
Formula 1-B-38
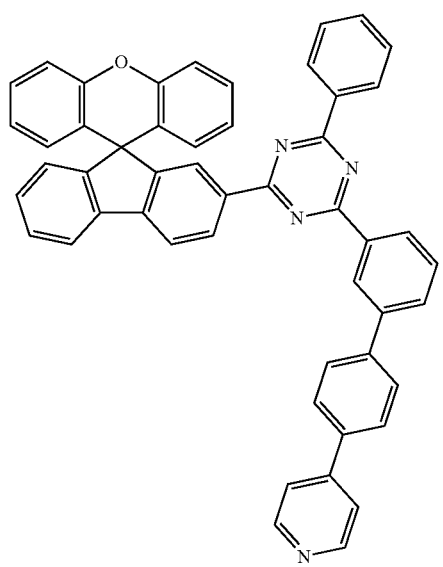
Formula 1-B-39
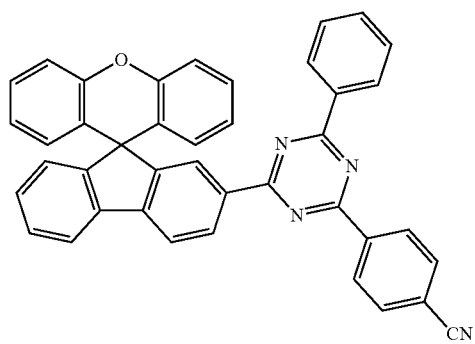
Formula 1-B-40
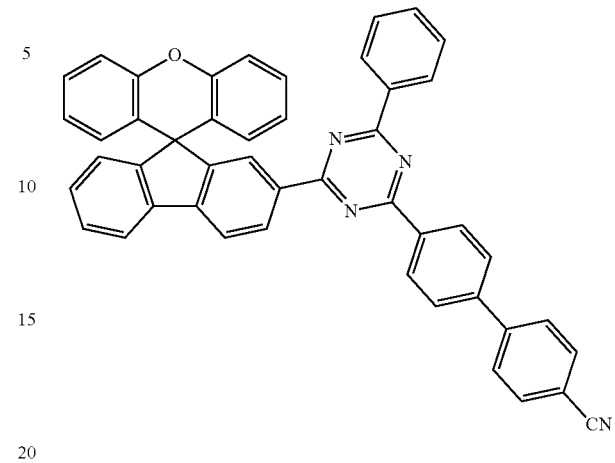
Formula 1-B-41
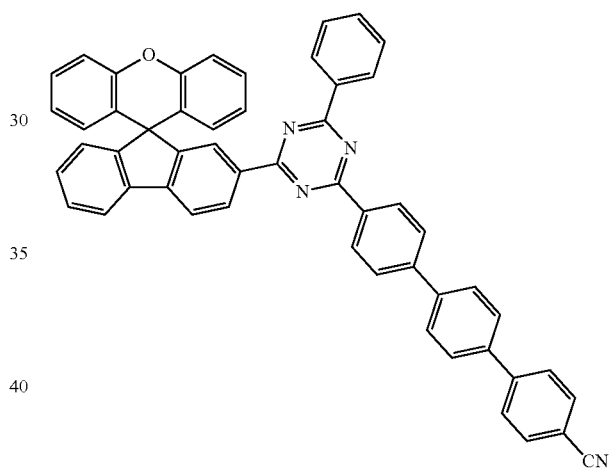
Formula 1-B-42
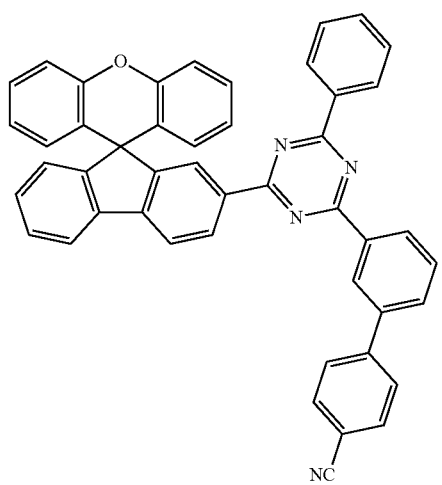

Formula 1-B-43
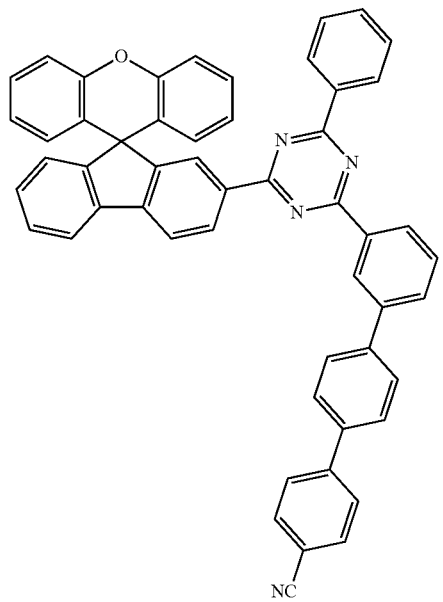
Formula 1-B-44
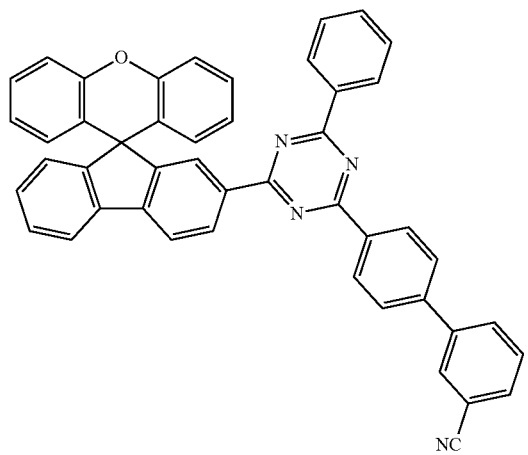
Formula 1-B-45
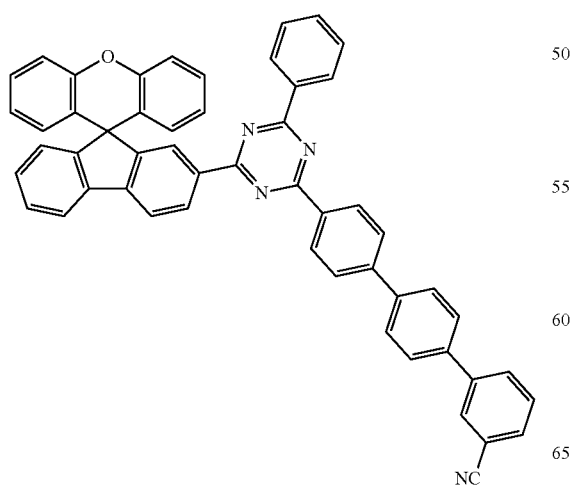
Formula 1-B-46
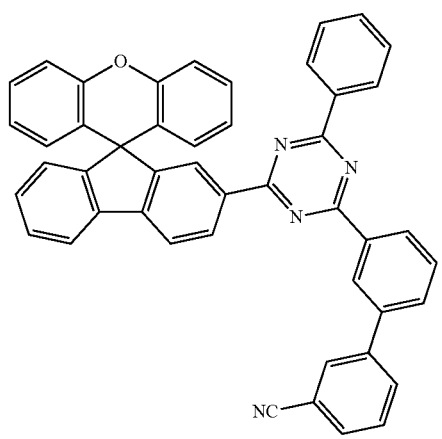
Formula 1-B-47
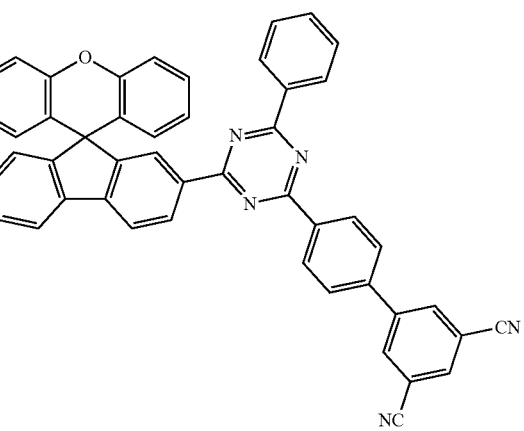
Formula 1-B-48

Formula 1-B-49
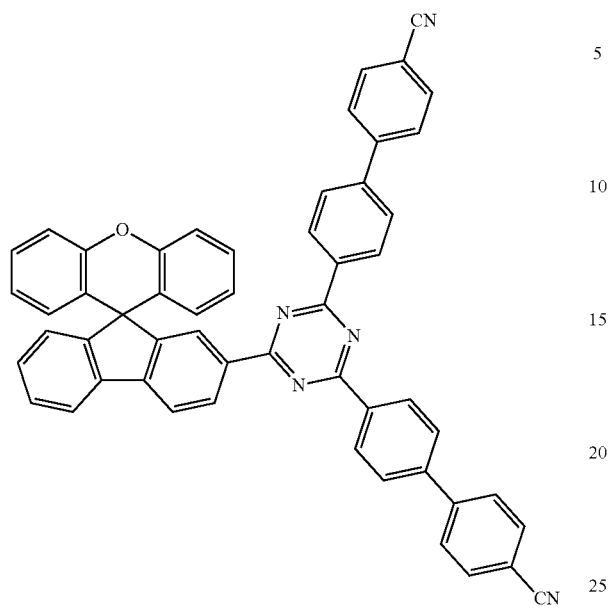
Formula 1-B-51
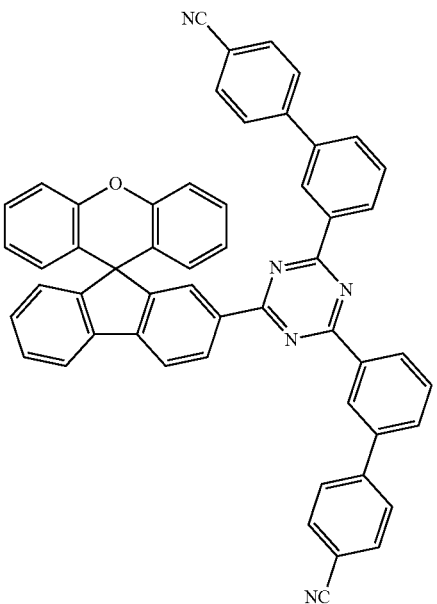
Formula 1-B-52
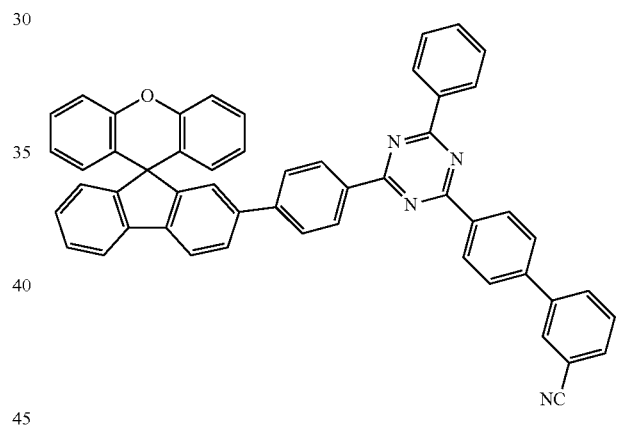
Formula 1-B-50
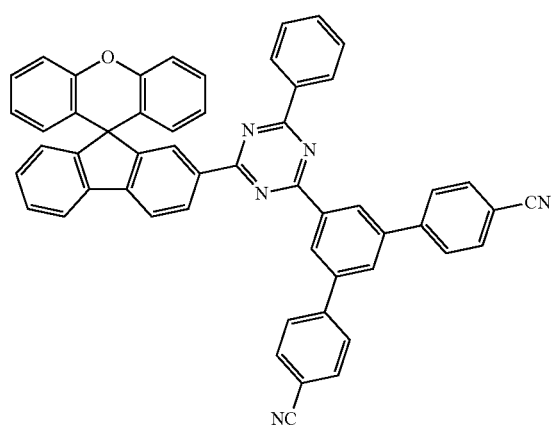
Formula 1-B-53
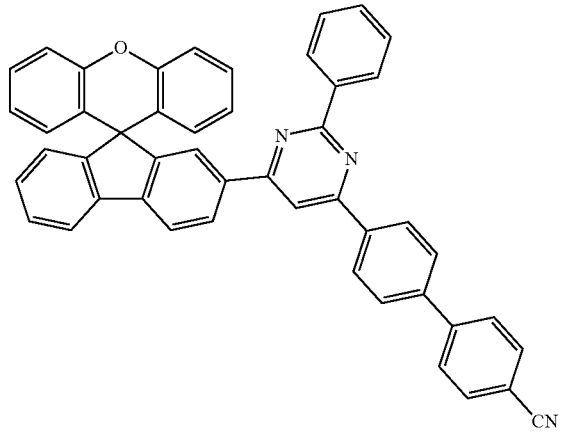

Formula 1-B-54
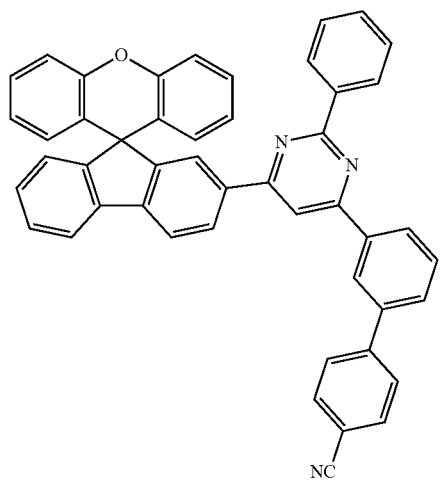
Formula 1-C-1
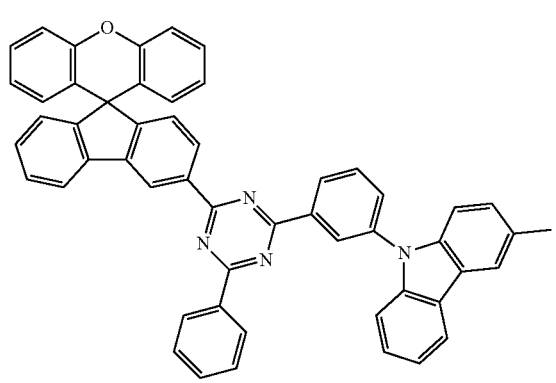
Formula 1-C-2
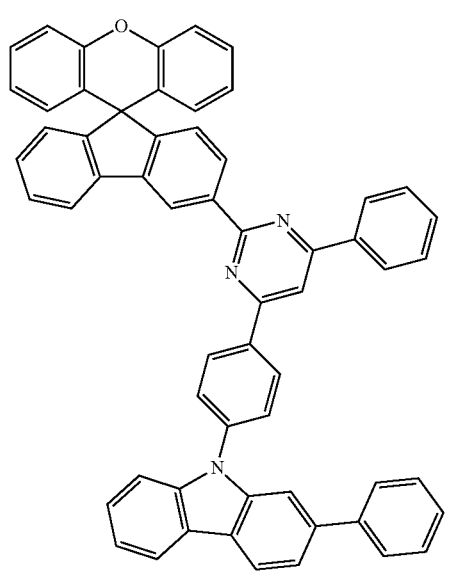
Formula 1-C-3
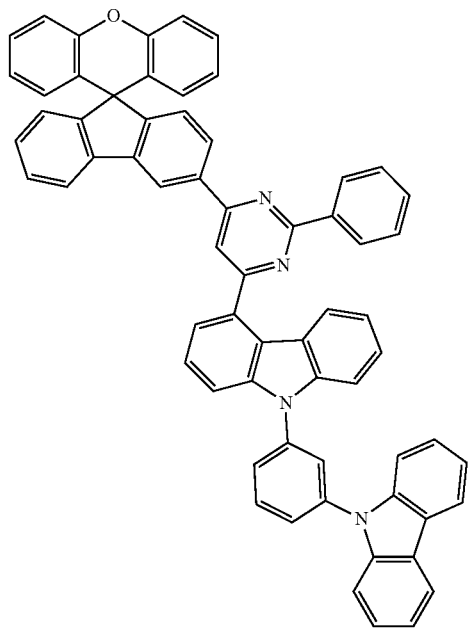
Formula 1-C-4
Formula 1-C-5
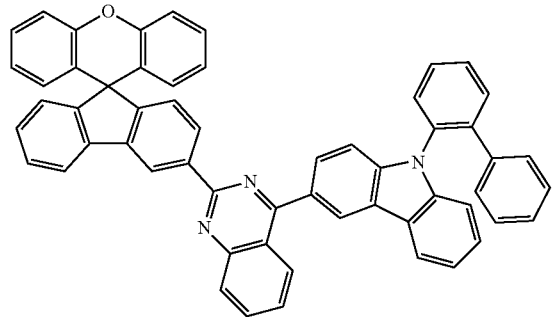

Formula 1-C-6
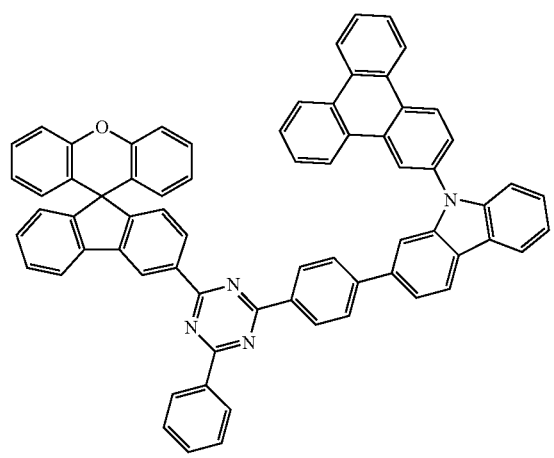
Formula 1-C-7
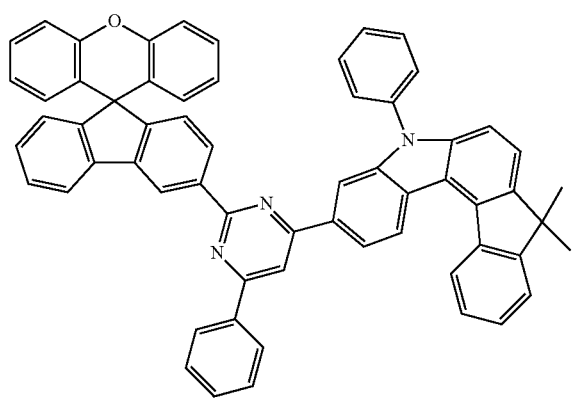
Formula 1-C-8
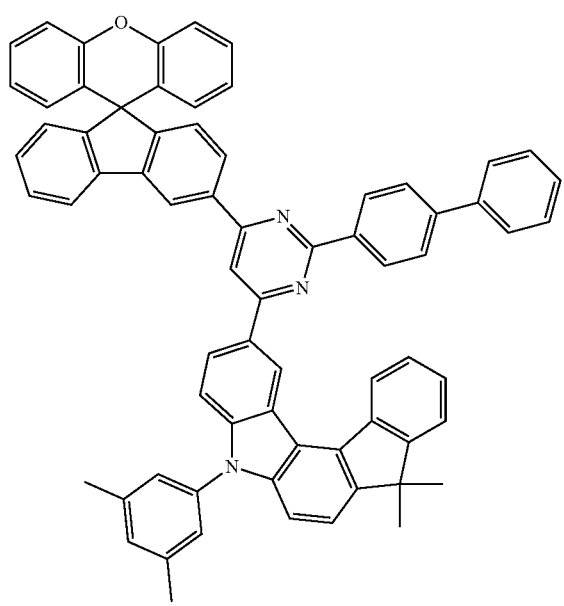
Formula 1-C-9
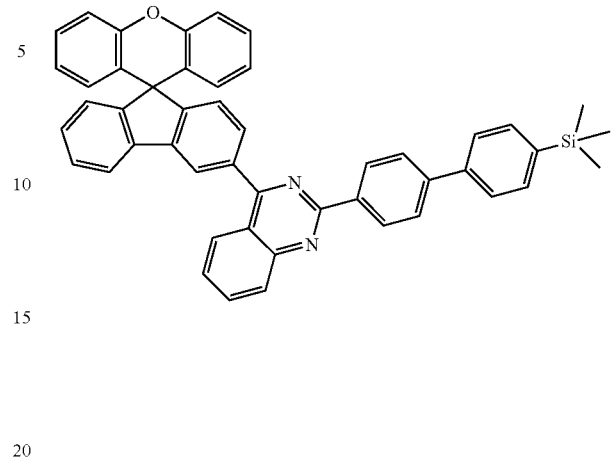
Formula 1-C-10
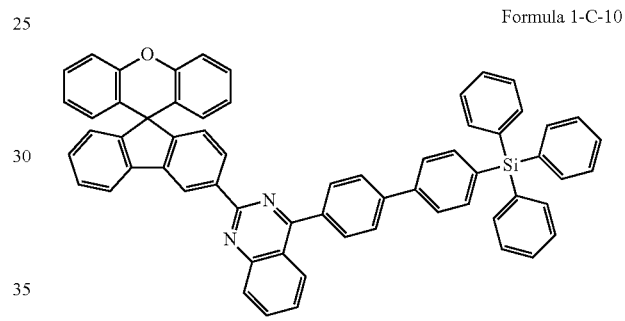
Formula 1-C-11
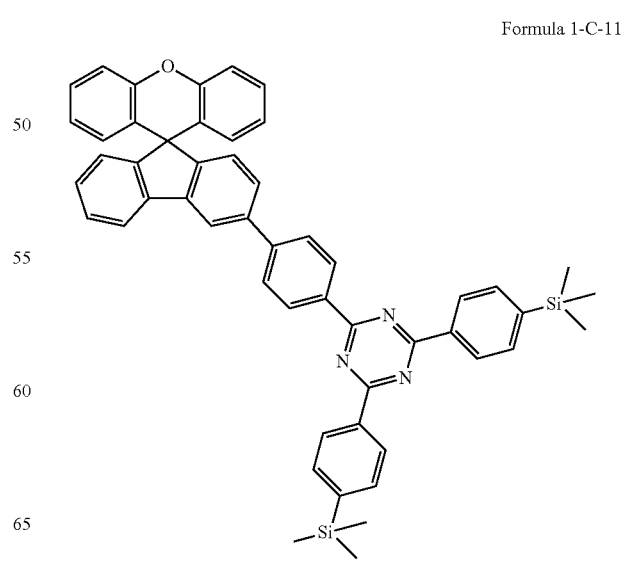

Formula 1-C-12
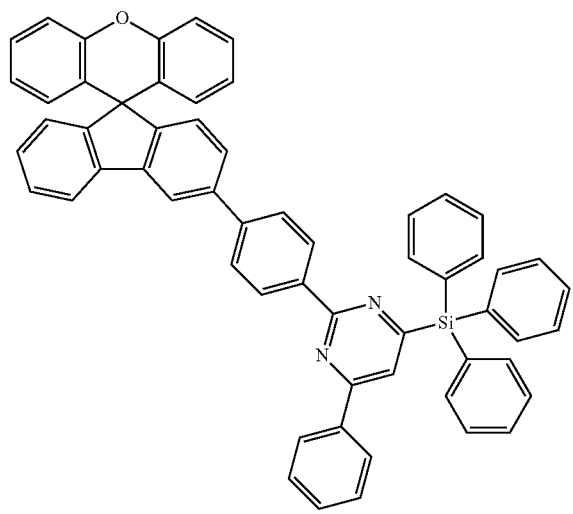
Formula 1-C-17
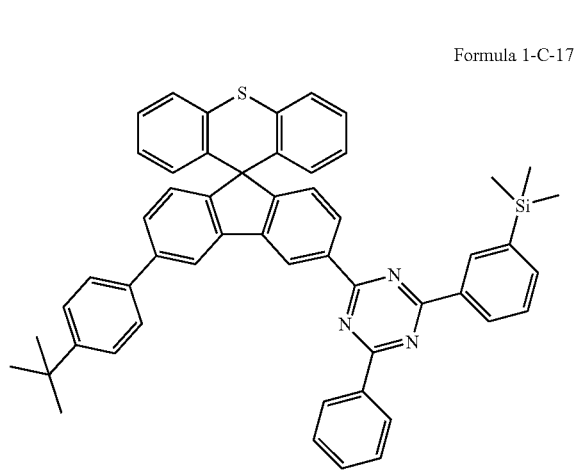
Formula 1-C-18
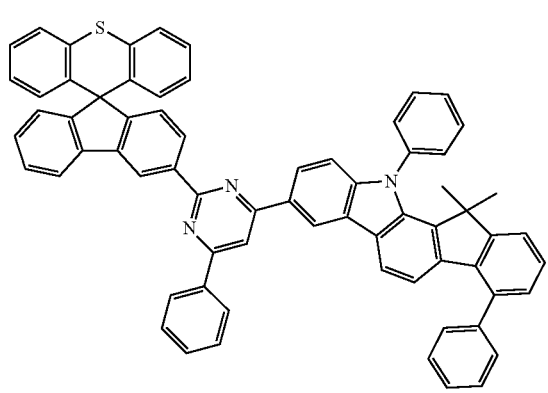
Formula 1-C-19
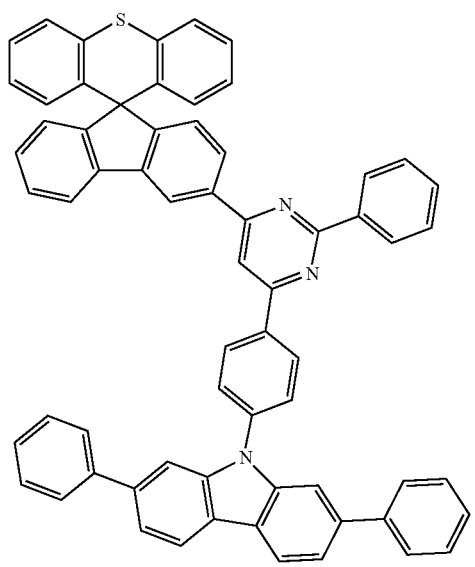
Formula 1-C-20
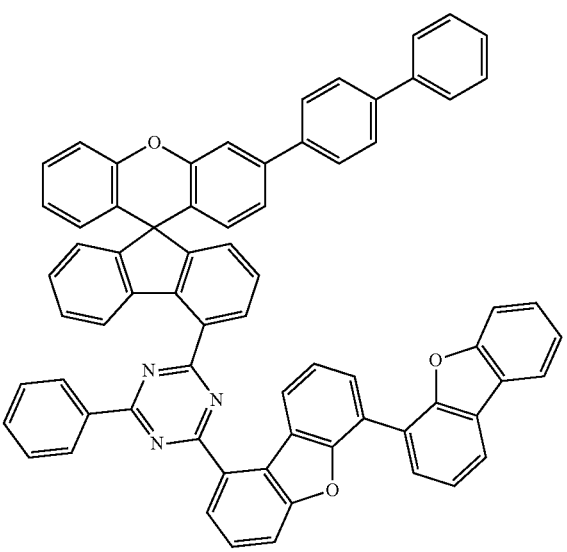
Formula 1-D-1
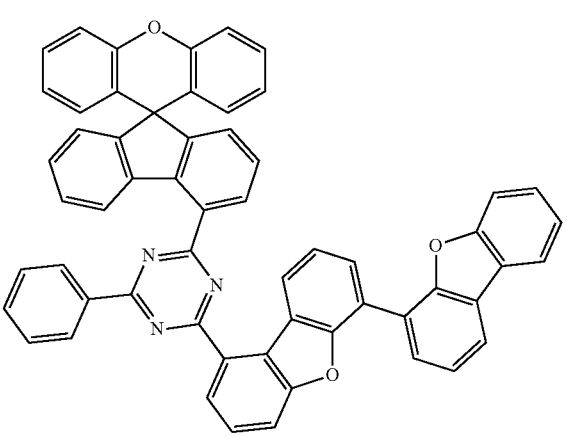

Formula 1-D-2
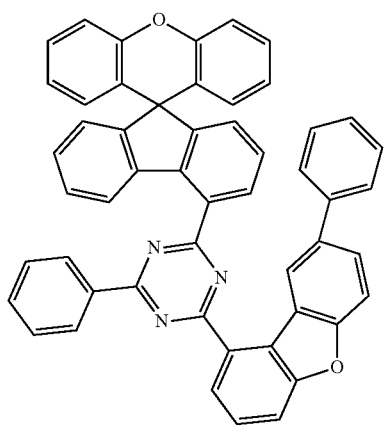
Formula 1-D-3
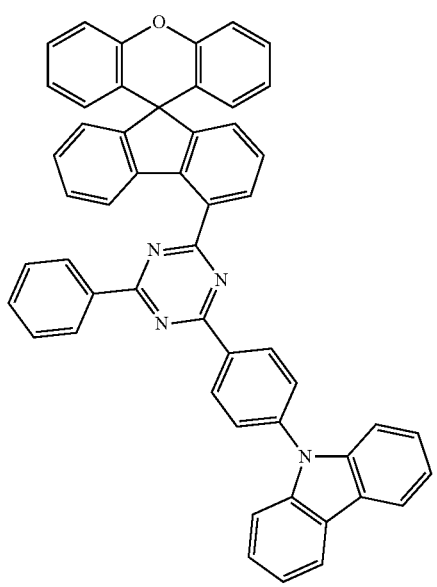
Formula 1-D-4
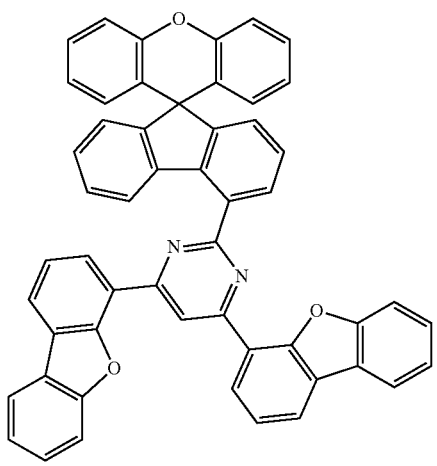
Formula 1-D-5
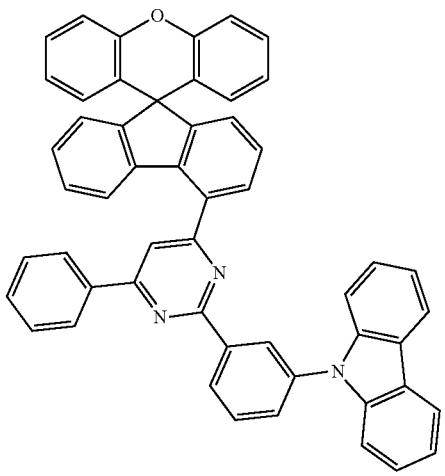
Formula 1-D-6
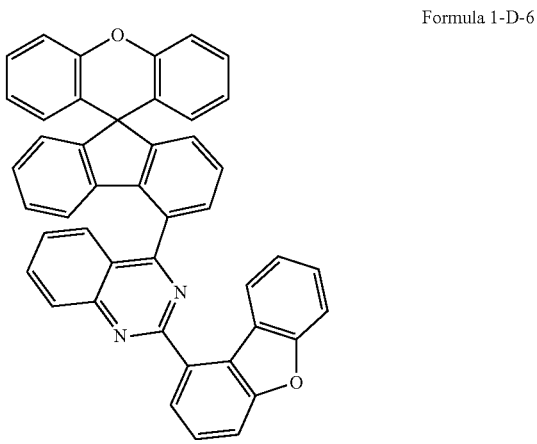
Formula 1-D-7
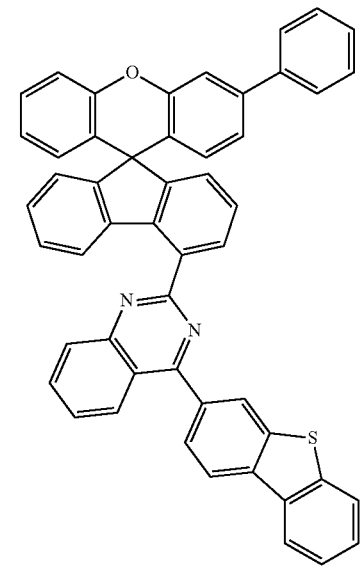

Formula 1-D-8
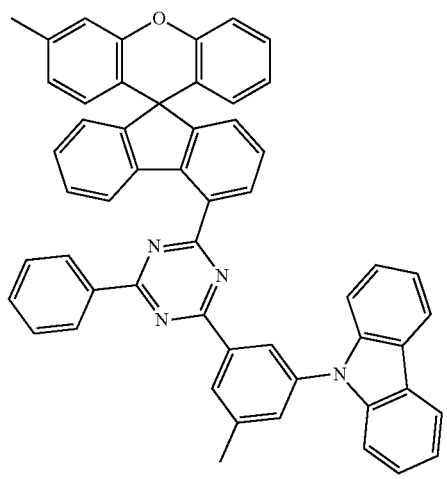
Formula 1-D-9
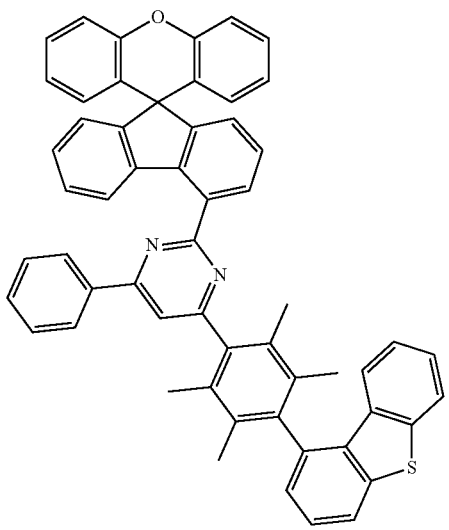
Formula 1-D-10
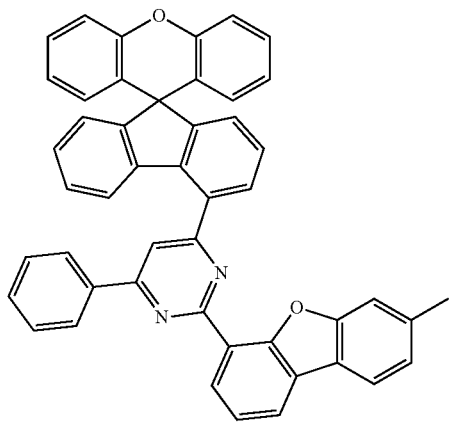
Formula 1-D-9b
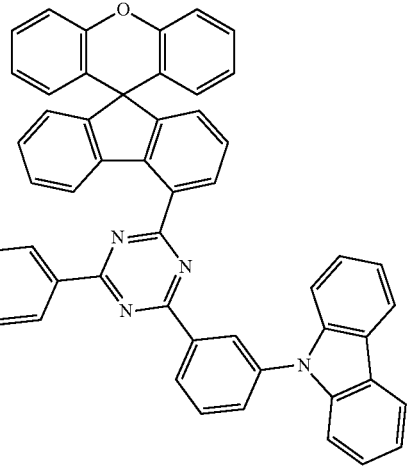
Formula 1-D-10
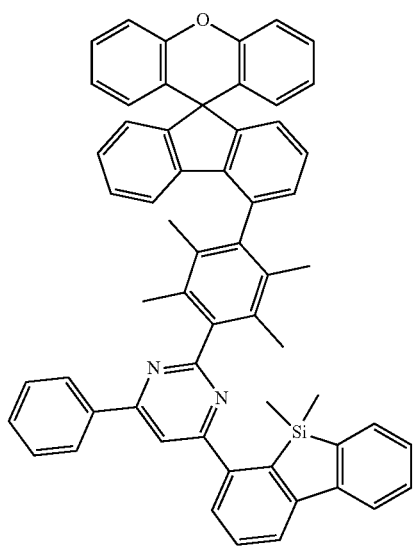
Formula 1-D-11
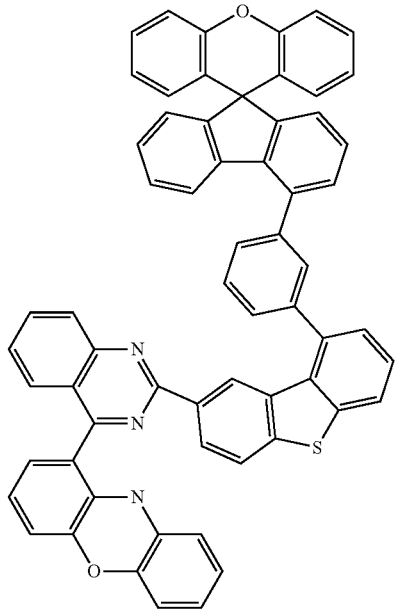

Formula 1-D-12
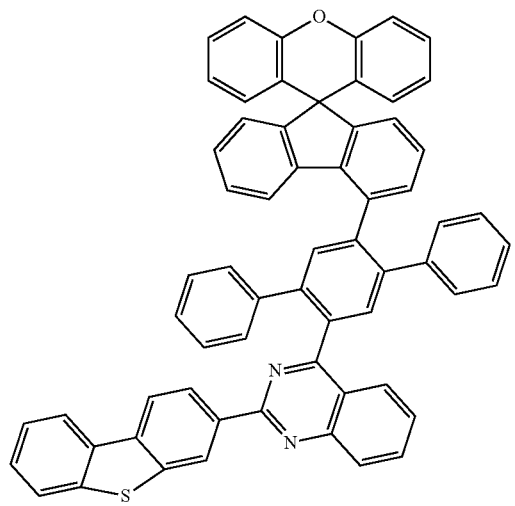
Formula 1-D-14
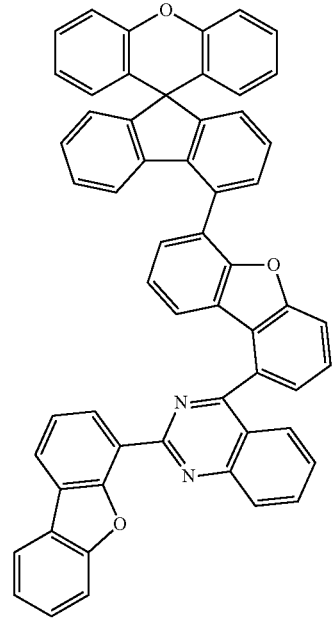
Formula 1-D-13
Formula 1-D-15
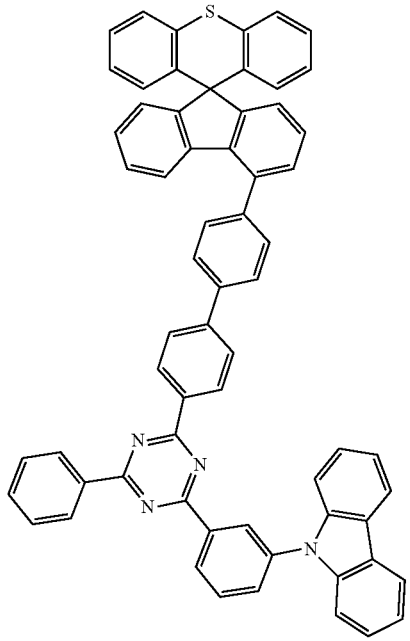

Formula 1-D-16
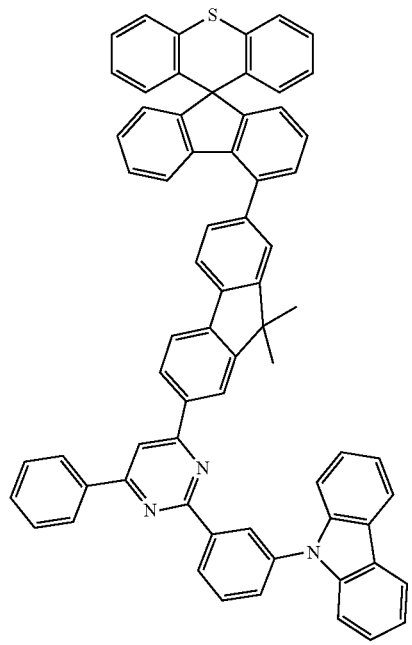
Formula 1-D-18
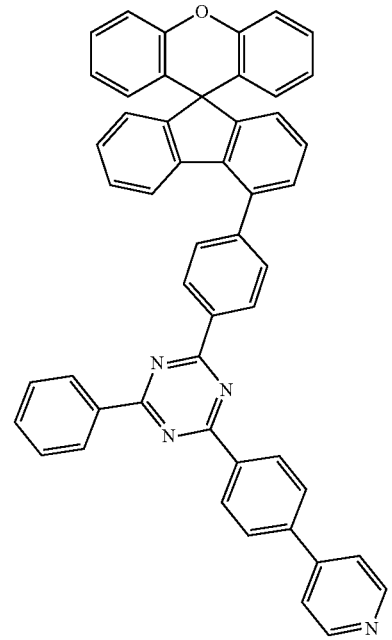
Formula 1-D-17
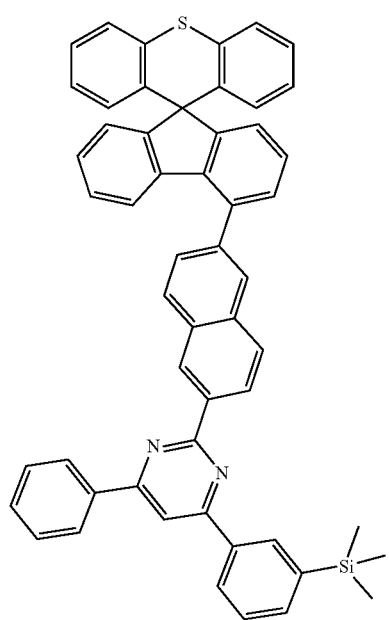
Formula 1-D-19
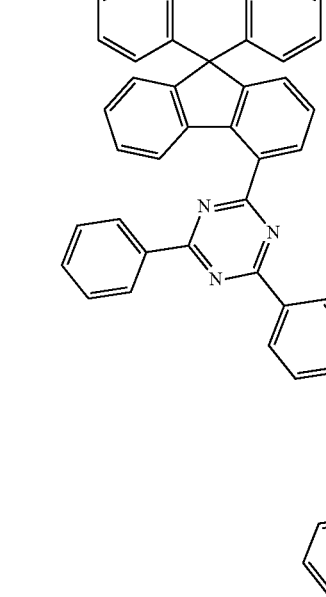

-continued
Formula 1-D-20
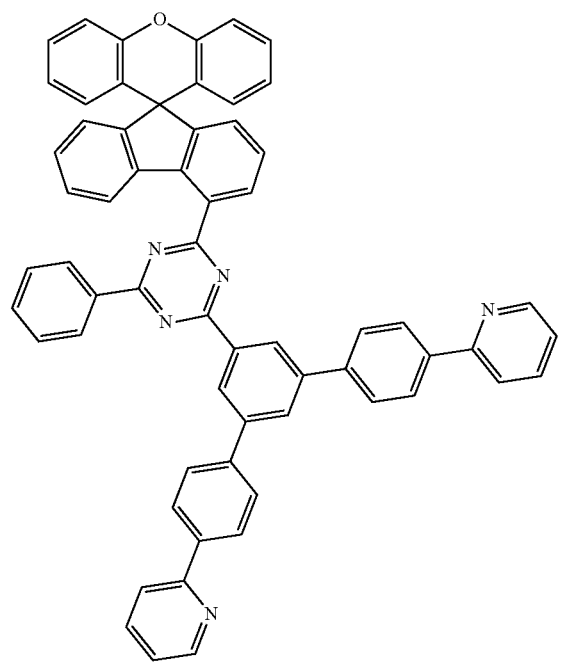
Formula 1-D-21
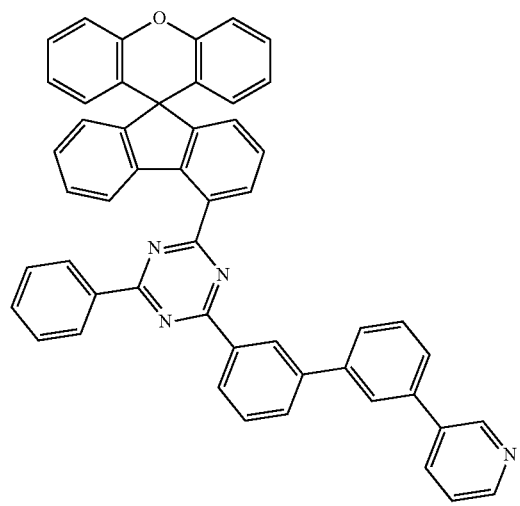
-continued
Formula 1-D-22
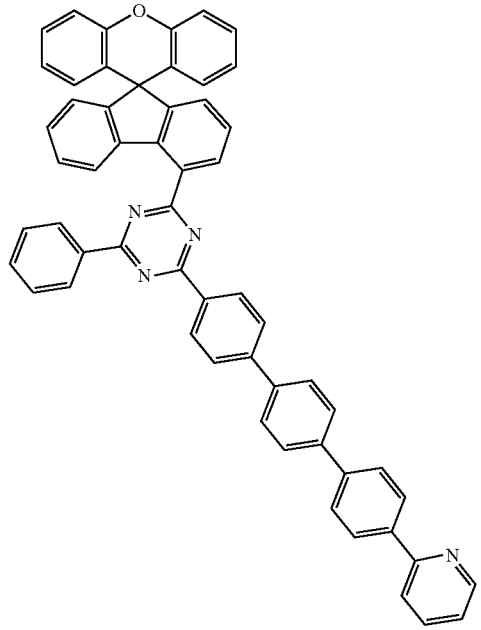
Formula 1-D-23
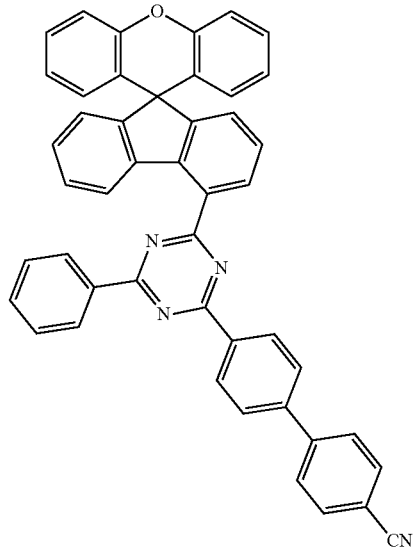

Formula 1-D-24
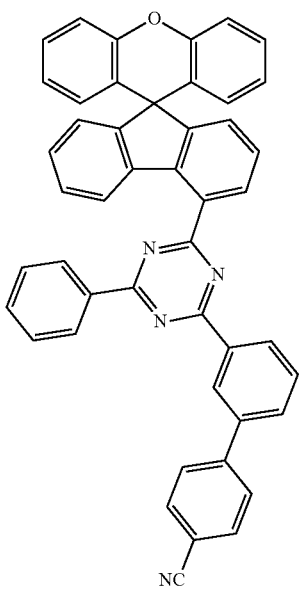
Formula 1-D-25
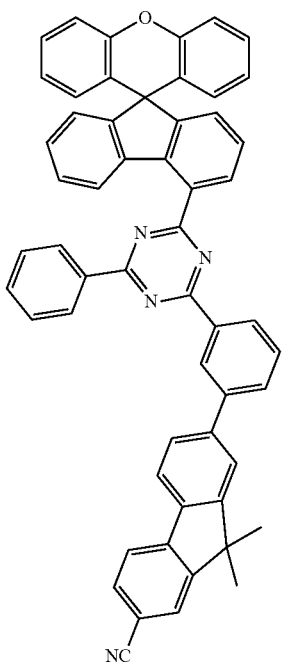
Formula 1-D-26
Formula 1-D-27
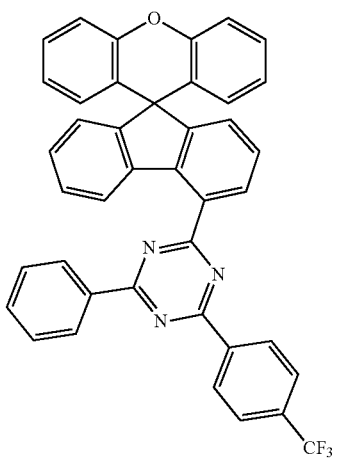
Formula 1-D-28
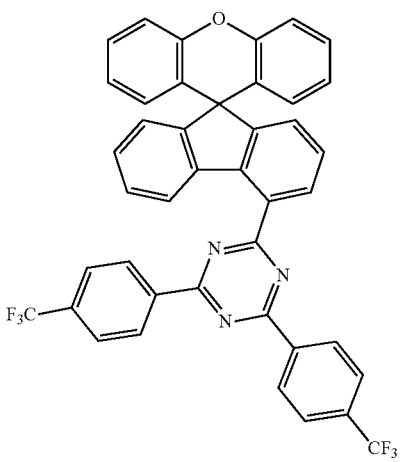

Formula 1-D-29

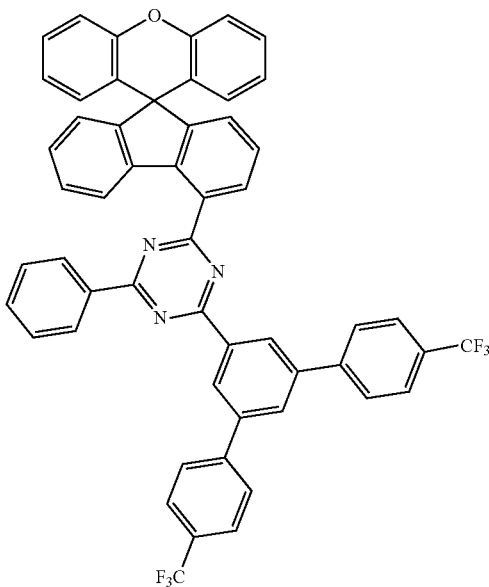

Formula 1-D-30

Formula 1-D-31

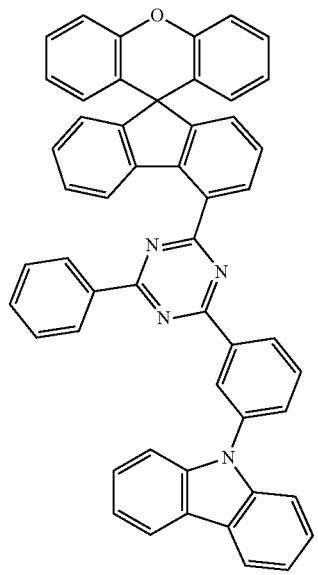

The compound of Chemical Formula 1 of the present invention includes a core structure in which xanthene (or thioxanthene) and fluorene are spiro-bonded, and is an asymmetric compound of the structure containing a substituent of triazine (or pyrimidine) in the fluorene, which has a lower crystallinity than a symmetrical structure. Therefore, the compound of the present invention has an effect of improving the lifetime because a dense film quality is formed during film formation. In addition, such intermolecular arrangement can improve the capability of injecting and transpering electrons and can realize device characteristics such as low voltage and high efficiency. In particular, P- or N-type Het introduced into triazine (or pyrimidine) acts as a kind of retarder that regulates electron mobility, thus minimizing efficiency-life trade-off phenomenon and achieving high efficiency and long lifetime at the same time. Accordingly, the organic light emitting device using the same can have high efficiency, low driving voltage, high luminance, long lifetime, and the like.

The compound of Chemical Formula 1 can be prepared by a preparation method as shown in Reaction Scheme A and Reaction Scheme B below. The above preparation method can be further specified in Preparation Examples described hereinafter.

[Reaction Scheme A]

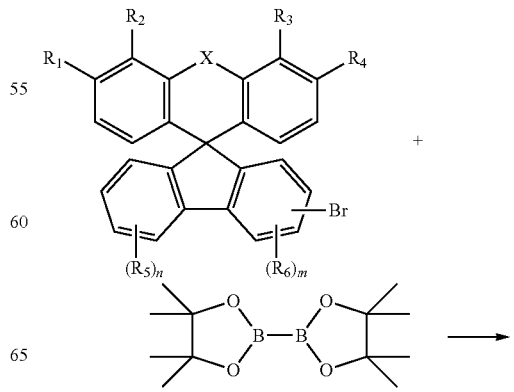

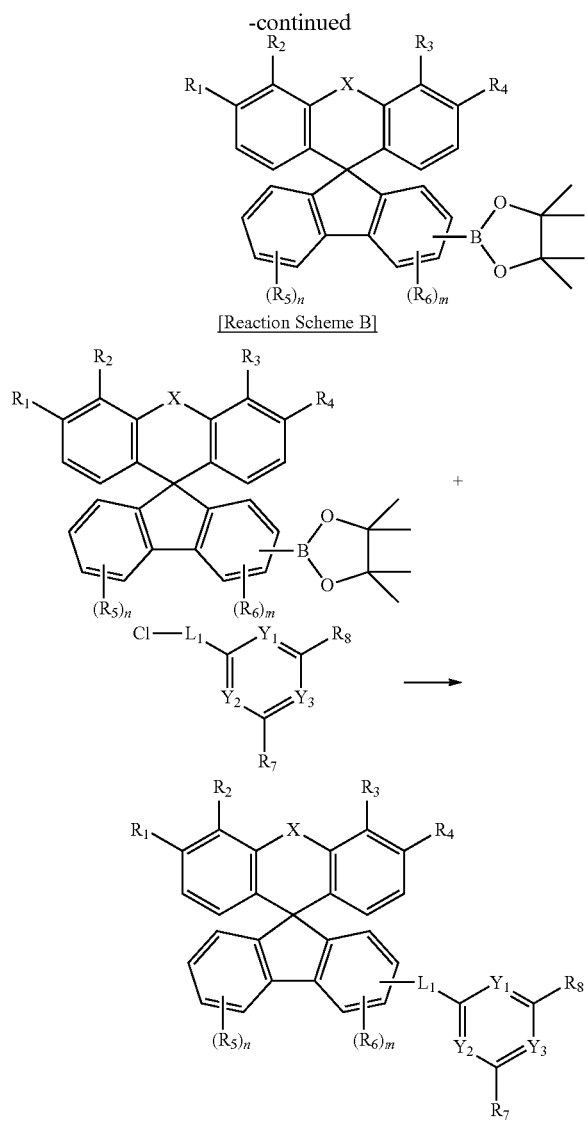

[Reaction Scheme B]

Reaction Scheme A and Reaction Scheme B can be sequentially performed.

In addition, in Reaction Scheme A and Reaction Scheme B, X, $Y_1$, $Y_2$, $Y_3$, $R_1$, $R_2$, $R_3$, $R_4$, $R_5$, $R_6$, $R_7$, $R_8$, $L_1$, m and n can be as described above, and further include additional substituents.

The above-mentioned reaction is Suzuki coupling reaction, which is preferably carried out in the presence of a palladium catalyst and a base. Moreover, the type of reactive groups and catalysts used in the Reaction Scheme can be changed as appropriate. The above preparation method can be further specified in Preparation Examples described hereinafter.

In another embodiment of the invention, there is provided an organic light emitting device including a compound of Chemical Formula 1 described above. As an example, there is provided an organic light emitting device including a first electrode; a second electrode provided opposite to the first electrode; and one or more organic material layers provided between the first electrode and the second electrode, wherein one or more layers of the organic material layers include the compound of Chemical Formula 1.

The organic material layer of the organic light emitting device of the present invention can have a single-layer structure, or it can have a multilayered structure in which two or more organic material layers are stacked. For example, the organic light emitting device of the present invention can have a structure comprising a hole injection layer, a hole transport layer, a light emitting layer, an electron transport layer, an electron injection layer and the like as the organic material layer. However, the structure of the organic light emitting device is not limited thereto, and it can include a smaller number of organic layers.

Further, the organic material layer can include a hole injection layer, a hole transport layer, or a layer for simultaneously performing hole injection and transport, wherein the hole injection layer, the hole transport layer, or the layer for simultaneously performing hole injection and transport include the compound of Chemical Formula 1.

Further, the organic material layer can include a light emitting layer, wherein the light emitting layer includes the compound of Chemical Formula 1.

Further, the organic material layer can include an electron transport layer or an electron injection layer, wherein the electron transport layer or the electron injection layer includes the compound of Chemical Formula 1.

Further, the electron transport layer, the electron injection layer, or the layer for simultaneously performing electron injection and transport include the compound of Chemical Formula 1. In particular, the compound of Chemical Formula 1 according to the present invention has excellent thermal stability, a deep HOMO level of 6.0 eV or higher, high triplet energy (ET) and hole stability. In addition, when the compound of Chemical Formula 1 is used for the organic material layer capable of simultaneously performing electron injection and electron transport, an n-type dopant used in the art can be mixed and used.

In addition, the organic layer includes a light emitting layer and an electron transport layer, wherein the electron transport layer can include a compound of Chemical Formula 1.

Further, the organic light emitting device according to the present invention can be a normal type organic light emitting device in which an anode, one or more organic material layers, and a cathode are sequentially stacked on a substrate. Further, the organic light emitting device according to the present disclosure can be an inverted type organic light emitting device in which a cathode, one or more organic material layers, and an anode are sequentially stacked on a substrate. For example, the structure of an organic light emitting device according to an embodiment of the present disclosure is illustrated in FIGS. 1 to 3.

FIG. 1 shows an example of an organic light emitting device comprising a substrate 1, an anode 2, a light emitting layer 3, and a cathode 4. In such a structure, the compound of Chemical Formula 1 can be included in the light emitting layer.

FIG. 2 shows an example of an organic light emitting device comprising a substrate 1, an anode 2, a hole injection layer 5, a hole transport layer 6, a light emitting layer 7, an electron transport layer 8 and a cathode 4. In such a structure, the compound of Chemical Formula 1 can be included in one or more layers of the hole injection layer, the hole transport layer, the light emitting layer and the electron transport layer.

The organic light emitting device according to the present invention can be manufactured by materials and methods known in the art, except that one or more layers of the organic material layers include the compound of Chemical Formula 1. In addition, when the organic light emitting device includes a plurality of organic material layers, the organic material layers can be formed of the same material or different materials.

When the number of organic material layers is two or more, each layer can be formed of components that emit light in different wavelength ranges, and for example, one layer can be an organic light emitting layer containing a fluorescent dopant, and the other layer can be an organic light emitting layer containing a phosphorescent dopant.

Further, when the number of organic material layers is two or more, each layer can have a structure in which the layers are sequentially stacked between an anode and a cathode, and a functional layer can be optionally included between the organic material layers.

On the other hand, the one organic material layer can be formed of two different components. In this case, the two component layers within a single layer can be in a divided form. FIG. 3 shows an example of an organic light emitting device comprising a substrate 1, an anode 2, a light emitting layer 3, and a cathode 4. In such a structure, the light emitting layer 3 is divided into two different parts 3-1 and 3-2, and the compound of Chemical Formula 1 can be included in either or both of the portions of the light emitting layer.

In the organic light emitting device according to the present invention, the organic material layer can be a blue fluorescent light emitting layer, and the blue fluorescent light emitting layer can be included in three or more layers. In this case, each layer can have a structure in which the layers are sequentially stacked between an anode and a cathode, and each blue fluorescent light emitting layer can optionally include a functional layer therebetween.

For example, the organic light emitting device according to the present invention can be manufactured by sequentially stacking a first electrode, an organic material layer and a second electrode on a substrate. In this case, the organic light emitting device can be manufactured by depositing a metal, metal oxides having conductivity, or an alloy thereof on the substrate using a PVD (physical vapor deposition) method such as a sputtering method or an e-beam evaporation method to form an anode, forming organic material layers including the hole injection layer, the hole transport layer, the light emitting layer and the electron transport layer thereon, and then depositing a material that can be used as the cathode thereon. In addition to such a method, the organic light emitting device can be manufactured by sequentially depositing a cathode material, an organic material layer and an anode material on a substrate.

In addition, the compound of Chemical Formula 1 can be formed into an organic material layer by a solution coating method as well as a vacuum deposition method at the time of manufacturing an organic light emitting device. Herein, the solution coating method means a spin coating, a dip coating, a doctor blading, an inkjet printing, a screen printing, a spray method, a roll coating, or the like, but is not limited thereto.

In addition to such a method, the organic light emitting device can be manufactured by sequentially depositing a cathode material, an organic material layer and an anode material on a substrate (International Publication WO2003/012890). However, the manufacturing method is not limited thereto.

As an example, the first electrode is an anode, and the second electrode is a cathode, or alternatively the first electrode is a cathode and the second electrode is an anode.

As the anode material, generally, a material having a large work function is preferably used so that holes can be smoothly injected into the organic material layer. Specific examples of the anode material include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as $ZnO:Al$ or $SnO_2:Sb$; conductive polymers such as poly(3-methylthiophene), poly[3,4-(ethylene-1,2-dioxy)thiophene] (PEDOT), polypyrrole, and polyaniline, and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or $LiO_2$/Al, and the like, but are not limited thereto.

The hole injection layer is a layer for injecting holes from the electrode, and the hole injection material is preferably a compound which has a capability of transporting the holes, thus has a hole injecting effect in the anode and an excellent hole injecting effect to the light emitting layer or the light emitting material, prevents excitons produced in the light emitting layer from moving to a hole injection layer or the electron injection material, and is excellent in the ability to form a thin film. It is preferable that a HOMO (highest occupied molecular orbital) of the hole injection material is between the work function of the anode material and a HOMO of a peripheral organic material layer. Specific examples of the hole injection material include metal porphyrine, oligothiophene, an arylamine-based organic material, a hexanitrile-hexaazatriphenylene-based organic material, a quinacridone-based organic material, a perylene-based organic material, anthraquinone, polyaniline and polythiophene-based conductive polymer, and the like, but are not limited thereto.

The hole transport layer is a layer that receives holes from a hole injection layer and transports the holes to the light emitting layer, and it is suitably a material having large mobility to the holes, which can receive holes from the anode or the hole injection layer and transfer the holes to the light emitting layer. Specific examples thereof include an arylamine-based organic material, a conductive polymer, a block copolymer in which a conjugate portion and a non-conjugate portion are present together, and the like, but are not limited thereto.

The light emitting material is preferably a material which can receive holes and electrons transported from a hole transport layer and an electron transport layer, respectively, and combine the holes and the electrons to emit light in a visible ray region, and has good quantum efficiency to fluorescence or phosphorescence. Specific examples of the light emitting material include an 8-hydroxy-quinoline aluminum complex ($Alq_3$), a carbazole-based compound, a dimerized styryl compound, BAlq, a 10-hydroxybenzoquinoline-metal compound, a benzoxazole, benzothiazole and benzimidazole-based compound, a poly(p-phenylenevinylene) (PPV)-based polymer, a spiro compound, polyfluorene, lubrene, and the like, but are not limited thereto.

The light emitting layer can include a host material and a dopant material. The host material can be a fused aromatic ring derivative, a heterocycle-containing compound or the like. Specific examples of the fused aromatic ring derivatives include anthracene derivatives, pyrene derivatives, naphthalene derivatives, pentacene derivatives, phenanthrene compounds, fluoranthene compounds, and the like. Examples of the heterocyclic-containing compounds include carbazole derivatives, dibenzofuran derivatives, ladder-type furan compounds, pyrimidine derivatives, and the like, but are not limited thereto.

Examples of the dopant material include an aromatic amine derivative, a styrylamine compound, a boron complex, a fluoranthene compound, a metal complex, and the like. Specifically, the aromatic amine derivative is a substituted or unsubstituted fused aromatic ring derivative having an arylamino group, and examples thereof include pyrene, anthracene, chrysene, periflanthene and the like, which have an arylamino group. The styrylamine compound is a compound where at least one arylvinyl group is substituted in substituted or unsubstituted arylamine, in which one or two or more substituent groups selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, the metal complex includes an iridium complex, a platinum complex, and the like, but is not limited thereto.

The electron transport layer is a layer which receives electrons from an electron injection layer and transports the electrons to a light emitting layer, and an electron transport material is suitably a material which can receive electrons well from a cathode and transfer the electrons to a light emitting layer, and has a large mobility for electrons. Specific examples of the electron transport material include: an Al complex of 8-hydroxyquinoline, a complex including Alq$_3$, an organic radical compound, a hydroxyflavone-metal complex, and the like, but are not limited thereto. The electron transport layer can be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and is preferably a compound which has a capability of transporting electrons, has an effect of injecting electrons from a cathode and an excellent effect of injecting electrons into a light emitting layer or a light emitting material, prevents excitons produced from the light emitting layer from moving to a hole injection layer, and is also excellent in the ability to form a thin film.

Specific examples of the electron injection layer include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato)-zinc, bis(8-hydroxyquinolinato)copper, bis(8-hydroxy-quinolinato)manganese, tris(8-hydroxyquinolinato)-aluminum, tris (2-methyl-8-hydroxyquinolinato)aluminum, tris(8-hydroxyquinolinato)gallium, bis(10-hydroxy-benzo[h]quinolinato) beryllium, bis(10-hydroxybenzo-[h]quinolinato)zinc, bis(2-methyl-8-quinolinato)-chlorogallium, bis(2-methyl-8-quinolinato)(o-cresolato)gallium, bis(2-methyl-8-quinolinato) (1-naphtholato)aluminum, bis(2-methyl-8-quinolinato) (2-naphtholato)gallium, and the like, but are not limited thereto.

The organic light emitting device according to the present invention can be a front side emission type, a back side emission type, or a double side emission type according to the used material.

In addition, the compound of Chemical Formula 1 can be included in an organic solar cell or an organic transistor in addition to an organic light emitting device.

The preparation of the compound of Chemical Formula 1 and the organic light emitting device containing the same will be described in detail in the following examples. However, these examples are presented for illustrative purposes only, and are not intended to limit the scope of the present invention.

Preparation Example: Synthesis of Intermediate Compound (1) Synthesis Example 1: Preparation of the Compound of Chemical Formula 2A

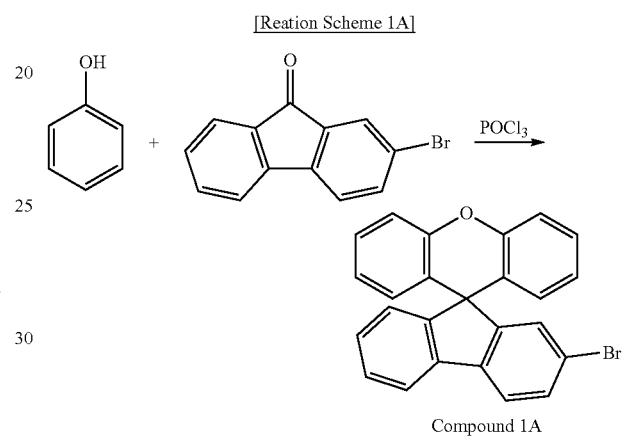

(1) Preparation of Chemical Formula 1A

A mixture of 2-bromo-9H-fluoren-9-one (10 g, 38.6 mmol), phenol (7.25 g, 77.2 mmol) and excess phosphoryl chloride (POCl$_3$) was refluxed at 120° C. After cooling to room temperature, excess ethanol was added and filtered. The filtered solid was dissolved in pyridine and heated, then cooled to room temperature and filtered. Recrystallization with chloroform and ethyl acetate gave the compound of Formula 1A (14 g, yield: 87%).

MS:[M+H]$^+$=411

(2) Preparation of Chemical Formula 2A

2-Bromospiro[fluorene-9,9'-xanthene] (45 g, 109 mmol) and bispinacolalate diborone (30 g, 119.9 mmol) were added to dioxane (1500 ml), and the mixture was heated and dissolved at 130° C. P(Cy)$_3$ and Pd(dba)$_2$ were mixed in a molar ratio of 2:1 (total 1.88 g) and then refluxed for 4 hours. After cooling to room temperature, the reaction mixture was concentrated and purified by column chromatography to give the compound of Formula 2A (42 g, yield: 84%).

MS: [M+H]$^+$=458

(2) Synthesis Example 2: Preparation of the Compound of Chemical Formula 2B

[Reaction Scheme 1B]

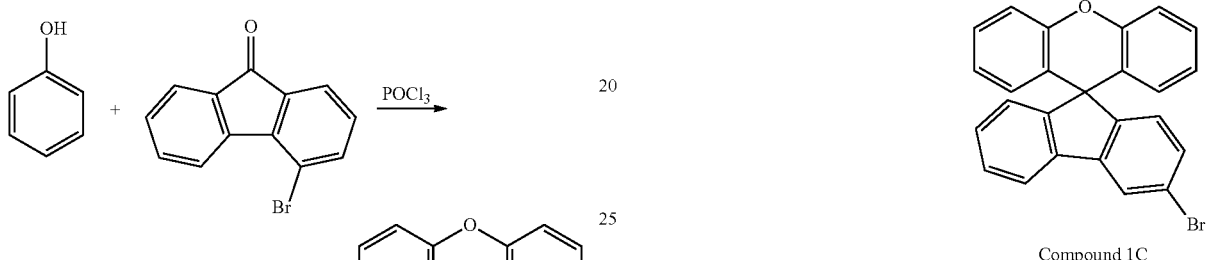

Compound 1B

[Reaction Scheme 2B]

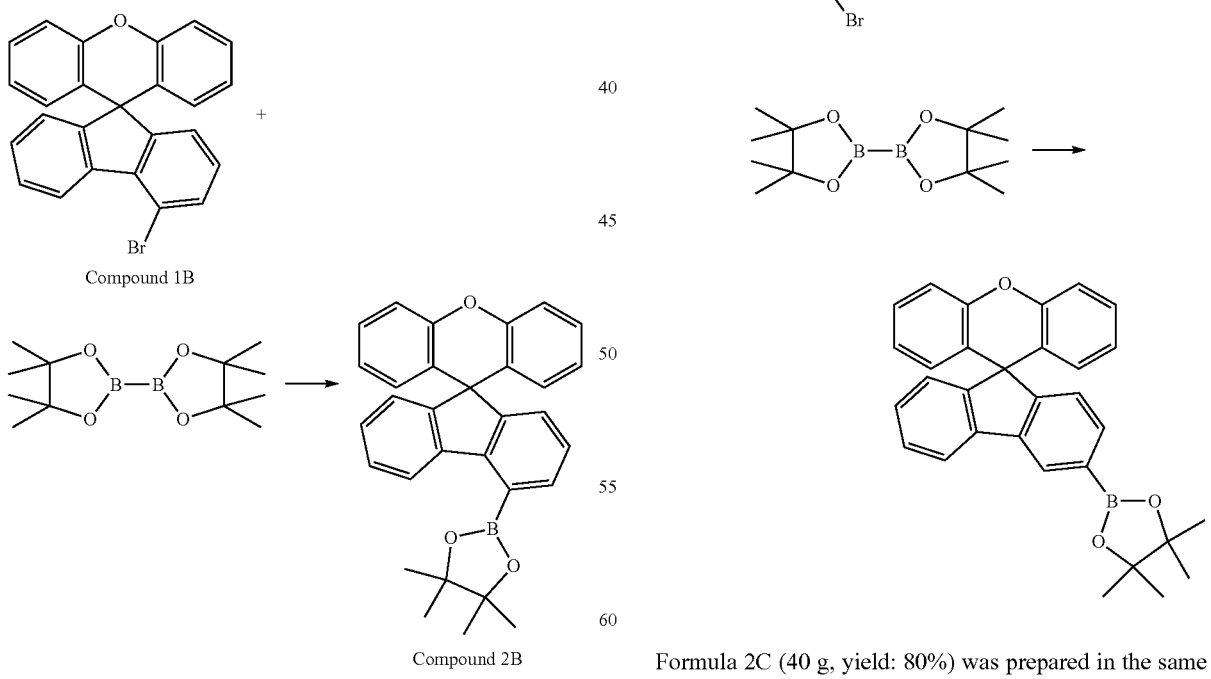

Compound 2B

Formula 2B (40 g, yield: 80%) was prepared in the same manner as in the preparation of Chemical Formula 2A of Synthesis Example 1, except that Compound 1B was used instead of Compound 1A.

MS: [M+H]$^+$=458

(3) Synthesis Example 3: Preparation of the Compound of Chemical Formula 2C

[Reaction Scheme 1C]

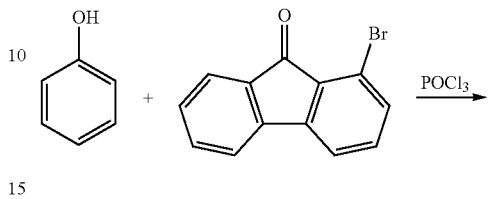

Compound 1C

[Reaction Scheme 2C]

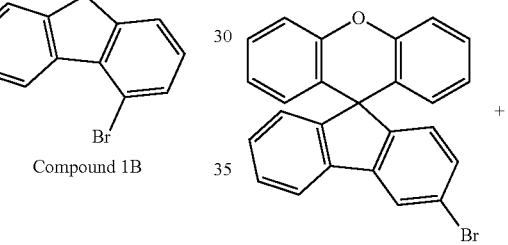

Formula 2C (40 g, yield: 80%) was prepared in the same manner as in the preparation of Chemical Formula 2A of Synthesis Example 1, except that Compound 1C was used instead of Compound 1A.

MS: [M+H]$^+$=458

(4) Synthesis Example 4: Preparation of the Compound of Chemical Formula 2D

[Reaction Scheme 1D]

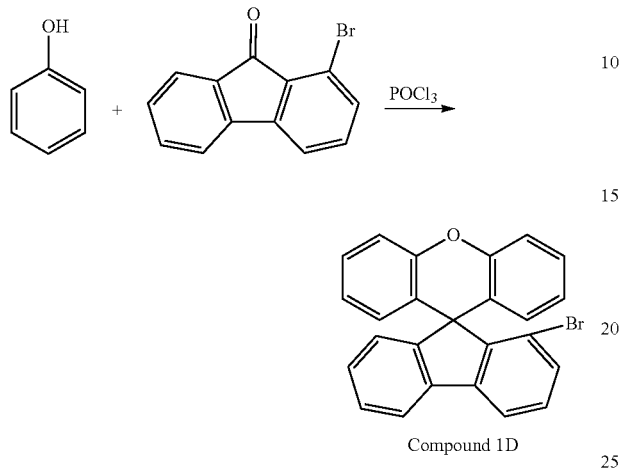

[Reaction Scheme 2D]

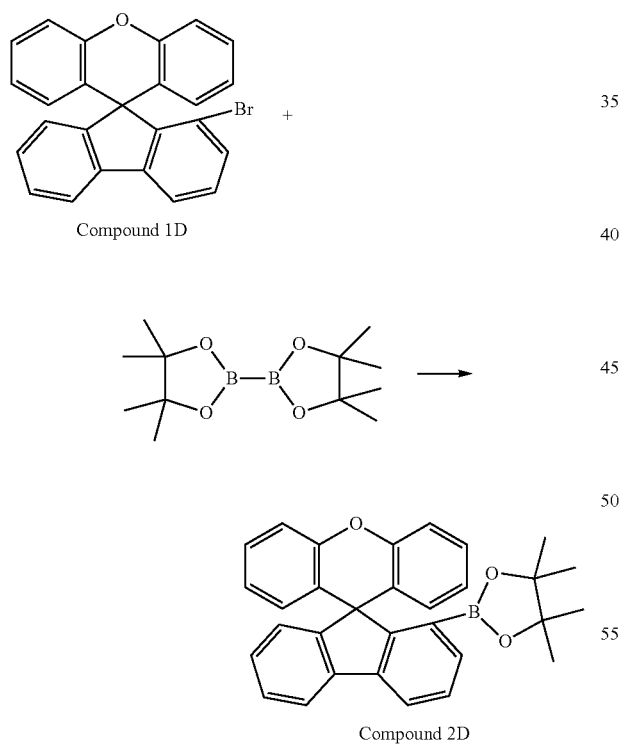

Formula 2D (39 g, yield: 80%) was prepared in the same manner as in the preparation of Chemical Formula 2A of Synthesis Example 1, except that Compound 1D was used instead of Compound 1A.

MS: [M+H]$^+$=458

EXAMPLE (1) Example 1: Preparation of the Compound of Chemical Formula 1-B-1

[Reaction Scheme 1-B-1]

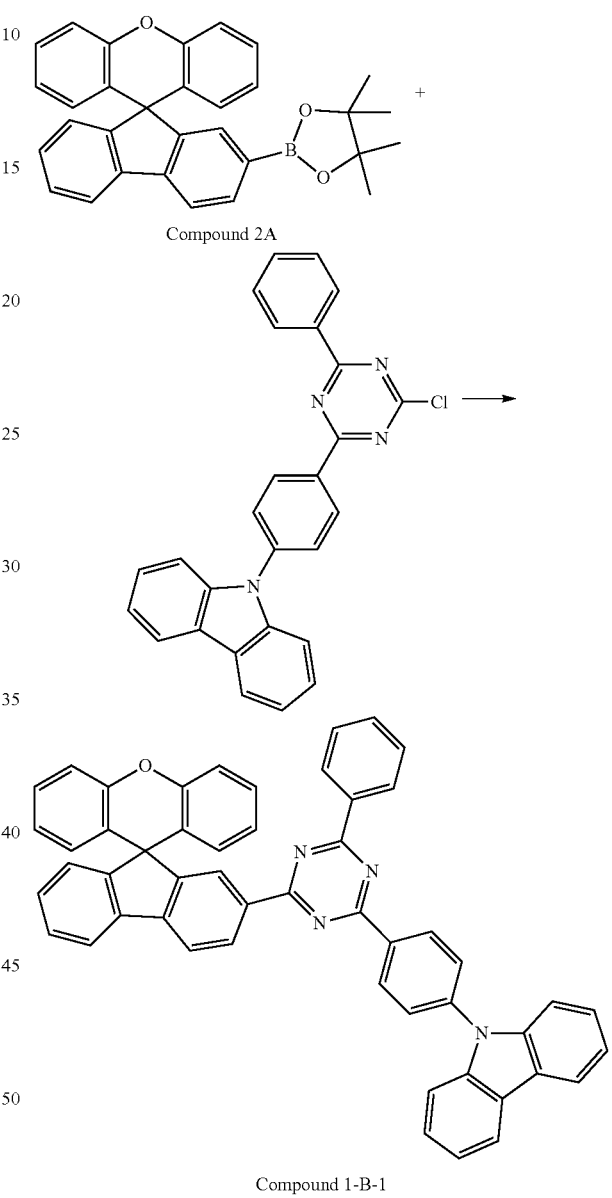

Formula 2A (10 g, 21.8 mmol) and 9-(4-(4-chloro-6-phenyl-1,3,5-triazin-2-yl)phenyl)-9H-carbazole (9.43 g, 21.8 mmol) and potassium carbonate (9 g, 65.4 mmol) were dissolved in tetrahydrofuran (300 ml) and water (100 ml), and them heated to 90° C. Pd(PPh$_3$)$_4$ (0.50 g, 0.44 mmol) was added thereto and then refluxed for 4 hours. After cooling to room temperature, the aqueous layer was removed. Magnesium sulfate was added to the organic layer, followed by filtration. After concentration, the residue was purified by column chromatography to give the compound of Formula 1-B-1 (11 g, yield: 69%).

MS: [M+H]$^+$=728

(2) Example 2: Preparation of the Compound of Chemical Formula 1-B-4

(3) Example 3: Preparation of the Compound of Chemical Formula 1-B-6

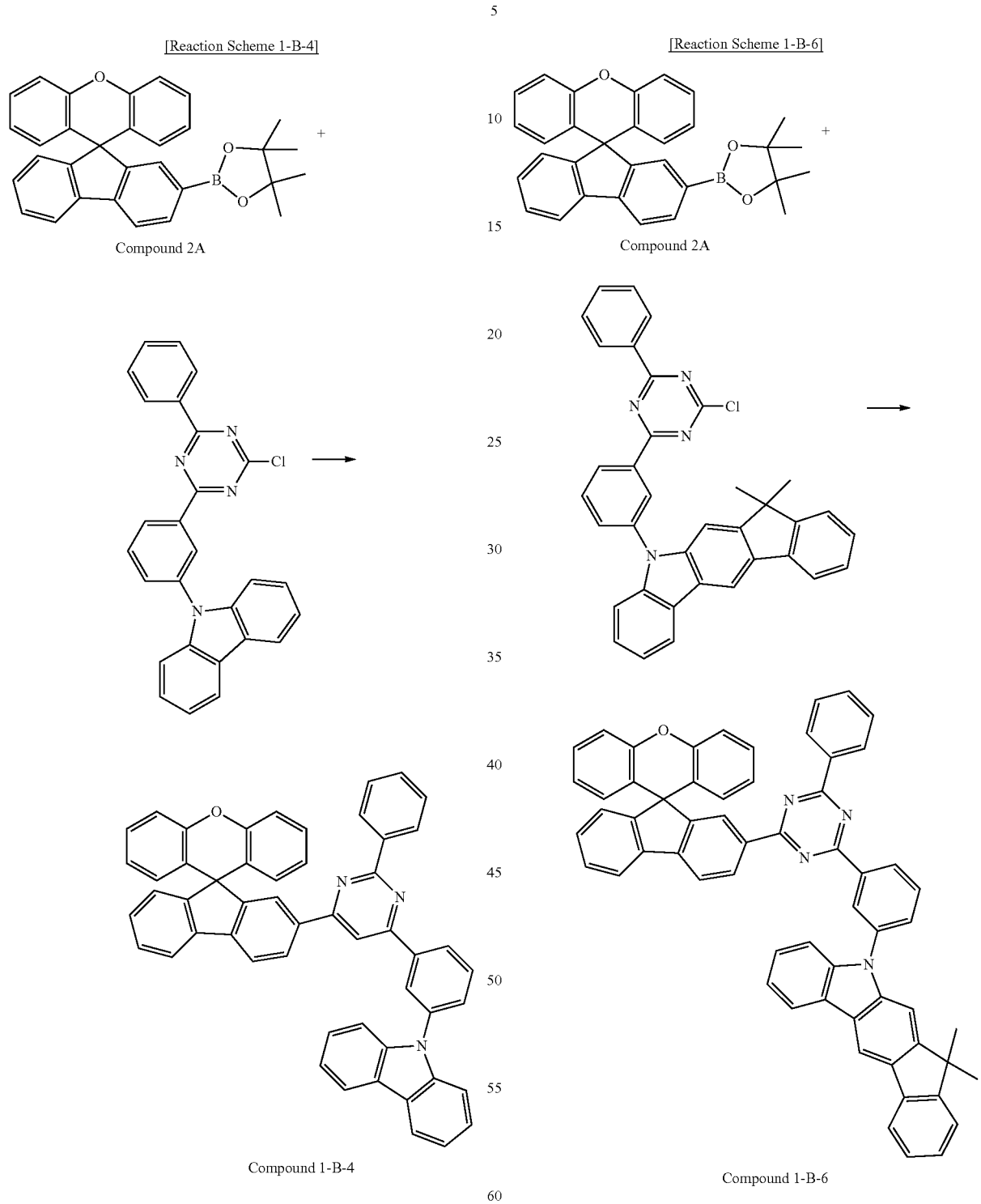

Formula 1-B-4 (12 g, yield: 76%) was prepared in the same manner as in the preparation of Chemical Formula 1-B-1 of Example 1, except that pyrimidine carbazole was used instead of triazine carbazole.

MS: $[M+H]^+=727$

Formula 1-B-6 (15 g, yield: 82%) was prepared in the same manner as in the preparation of Chemical Formula 1-B-1 of Example 1, except that triazinidimethylfluorenecarbazole was used instead of triazine carbazole.

MS: $[M+H]^+=844$ (4) Example 4: Preparation of the Compound of Chemical Formula 1-B-17

[Reaction Scheme 1-B-17]

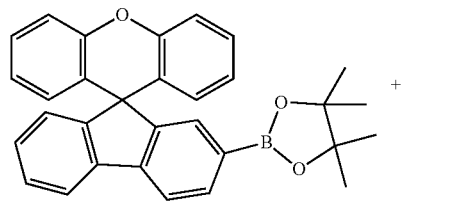

Compound 2A

+

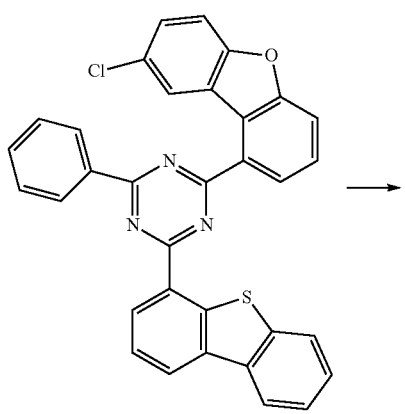

→

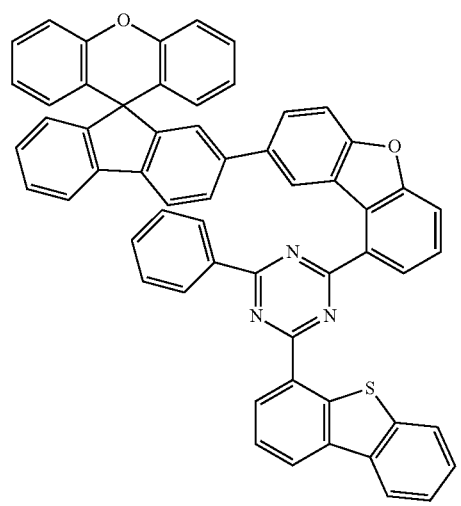

Compound 1-B-17

Formula 1-B-17 (16 g, yield: 88%) was prepared in the same manner as in the preparation of Chemical Formula 1-B-1 of Example 1, except that dibenzofuran-dibenzothiophentriazine was used instead of triazine carbazole.

MS: [M+H]$^+$=835

(5) Example 5: Preparation of the Compound of Chemical Formula 1-B-11

[Reaction Scheme 1-B-11]

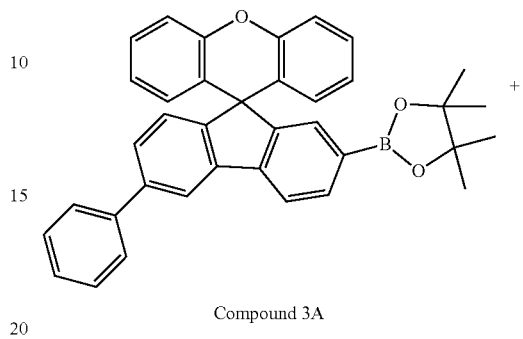

Compound 3A

+

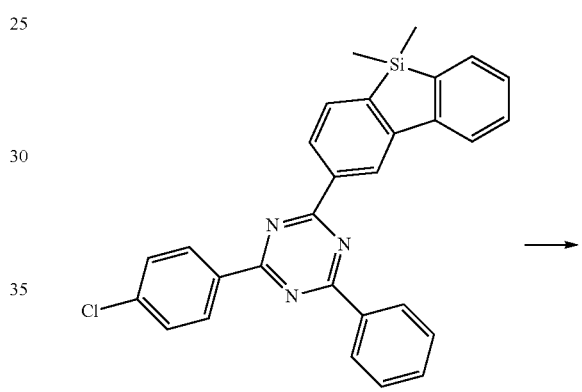

→

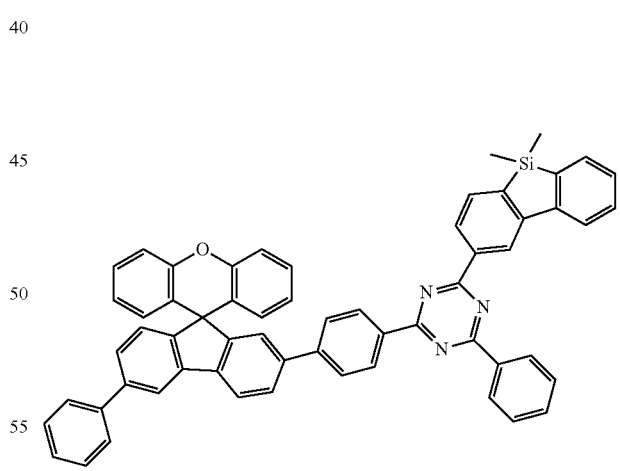

Compound 1-B-11

Formula 1-B-11 (10 g, yield: 54%) was prepared in the same manner as in the preparation of Chemical Formula 1-B-1 of Example 1, except that Formula 3A was used instead of Formula 2A, and dibenzosilane-phenyltriazine was used instead of triazine carbazole.

MS: [M+H]$^+$=847

(6) Example 6: Preparation of the Compound of Chemical Formula 1-B-26

[Reaction Scheme 1-B-26]

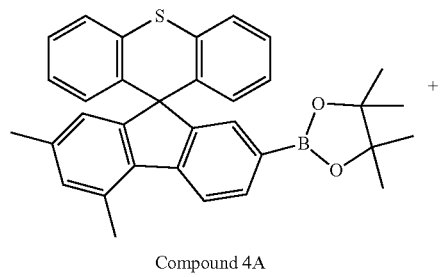

Compound 4A

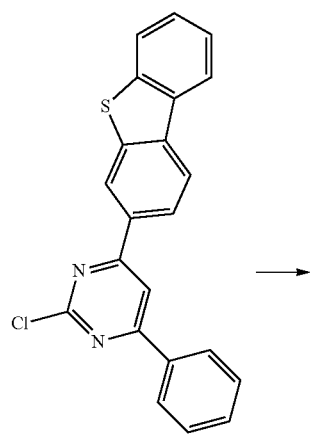

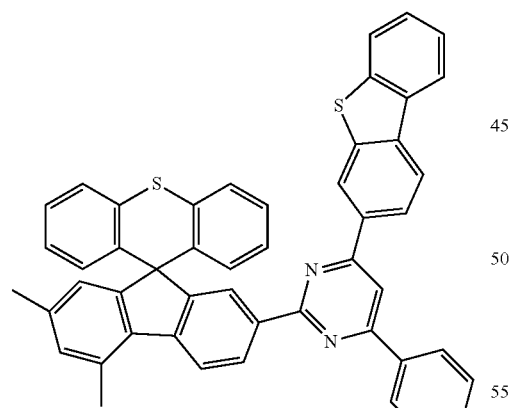

Compound 1-B-26

Formula 1-B-26 (9 g, yield: 58%) was prepared in the same manner as in the preparation of Chemical Formula 1-B-1 of Example 1, except that Formula 4A was used instead of Formula 2A, and dibenzothiophene-phenylpyrimidine was used instead of triazine carbazole.

MS: $[M+H]^+=712$

(7) Example 7: Preparation of the Compound of Chemical Formula 1-B-42

[Reaction Scheme 1-B-42]

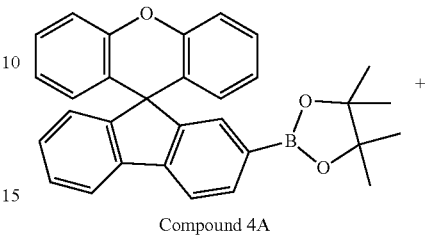

Compound 4A

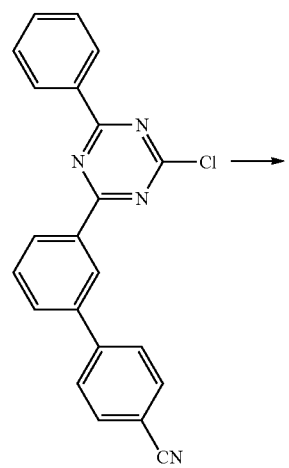

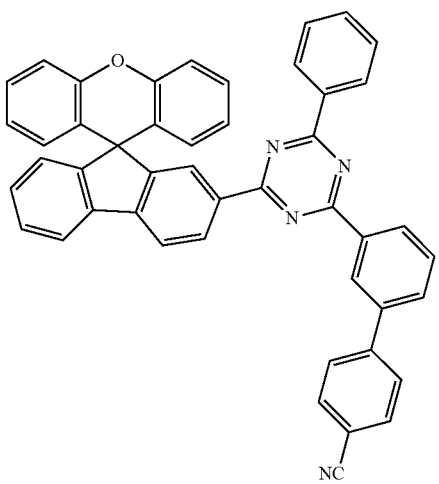

Compound 1-B-42

Formula 1-B-42 (11 g, yield: 76%) was prepared in the same manner as in the preparation of Chemical Formula 1-B-1 of Example 1, except that phenyl cyanotriazine was used instead of triazine carbazole.

MS: $[M+H]^+=664$

83

(8) Example 8: Preparation of the Compound of Chemical Formula 1-B-28

84

(9) Example 9: Preparation of the Compound of Chemical Formula 1-C-9

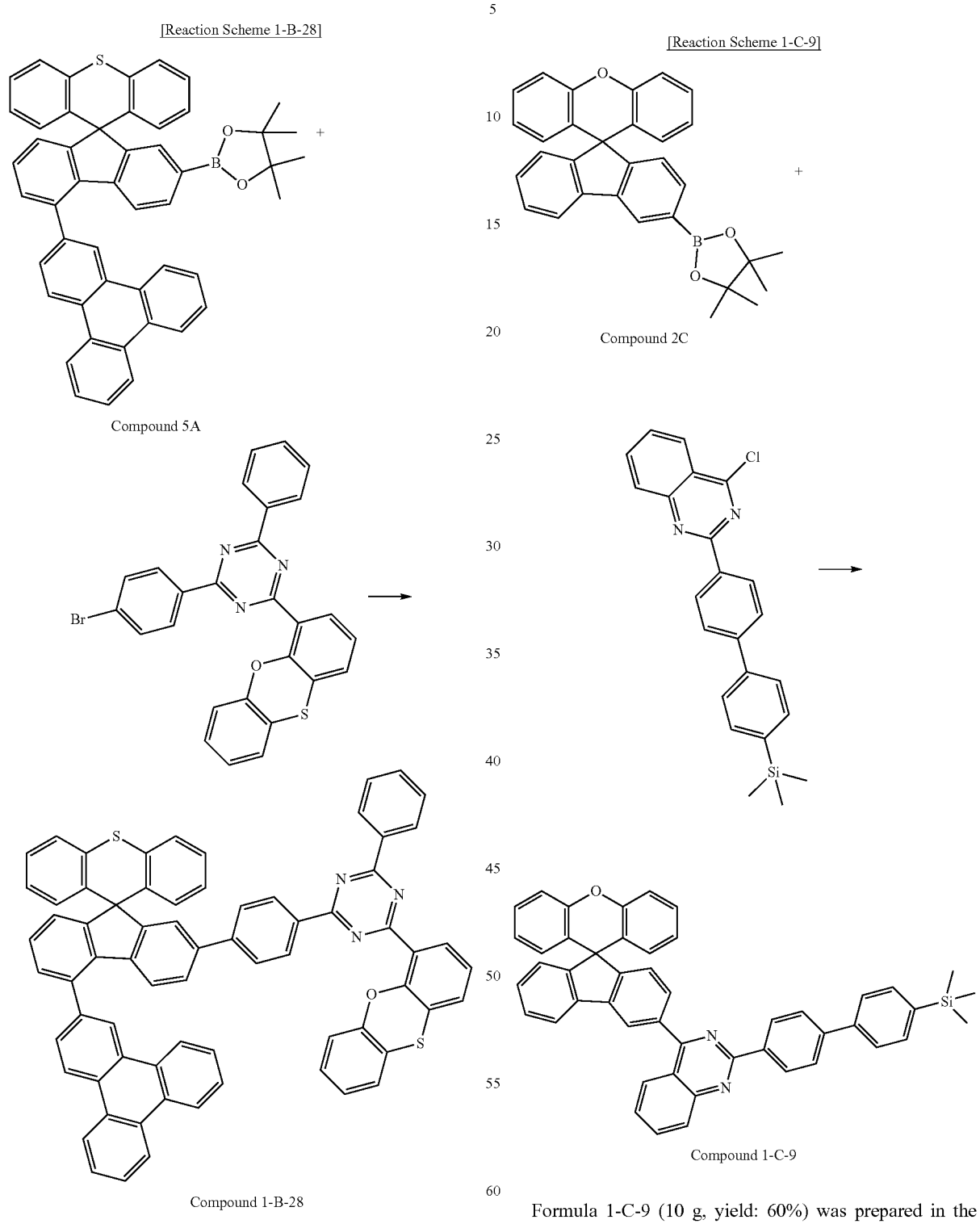

Formula 1-B-28 (10 g, yield: 50%) was prepared in the same manner as in the preparation of Chemical Formula 1-B-1 of Example 1, except that Formula 5A was used instead of Formula 2A, and bromophenyltriazine was used instead of triazine carbazole.

MS: [M+H]$^+$=1003

Formula 1-C-9 (10 g, yield: 60%) was prepared in the same manner as in the preparation of Chemical Formula 1-B-1 of Example 1, except that Formula 2C was used instead of Formula 2A, and trimethylsilyl-quinazoline was used instead of triazine carbazole.

MS: [M+H]$^+$=684

(10) Example 10: Preparation of the Compound of Chemical Formula 1-D-24

[Reaction Scheme 1-D-24]

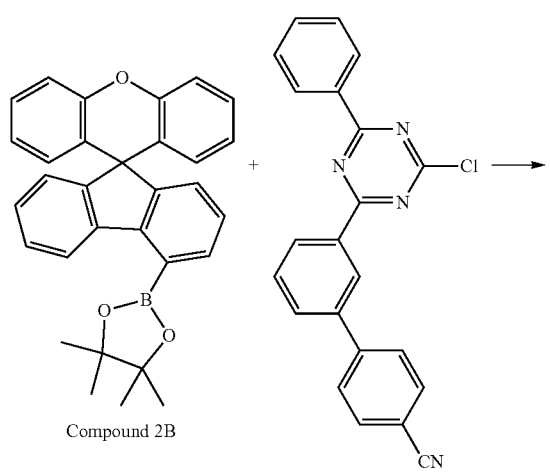

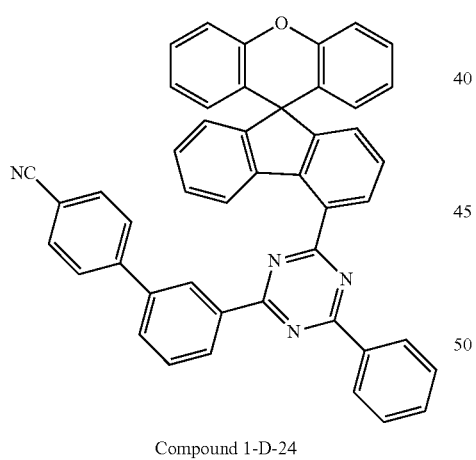

Compound 1-D-24

Formula 1-D-24 (11 g, yield: 76%) was prepared in the same manner as in the preparation of Chemical Formula 1-B-1 of Example 1, except that Formula 2B was used instead of Formula 2A, and phenylcyanotriazine was used instead of triazine carbazole.

MS: $[M+H]^+=664$

(11) Example 11: Preparation of the Compound Represented by Chemical Formula 1-D-21

[Reaction Scheme 1-D-21]

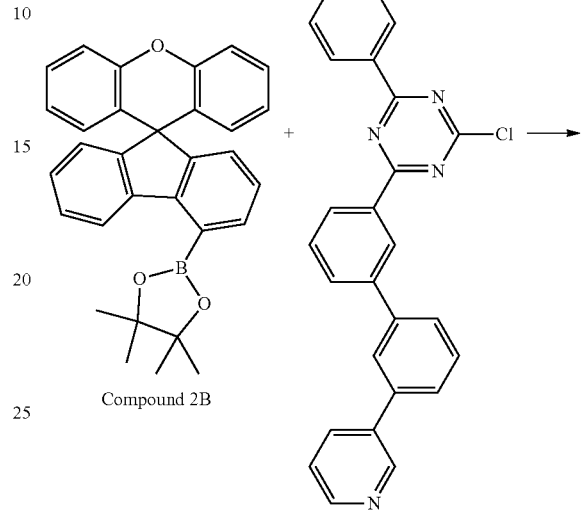

Compound 1-D-21

Formula 1-D-21 (13 g, yield: 83%) was prepared in the same manner as in the preparation of Chemical Formula 1-B-1 of Example 1, except that Formula 2B was used instead of Formula 2A, and phenylpyrimidine triazine was used instead of triazine carbazole.

MS: $[M+H]^+=716$

(12) Example 12: Preparation of Compound Represented by Chemical Formula 1-A-12

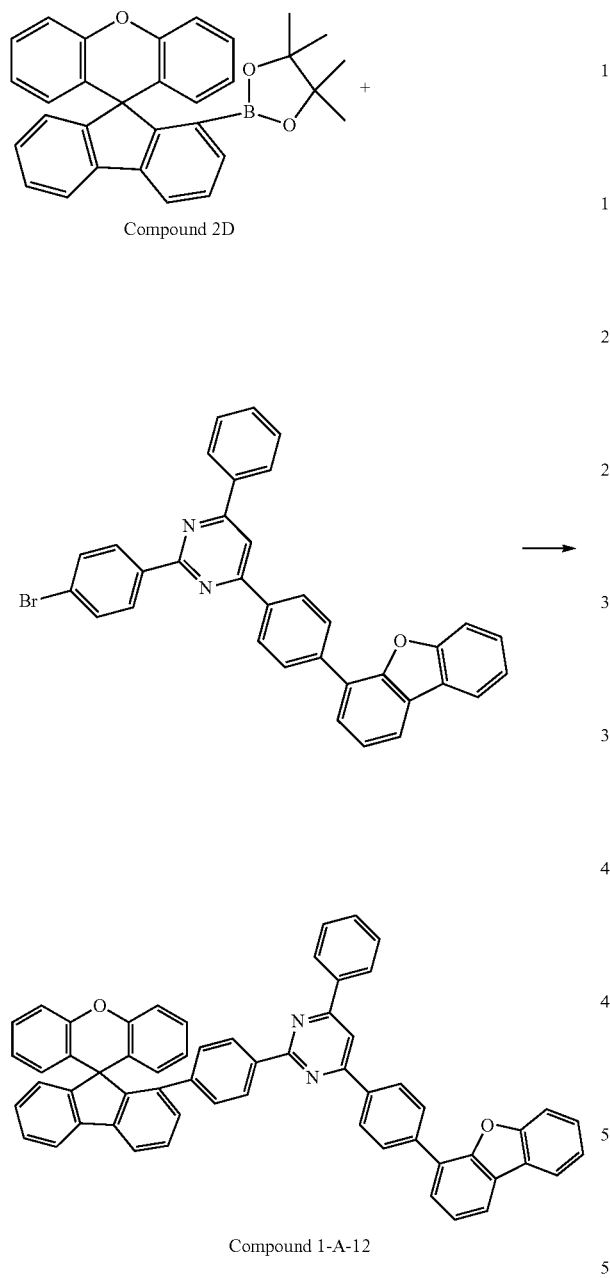

Compound 1-A-12

Formula 1-A-12 (14 g, yield: 80%) was prepared in the same manner as in the preparation of Chemical Formula 1-B-1 of Example 1, except that Formula 2D was used instead of Formula 2A, and dibenzofuran pyrimidine was used instead of triazine carbazole.

MS: $[M+H]^+$=804

(13) Example 13: Preparation of Compound of Chemical Formula 1-D-31

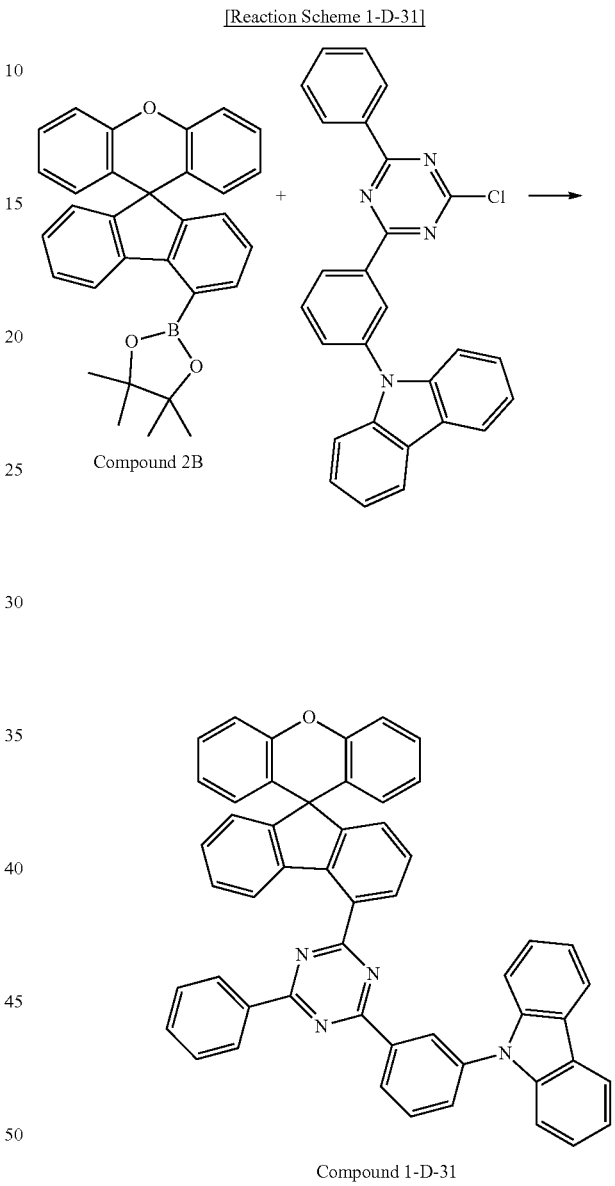

Compound 1-D-31

Formula 1-D-31 (12 g, yield: 76%) was prepared in the same manner as in the preparation of Chemical Formula 1-B-1 of Example 1, except that Formula 2B was used instead of Formula 2A, and 9-(3-(4-chloro-6-phenyl-1,3,5-triazin-2-yl)phenyl)-9H-carbazole was used instead of 9-(4-(4-chloro-6-phenyl-1,3,5-triazin-2-yl)phenyl)-9H-carbazole.

MS: $[M+H]^+$=728

(14) Example 14: Preparation of the Compound of Chemical Formula 1-B-2

[Reaction Scheme 1-B-2]

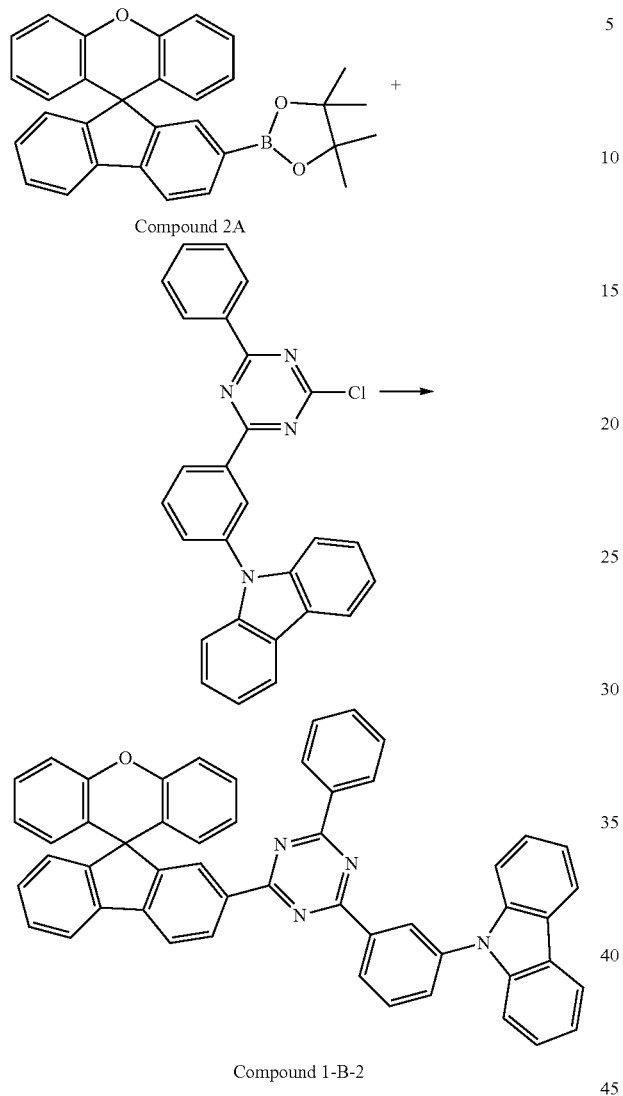

Formula 1-B-2 (13 g, yield: 82%) was prepared in the same manner as in the preparation of Chemical Formula 1-B-1 of Example 1, except that 9-(3-(4-chloro-6-phenyl-1,3,5-triazin-2-yl)phenyl)-9H-carbazole was used instead of 9-(4-(4-chloro-6-phenyl-1,3,5-triazin-2-yl)phenyl)-9H-carbazole.

MS: $[M+H]^+=728$

Experimental Example 1

A glass substrate (Corning 7079) thinly coated with ITO (indium tin oxide) to a thickness of 1,000 Å was put into distilled water in which detergent was dissolved, and then ultrasonically cleaned. A product manufactured by Fischer Co. was used as the detergent, and as the distilled water, distilled water filtered twice using a filter manufactured by Millipore Co. was used. After the ITO was cleaned for 30 minutes, ultrasonic cleaning was repeated twice using distilled water for 10 minutes. After the cleaning with distilled water was completed, the substrate was ultrasonically cleaned in the order of isopropyl alcohol, acetone, and methanol solvent, and then dried.

On the ITO transparent electrode thus prepared, hexanitrile hexaazatriphenylene (HATCN) was thermally vacuum deposited to a thickness of 500 Å to form a hole injection layer. HT1 (400 Å), which is a material for transporting holes, was vacuum-deposited thereon, and then a compound of a host H1 and a dopant D1 was vacuum-deposited to a thickness of 300 Å as a light emitting layer. Formula 1-B-1 prepared in Preparation Example 1, and LiQ (Lithium Quinolate) were vacuum-deposited at a weight ratio of 1:1 on the light emitting layer to form an electron injection and transport layer with a thickness of 350 Å. Lithium fluoride (LiF) and aluminum were sequentially deposited on the electron injection and transport layer to have a thickness of 12 Å and 2,000 Å, respectively, on the electron injection and transport layer, thereby forming a cathode. An organic light emitting device was manufactured.

In the above-mentioned process, the vapor deposition rate of the organic material was maintained at 0.4 to 0.7 Å/sec, the deposition rate of lithium fluoride of the cathode was maintained at 0.3 Å/sec, the deposition rate of aluminum was maintained at 2 Åk/sec, and the degree of vacuum during the deposition was maintained at $2\times10^{-7}$ to $5\times10^{-6}$ torr, thereby manufacturing an organic light emitting device.

[HATCN]

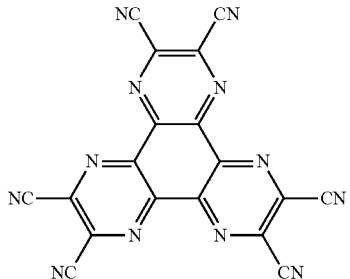

[LiQ]

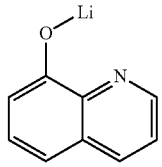

[HT1]

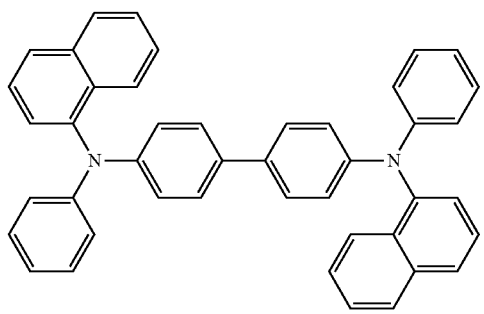

[H1]

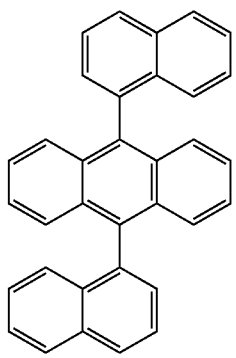

-continued

[D1]
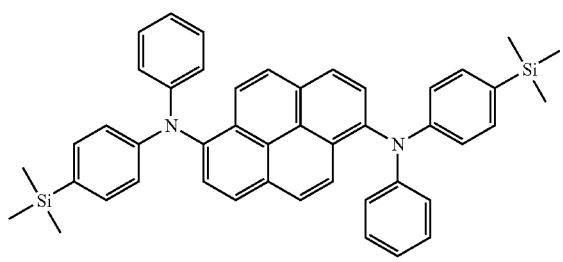

Experimental Examples 2 to 14

The organic light emitting device was manufactured in the same manner as in Experimental Example 1, except that the compounds shown in Table 1 below were used instead of Formula 1-B-1 as an electron transport layer in Example 1.

Comparative Experimental Examples 1 to 7

The organic light emitting device was manufactured in the same manner as in Experimental Example 1, except that the compounds of Formulae ET1 to ET7 below were used instead of Formula 1-B-1 as an electron transport layer in Experimental Example 1.

[ET1]
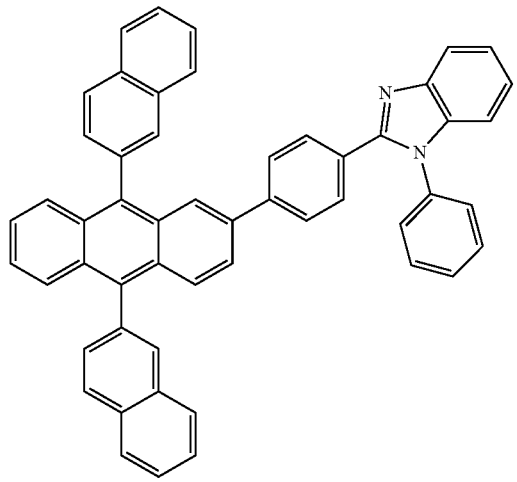

[ET2]
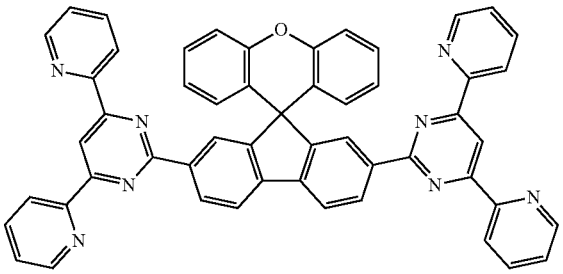

[ET3]
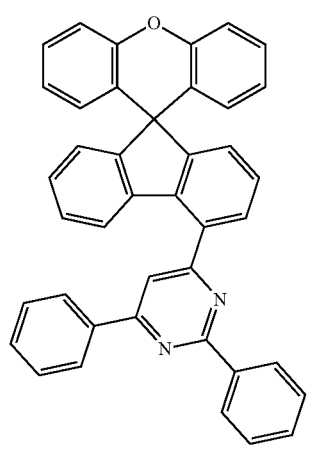

[ET4]
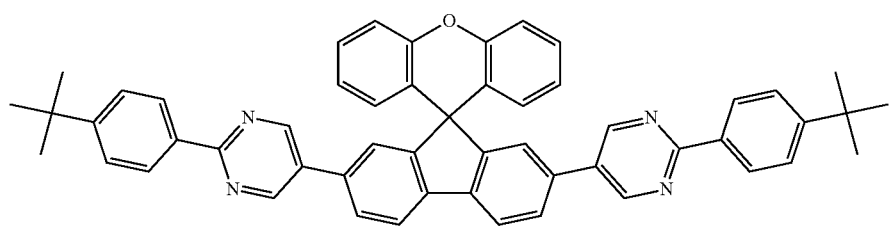

[ET5]

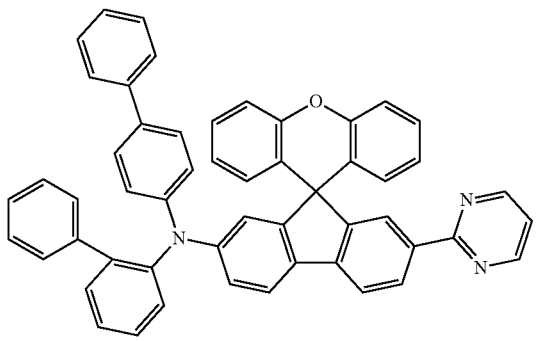

[ET6]

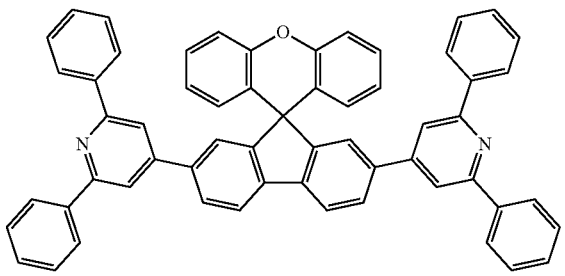

[ET7]

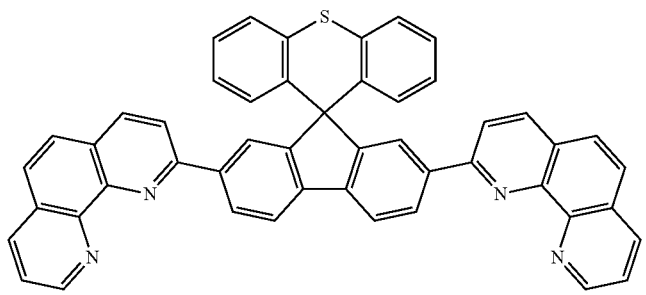

For the organic light emitting devices manufactured using the respective compounds as the electron transport material as in Experimental Examples 1 to 14 and Comparative Experimental Examples 1 to 7, the driving voltage and the light emitting efficiency were measured at a current density of 10 mA/cm$^2$, and the time (LT98) required for the luminance to be reduced to 98% of the initial luminance was measured at a current density of 20 mA/cm$^2$. The results are shown in Table 1 below.

TABLE 1

| Category | Example Compound | Voltage (V) | Current efficiency (cd/A) | Color coordinate (x, y) | Life Time 98 at 20 mA/cm$^2$ |
|---|---|---|---|---|---|
| Experimental Example 1 | Formula 1-B-1 | 3.81 | 5.29 | (0.137, 0.124) | 55 |
| Experimental Example 2 | Formula 1-B-4 | 3.87 | 5.31 | (0.139, 0.127) | 48 |
| Experimental Example 3 | Formula 1-B-6 | 3.71 | 5.49 | (0.138, 0.126) | 42 |
| Experimental Example 4 | Formula 1-B-17 | 3.89 | 5.25 | (0.138, 0.128) | 57 |
| Experimental Example 5 | Formula 1-B-11 | 3.79 | 5.50 | (0.137, 0.126) | 41 |
| Experimental Example 6 | Formula 1-B-26 | 3.88 | 5.30 | (0.137, 0.124) | 42 |
| Experimental Example 7 | Formula 1-B-42 | 3.98 | 5.21 | (0.137, 0.125) | 59 |
| Experimental Example 8 | Formula 1-B-28 | 3.99 | 5.51 | (0.137, 0.126) | 49 |
| Experimental Example 9 | Formula 1-C-9 | 4.02 | 5.22 | (0.137, 0.126) | 51 |
| Experimental Example 10 | Formula 1-D-24 | 3.99 | 5.20 | (0.137, 0.126) | 60 |
| Experimental Example 11 | Formula 1-D-21 | 3.90 | 5.30 | (0.137, 0.126) | 53 |
| Experimental Example 12 | Formula 1-A-12 | 4.01 | 5.34 | (0.137, 0.126) | 44 |
| Experimental Example 13 | Formula 1-D-31 | 3.80 | 5.31 | (0.137, 0.126) | 65 |
| Experimental Example 14 | Formula 1-B-2 | 3.79 | 5.34 | (0.137, 0.125) | 62 |
| Comparative Experimental Example 1 | ET1 | 4.05 | 5.01 | (0.140, 0.129) | 28 |
| Comparative Experimental Example 2 | ET2 | 4.10 | 4.90 | (0.140, 0.127) | 37 |
| Comparative Experimental Example 3 | ET3 | 4.21 | 4.91 | (0.139, 0.129) | 36 |
| Comparative Experimental Example 4 | ET4 | 4.09 | 4.65 | (0.140, 0.126) | 21 |
| Comparative Experimental Example 5 | ET5 | 5.15 | 4.23 | (0.139, 0.127) | 5 |
| Comparative Experimental Example 6 | ET6 | 4.51 | 4.55 | (0.140, 0.129) | 37 |
| Comparative Experimental Example 7 | ET7 | 4.22 | 4.87 | (0.139, 0.128) | 31 |

As can be seen from the experimental data of Table 1 above, it was confirmed that the organic light emitting device using the compound of Chemical Formula 1 according to the present invention exhibited excellent characteristics in terms of efficiency, driving voltage and/or stability.

The compound according to the present invention is an asymmetric compound containing a substituent of triazine (or pyrimidine) on only one side of the core structure, and has a low crystallinity compared to Comparative Experimental Examples using a compound having a symmetric structure, and therefore, a dense film quality was formed during film formation, and the lifetime improving effect was remarkably improved.

| <Description of symbols> | |
|---|---|
| 1: substrate | 2: anode |
| 3: light emitting layer | |
| 4: cathode | |
| 5: hole injection layer | |
| 6: hole transport layer | |
| 7: light emitting layer | |
| 8: electron transport layer | |

What is claimed is:

1. A compound of Chemical Formula 1:

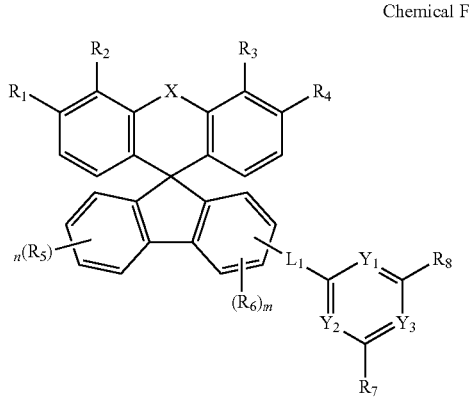

Chemical Formula 1 wherein, in Chemical Formula 1:
X is O or S,
$Y_1$, $Y_2$ and $Y_3$ are each independently N or CR', with the proviso that at least one of them is N;
R' is hydrogen, or is combined with adjacent $R_7$ and $R_8$ to form a substituted or unsubstituted $C_{6-60}$ aryl;
$R_1$, $R_2$, $R_3$ and $R_4$ are each independently hydrogen, deuterium, a substituted or unsubstituted $C_{1-60}$ alkyl, or a substituted or unsubstituted $C_{6-60}$ aryl, or they can be combined with adjacent substituents to form a substituted or unsubstituted benzene ring;
$R_5$ and $R_6$ are each independently hydrogen, deuterium, a substituted or unsubstituted $C_{1-60}$ alkyl, or a substituted or unsubstituted $C_{6-60}$ aryl;
n is an integer of 1 to 4;
m is an integer of 1 to 3;
$L_1$ is a direct bond, a substituted or unsubstituted $C_{6-60}$ arylene, or a substituted or unsubstituted $C_{5-60}$ heteroarylene containing one or more heteroatoms selected from the group consisting of O and S;
$R_7$ and $R_8$ are each independently a substituted or unsubstituted $C_{6-60}$ aryl, a substituted or unsubstituted silyl, or a substituted or unsubstituted $C_{5-60}$ heteroaryl containing one or more heteroatoms selected from the group consisting of N, O, S and Si;
with the proviso that at least one of $R_7$ and $R_8$ is a compound of Chemical Formula 2:
[Chemical Formula 2]
*-(L2-Het)
wherein, in Chemical Formula 2:
$L_2$ is a direct bond, a substituted or unsubstituted $C_{6-60}$ arylene, or a substituted or unsubstituted $C_{5-60}$ heteroarylene containing one or more heteroatoms selected from the group consisting of N, O and S; and Het is any one selected from the group consisting of the following Chemical Formulae [1-1] to [1-31]:

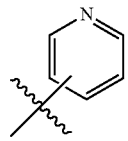

[1-1]

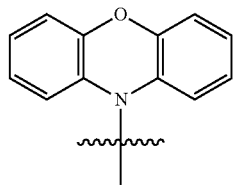

[1-2]

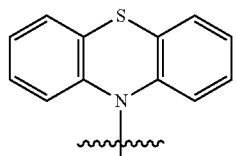

[1-3]

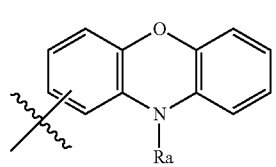

[1-4]

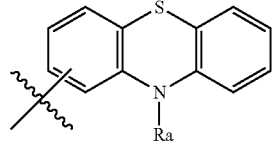

[1-5]

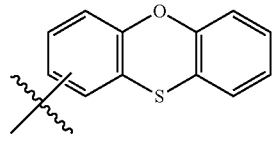

[1-6]

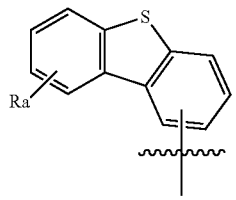

[1-7]

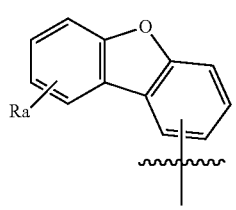

[1-8]

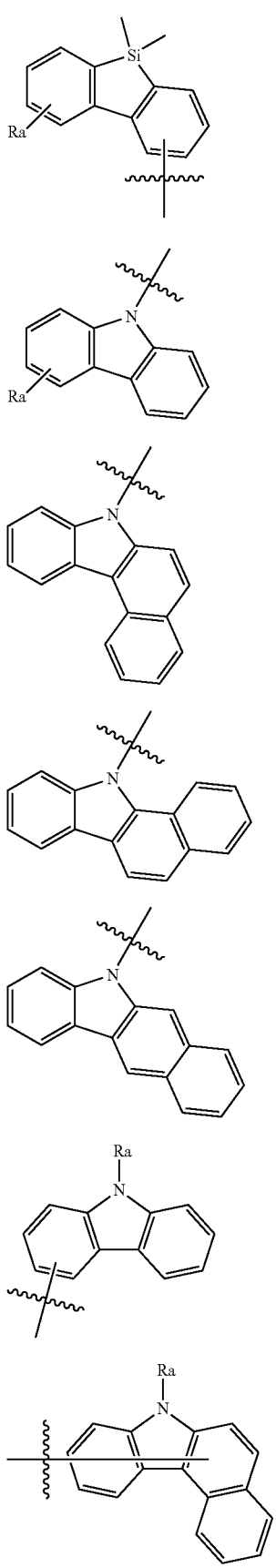
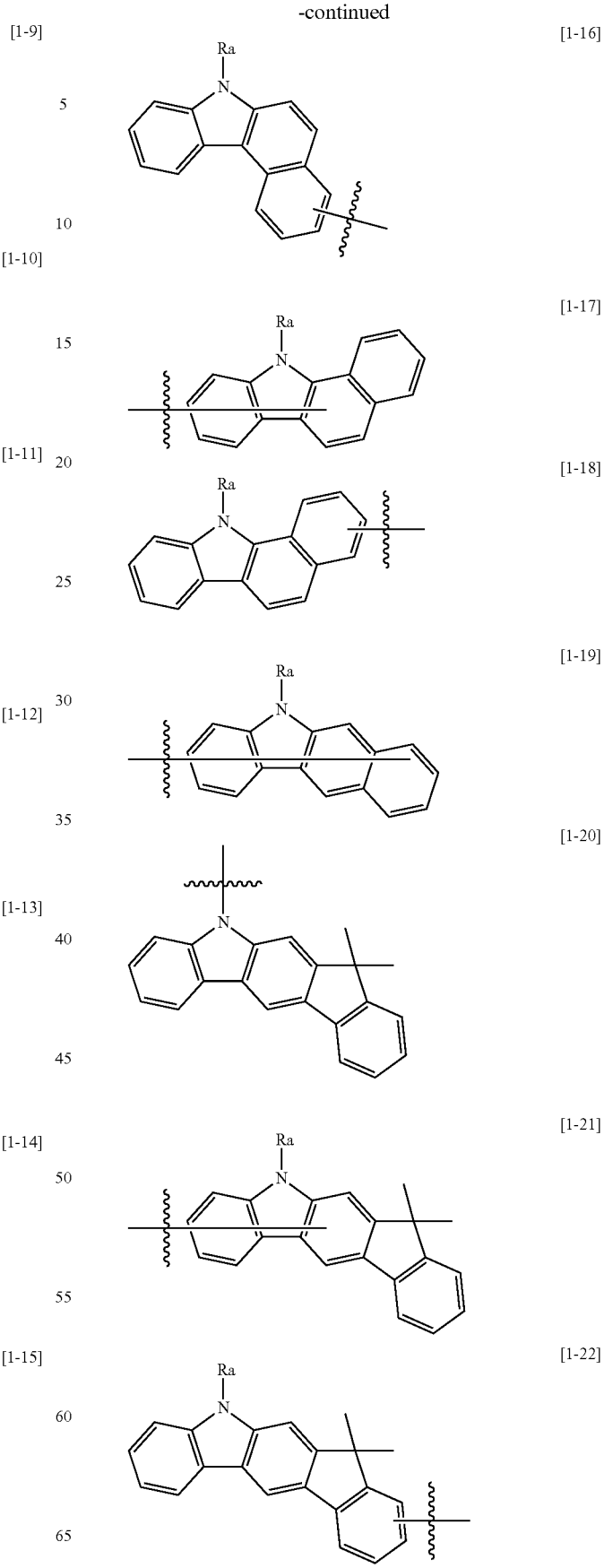

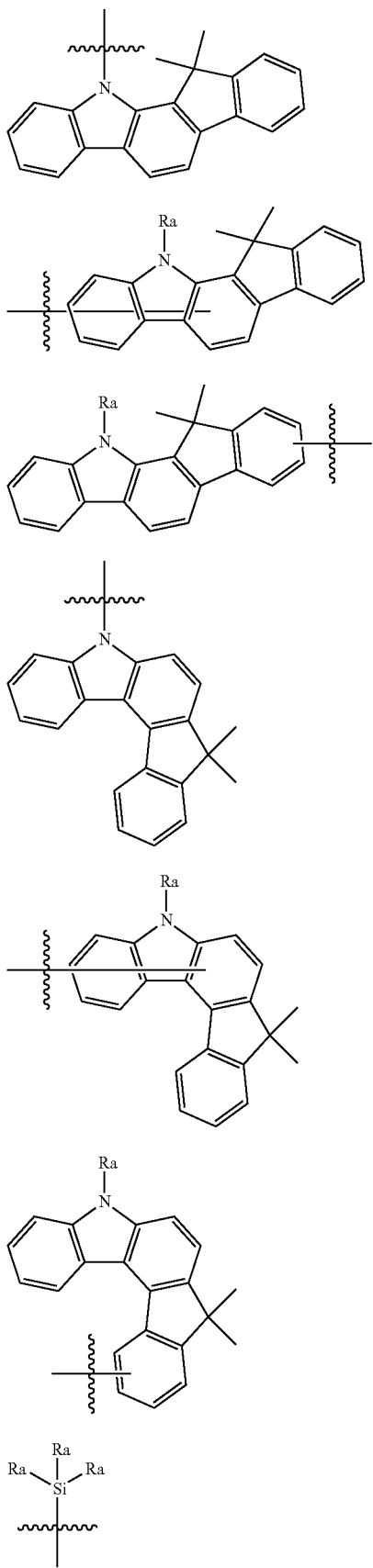
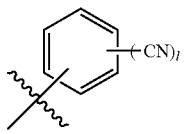
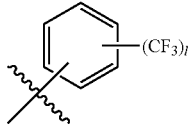
wherein, in Chemical Formulae [1-1] to [1-31]:
 each Ra is independently hydrogen, a substituted or unsubstituted $C_{1-60}$ alkyl, or a substituted or unsubstituted $C_{6-60}$ aryl, and
 each l is independently an integer of 1 to 4.
2. A compound of any one of Chemical Formulae 5 to 9:
[Chemical Formula 5]
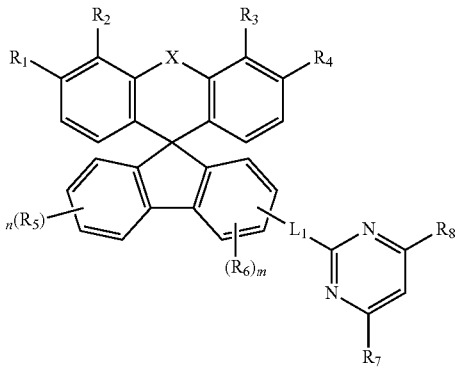
[Chemical Formula 6]
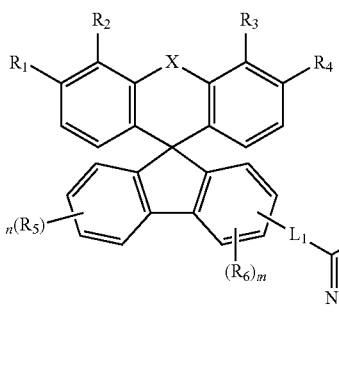
[Chemical Formula 7]
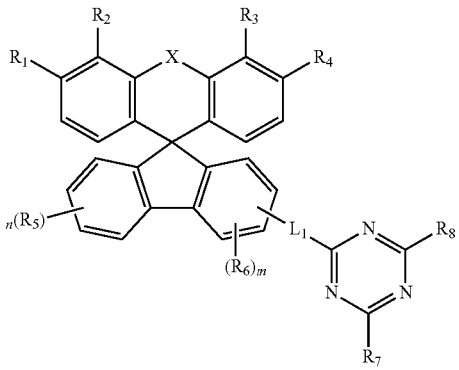

-continued

[Chemical Formula 8]

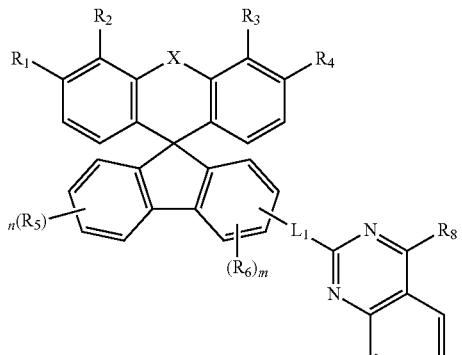

[Chemical Formula 9]

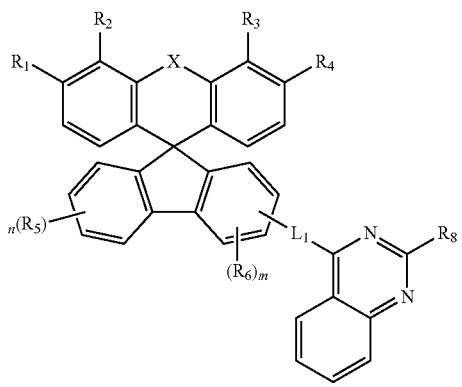

wherein, in Chemical Formulae 5 to 9:
X is O or S,
$R_1$, $R_2$, $R_3$ and $R_4$ are each independently hydrogen, deuterium, a substituted or unsubstituted $C_{1-60}$ alkyl, or a substituted or unsubstituted $C_{6-60}$ aryl, or they can be combined with adjacent substituents to form a substituted or unsubstituted benzene ring;
$R_5$ and $R_6$ are each independently hydrogen, deuterium, a substituted or unsubstituted $C_{1-60}$ alkyl, or a substituted or unsubstituted $C_{6-60}$ aryl;
n is an integer of 1 to 4;
m is an integer of 1 to 3;
$L_1$ is a direct bond, a substituted or unsubstituted $C_{6-60}$ arylene, or a substituted or unsubstituted $C_{5-60}$ heteroarylene containing one or more heteroatoms selected from the group consisting of N, O and S;
$R_7$ and $R_8$ are each independently a substituted or unsubstituted $C_{6-60}$ aryl, a substituted or unsubstituted silyl, or a substituted or unsubstituted $C_{5-60}$ heteroaryl containing one or more heteroatoms selected from the group consisting of N, O, S and Si, with the proviso that at least one of $R_7$ and $R_8$ in Chemical Formulas 5-7 is a compound of Chemical Formula 2 and with the proviso that in Chemical Formulas 8 and 9, $R_8$ is a compound of Chemical Formula 2:
[Chemical Formula 2]
*-($L_2$-Het)
wherein, in Chemical Formula 2:
$L_2$ is a direct bond, a substituted or unsubstituted $C_{6-60}$ arylene, or a substituted or unsubstituted $C_{5-60}$ heteroarylene containing one or more heteroatoms selected from the group consisting of N, O and S; and Het is any one selected from the group consisting of the following Chemical Formulae [1-1] to [1-31]:

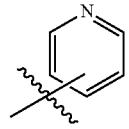
[1-1]

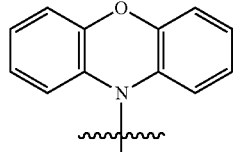
[1-2]

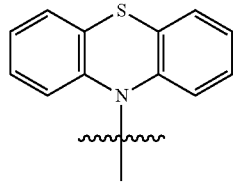
[1-3]

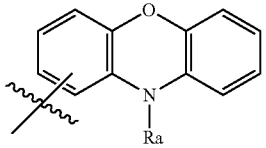
[1-4]

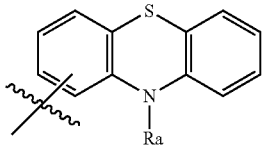
[1-5]

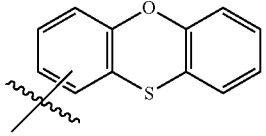
[1-6]

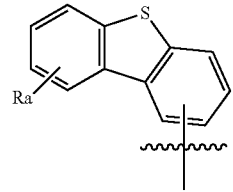
[1-7]

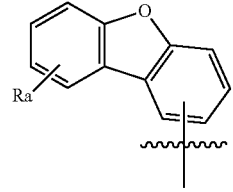
[1-8]

[1-9] 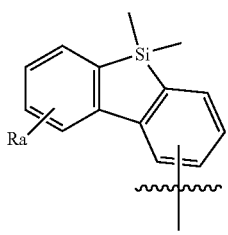
[1-10] 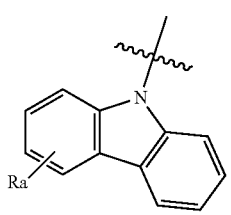
[1-11] 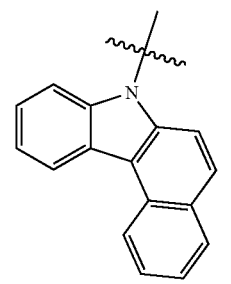
[1-12] 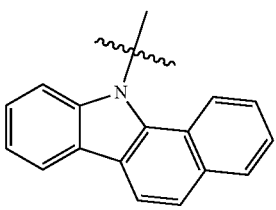
[1-13] 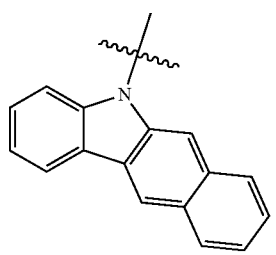
[1-14] 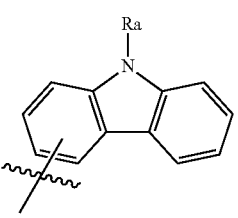
[1-15] 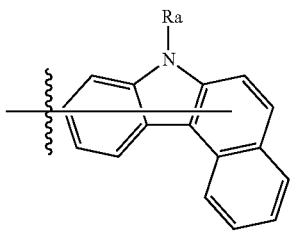
[1-16] 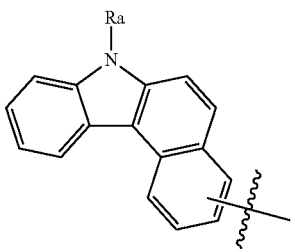
[1-17] 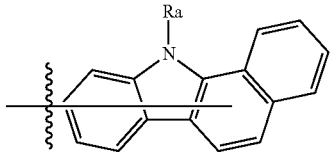
[1-18] 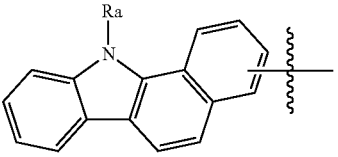
[1-19] 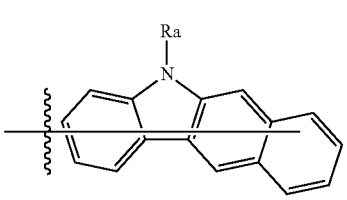
[1-20] 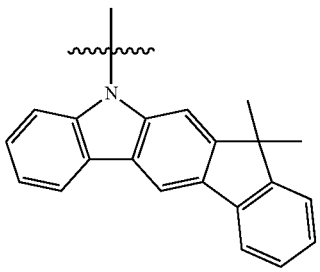
[1-21] 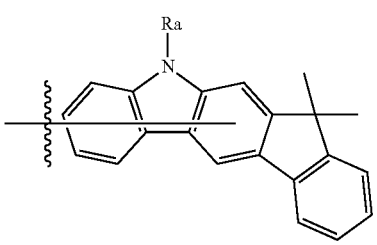

[1-22]
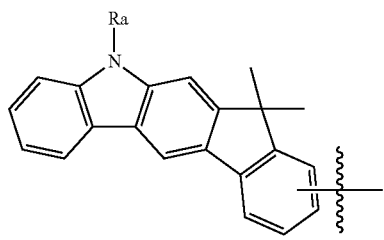
[1-23]
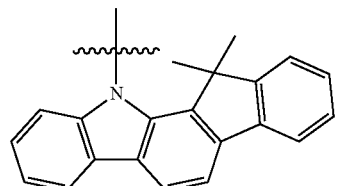
[1-24]
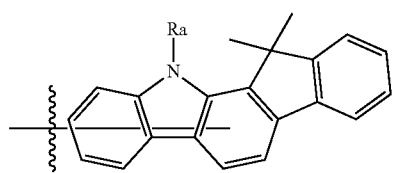
[1-25]
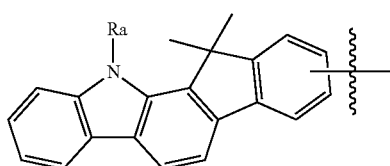
[1-26]
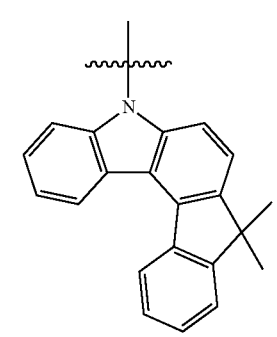
[1-27]
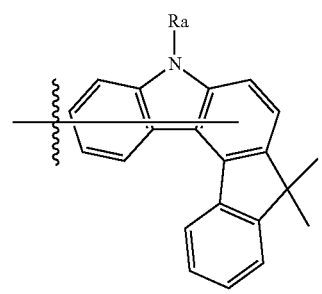
[1-28]
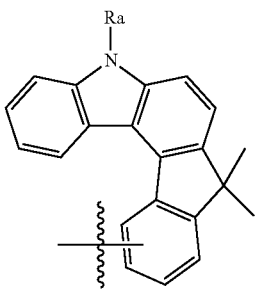
[1-29]
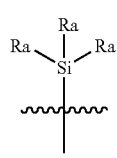
[1-30]
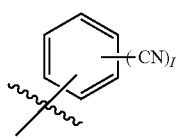
[1-31]
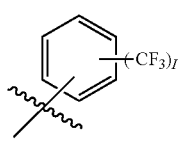
wherein, in Chemical Formulae [1-1] to [1-31]:
  each Ra is independently hydrogen, a substituted or unsubstituted $C_{1-60}$ alkyl, or a substituted or unsubstituted $C_{6-60}$ aryl, and
  each l is independently an integer of 1 to 4.
3. A compound of any one of Chemical Formulas 10 to 12:
[Chemical Formula 10]
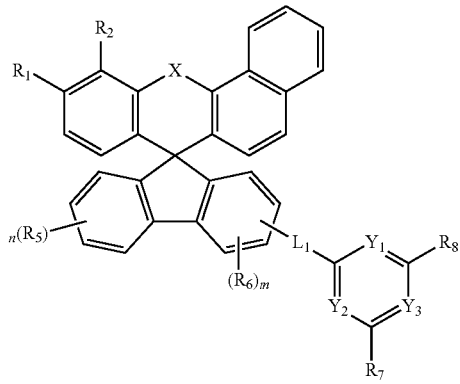

[Chemical Formula 11]

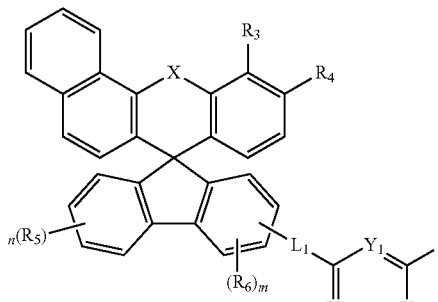

[Chemical Formula 12]

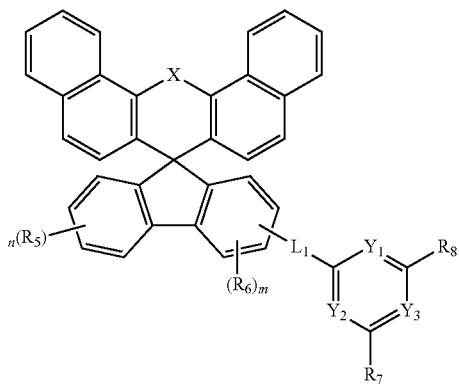

wherein, in Chemical Formulae 10 to 12:

X is O or S, $Y_1$, $Y_2$ and $Y_3$ are each independently N or CR', with the proviso that at least one of them is N;

R' is hydrogen, or is combined with adjacent $R_7$ and $R_8$ to form a substituted or unsubstituted $C_{6-60}$ aryl;

$R_1$, $R_2$, $R_3$ and $R_4$ are each independently hydrogen, deuterium, a substituted or unsubstituted $C_{1-60}$ alkyl, or a substituted or unsubstituted $C_{6-60}$ aryl, and $R_1$ and $R_2$ in Chemical Formula 10, and $R_3$ and $R_4$ in Chemical Formula 11 do not combine with an adjacent substituent to form a substituted or unsubstituted benzene ring;

$R_5$ and $R_6$ are each independently hydrogen, deuterium, a substituted or unsubstituted $C_{1-60}$ alkyl, or a substituted or unsubstituted $C_{6-60}$ aryl;

n is an integer of 1 to 4;

$L_1$ is a direct bond, a substituted or unsubstituted $C_{6-60}$ arylene, or a substituted or unsubstituted $C_{5-60}$ heteroarylene containing one or more heteroatoms selected from the group consisting of O and S;

$R_7$ and $R_8$ are each independently a substituted or unsubstituted $C_{6-60}$ aryl, a substituted or unsubstituted silyl, or a substituted or unsubstituted $C_{5-60}$ heteroaryl containing one or more heteroatoms selected from the group consisting of N, O, S and Si;

with the proviso that at least one of $R_7$ and $R_8$ is a compound of Chemical Formula 2:

[Chemical Formula 2]

*-($L_2$-Het)

wherein, in Chemical Formula 2:

$L_2$ is a direct bond, a substituted or unsubstituted $C_{6-60}$ arylene, or a substituted or unsubstituted $C_{5-60}$ heteroarylene containing one or more heteroatoms selected from the group consisting of N, O and S; and Het is any one selected from the group consisting of the following Chemical Formulae [1-1] to [1-31]:

[1-1]

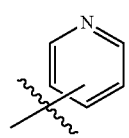

[1-2]

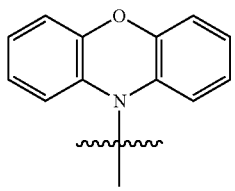

[1-3]

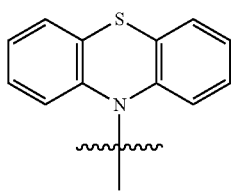

[1-4]

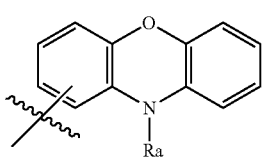

[1-5]

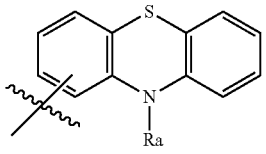

[1-6]

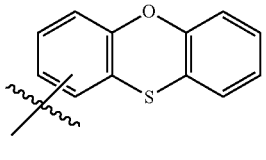

[1-7]

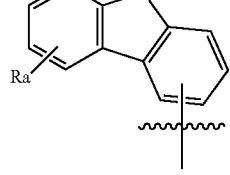

[1-8]

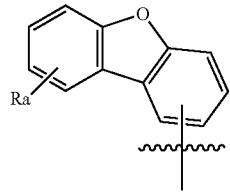

[1-9]
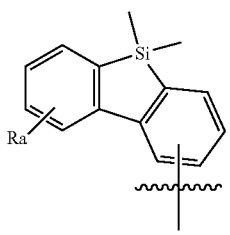
[1-10]
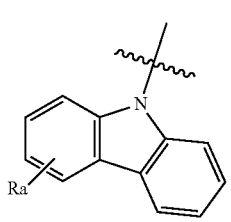
[1-11]
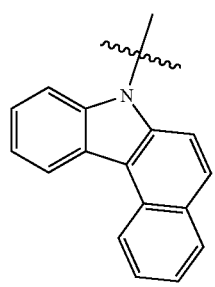
[1-12]
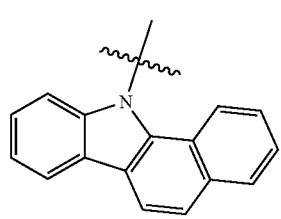
[1-13]
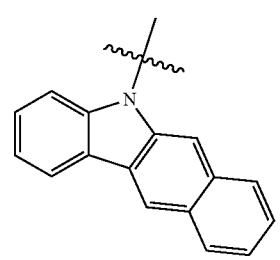
[1-14]
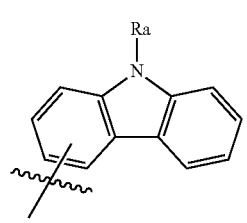
[1-15]
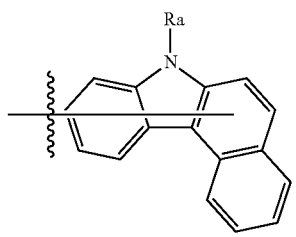
[1-16]
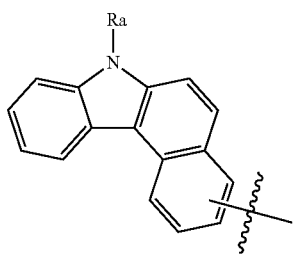
[1-17]
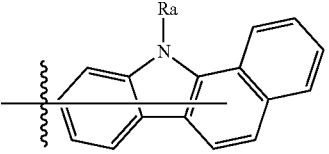
[1-18]
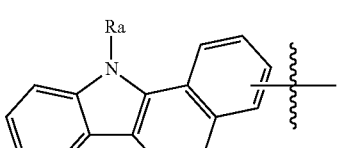
[1-19]
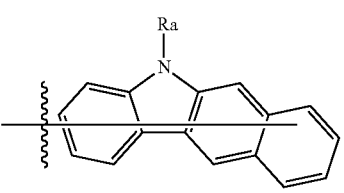
[1-20]
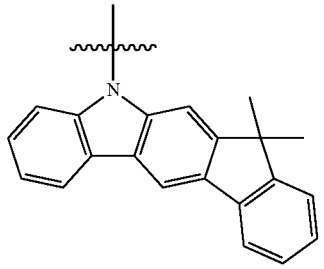
[1-21]
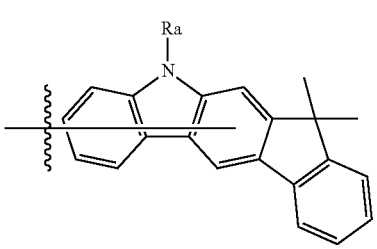

[1-22]
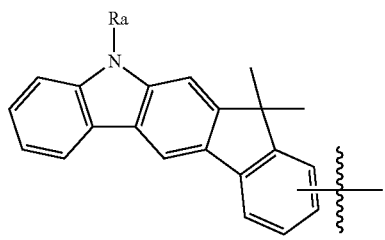
[1-23]
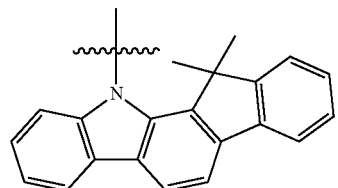
[1-24]
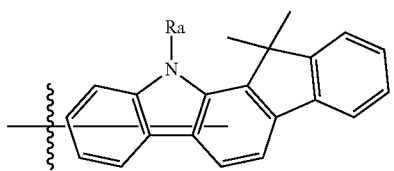
[1-25]
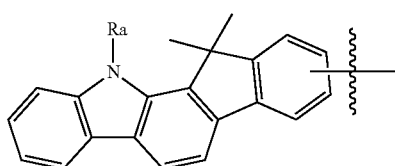
[1-26]
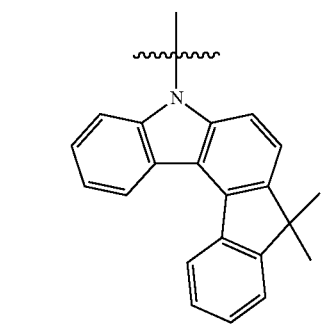
[1-27]
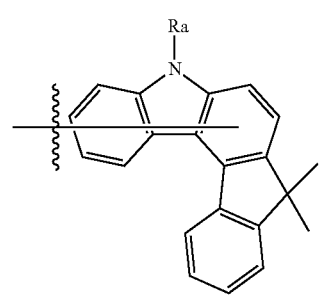
[1-28]
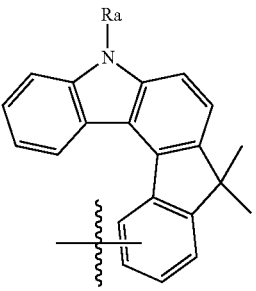
[1-29]
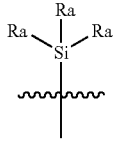
[1-30]
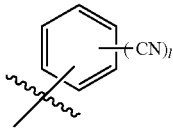
[1-31]
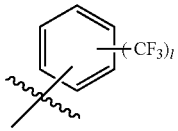
wherein, in Chemical Formulae [1-1] to [1-31]:
each Ra is independently hydrogen a substituted or unsubstituted $C_{1-60}$ alkyl, or a substituted or unsubstituted $C_{6-60}$ aryl, and
each l is independently an integer of 1 to 4.
4. The compound according to claim 1, wherein $R_1$, $R_2$, $R_3$ and $R_4$ are each independently hydrogen, a methyl group, an ethyl group, a propyl group,
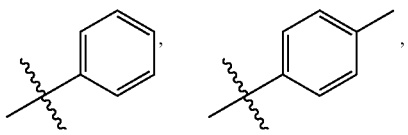
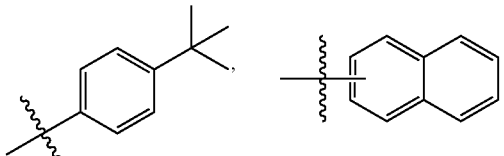
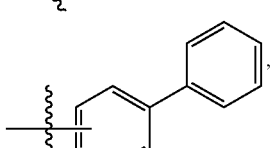
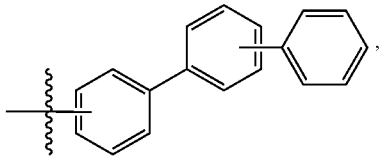

-continued

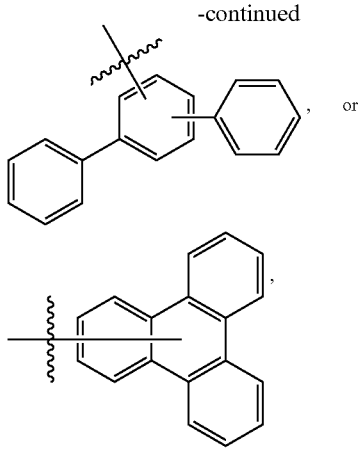

or each independently can be combined with an adjacent substituent to form a benzene ring.

5. The compound according to claim 1, wherein $R_5$ and $R_6$ are each independently hydrogen, methyl, ethyl, propyl,

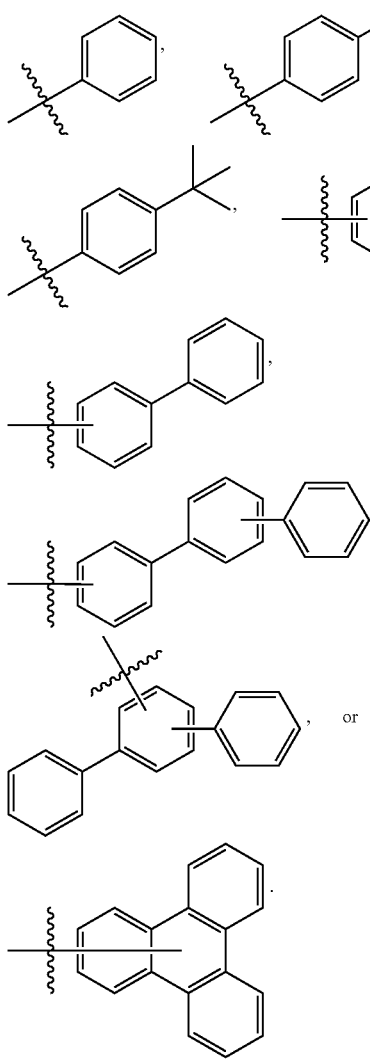

6. The compound according to claim 1, wherein n is 1 or 2, and m is 1.

7. The compound according to claim 1, wherein:

$L_1$ is a direct bond or any one selected from the group consisting of the following:

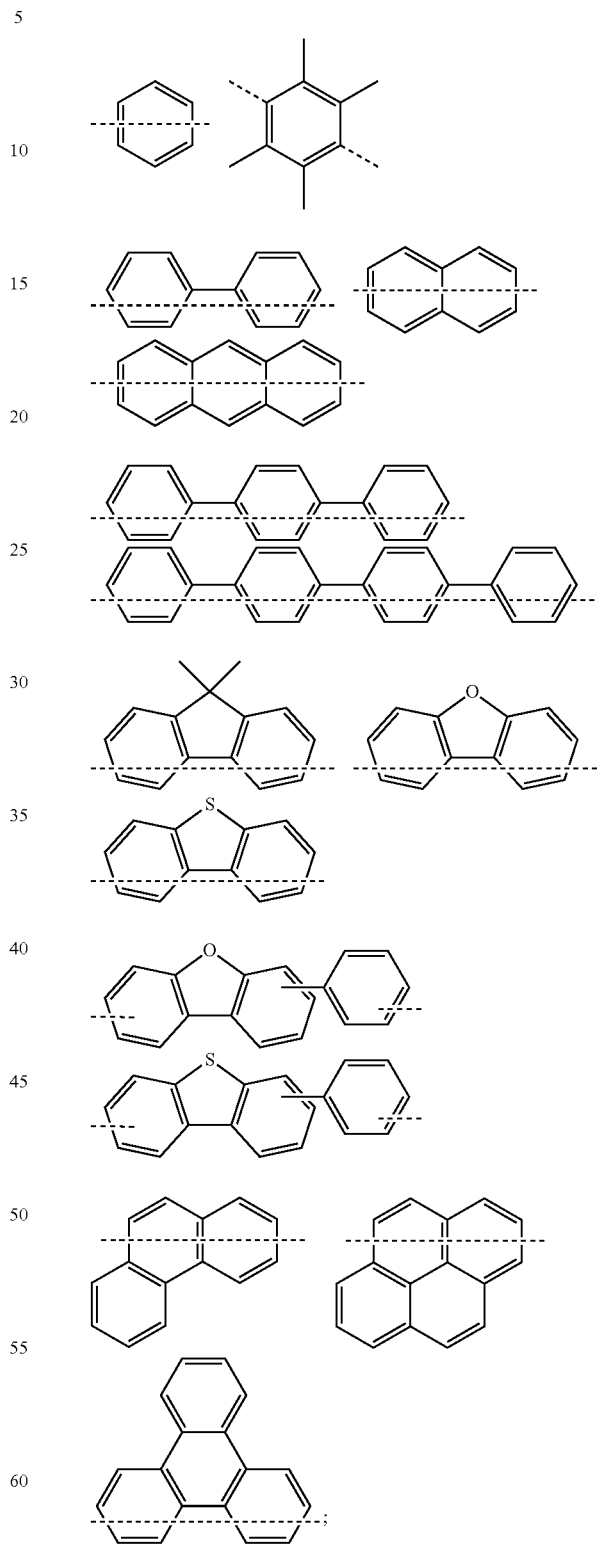

and $L_2$ is a direct bond or any one selected from the group consisting of the following:

115
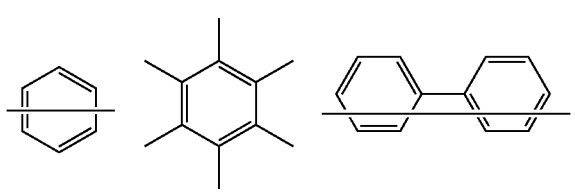
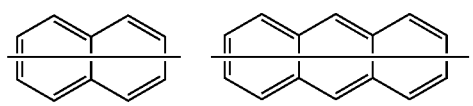
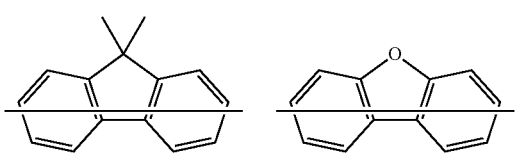
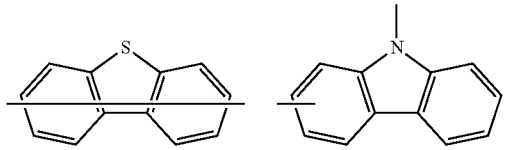
116
-continued
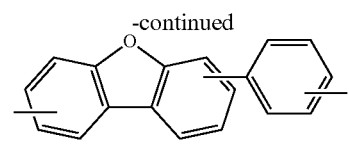
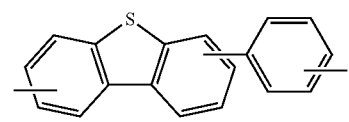
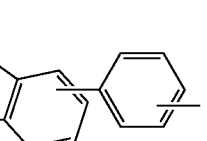
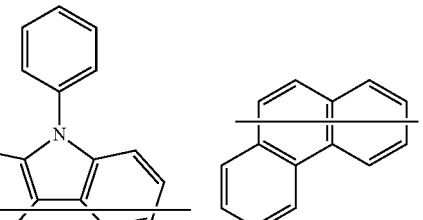
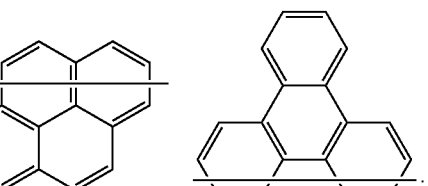
8. The compound according to claim 1, wherein the compound of Chemical Formula 1 is any one compound selected from the group consisting of the following:
Formula 1-A-1
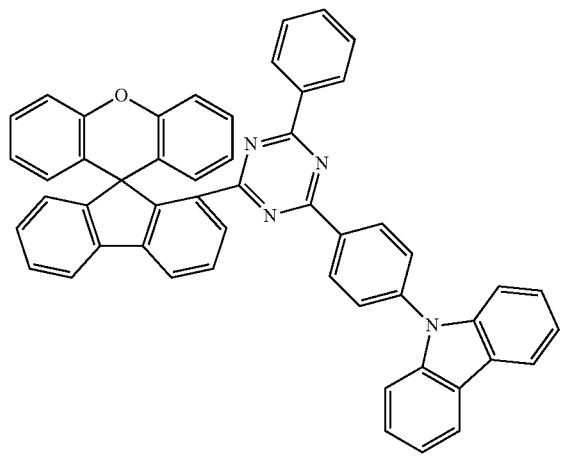
Formula 1-A-2
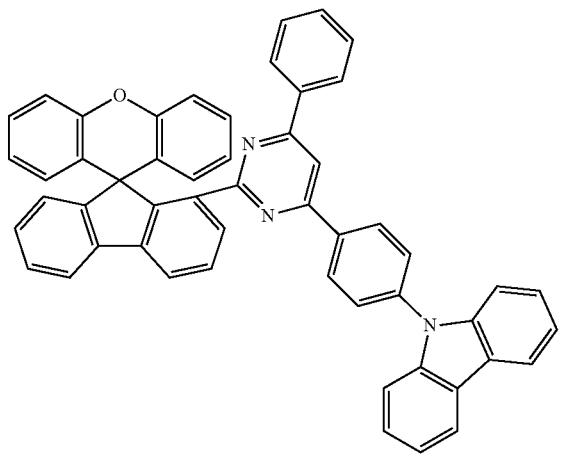

-continued
Formula 1-A-3
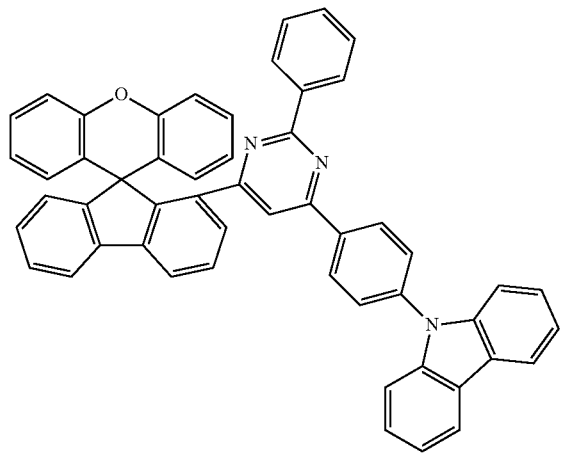
Formula 1-A-4
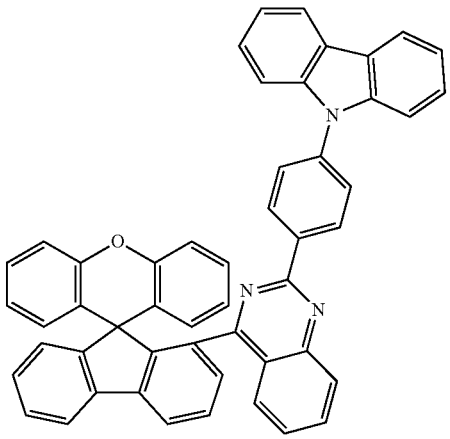
Formula 1-A-5
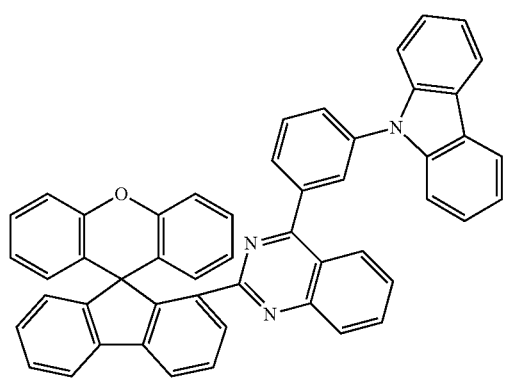
Formula 1-A-6
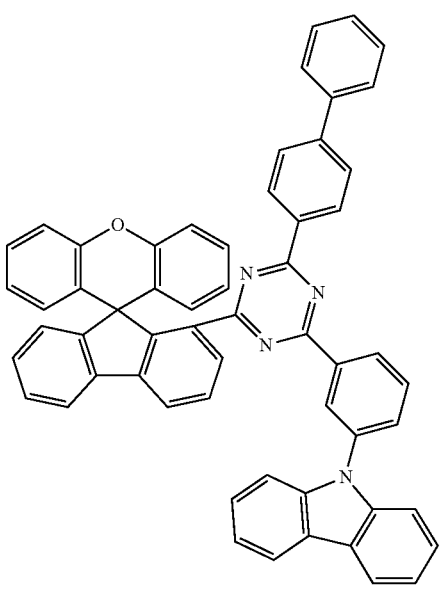
Formula 1-A-7
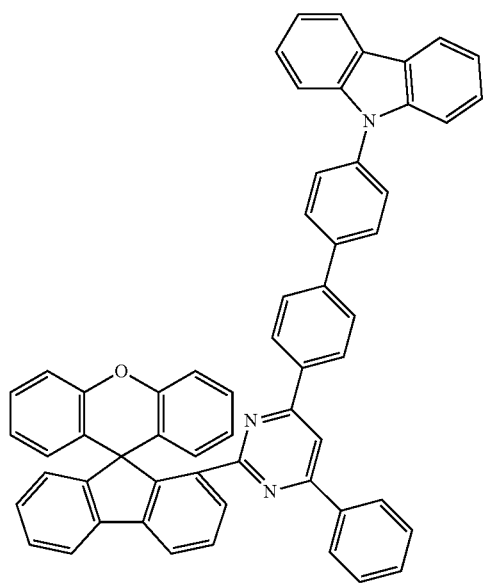
Formula 1-A-8
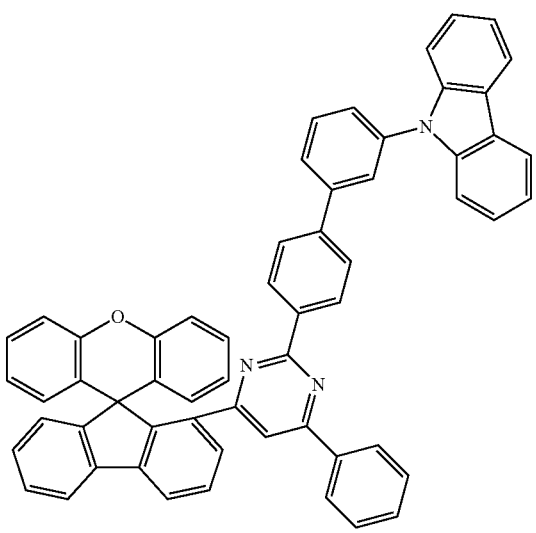

-continued
Formula 1-A-9
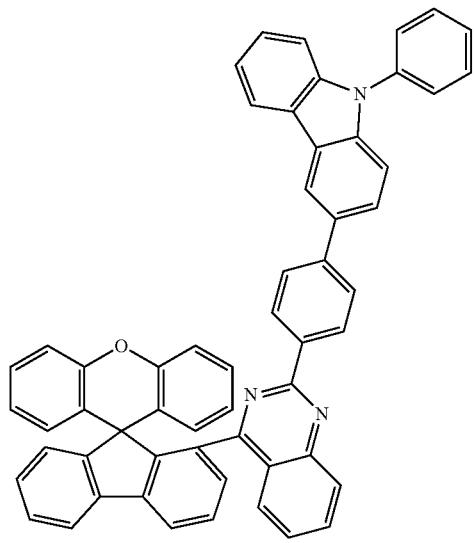
Formula 1-A-10
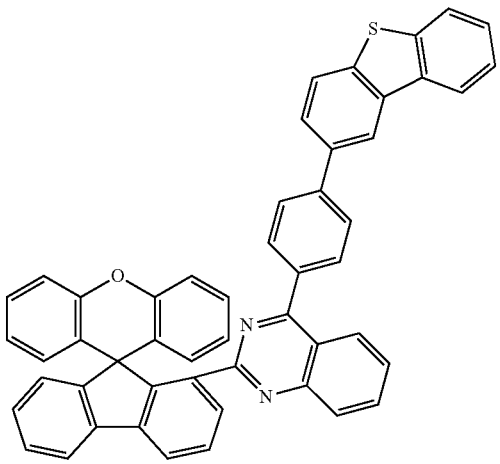
Formula 1-A-11
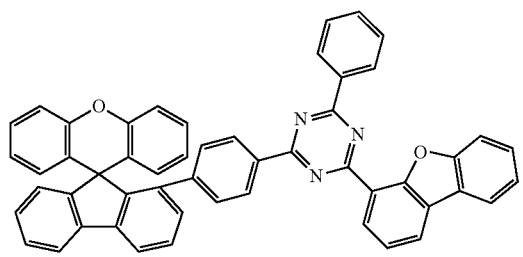
Formula 1-A-12
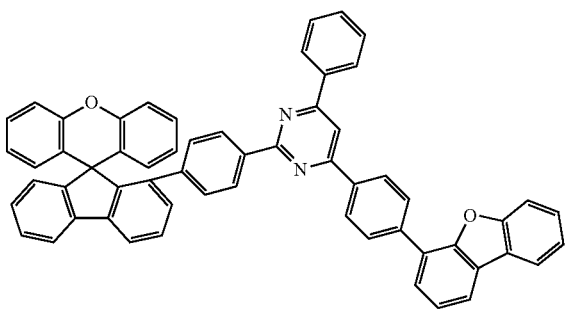
Formula 1-A-13
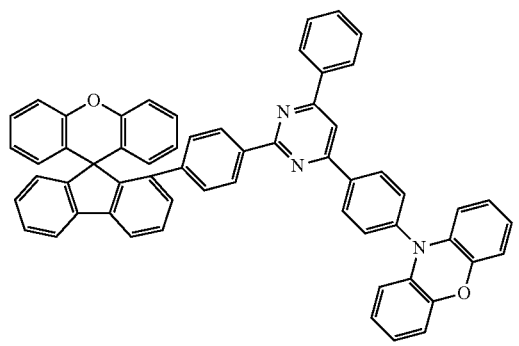
Formula 1-A-14
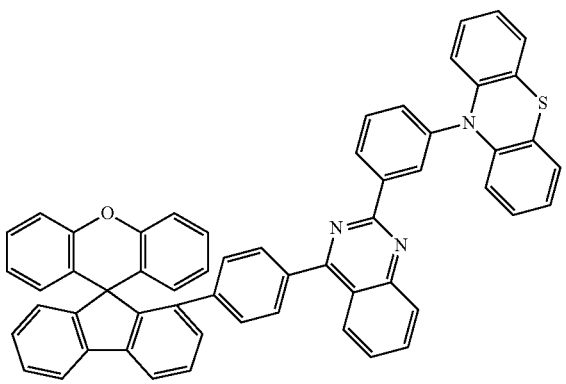
Formula 1-A-15
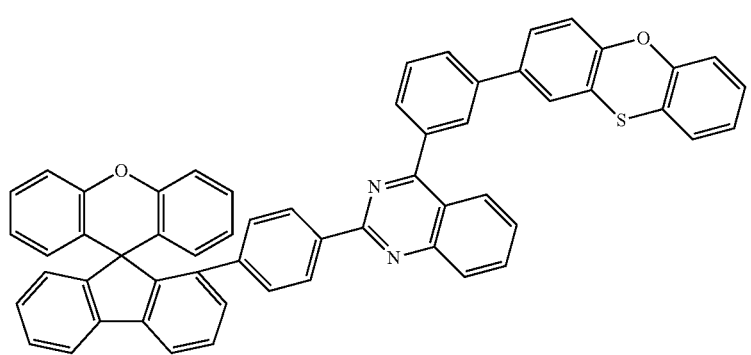

-continued
Formula 1-A-16
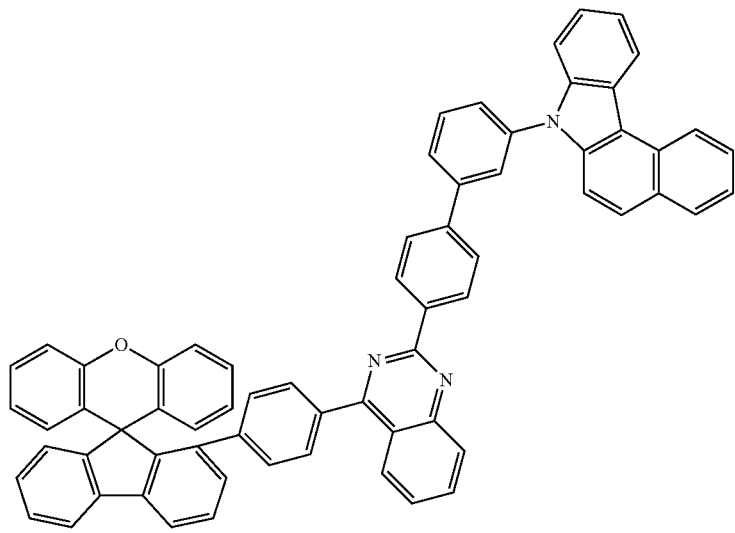
Formula 1-A-17
Formula 1-A-18
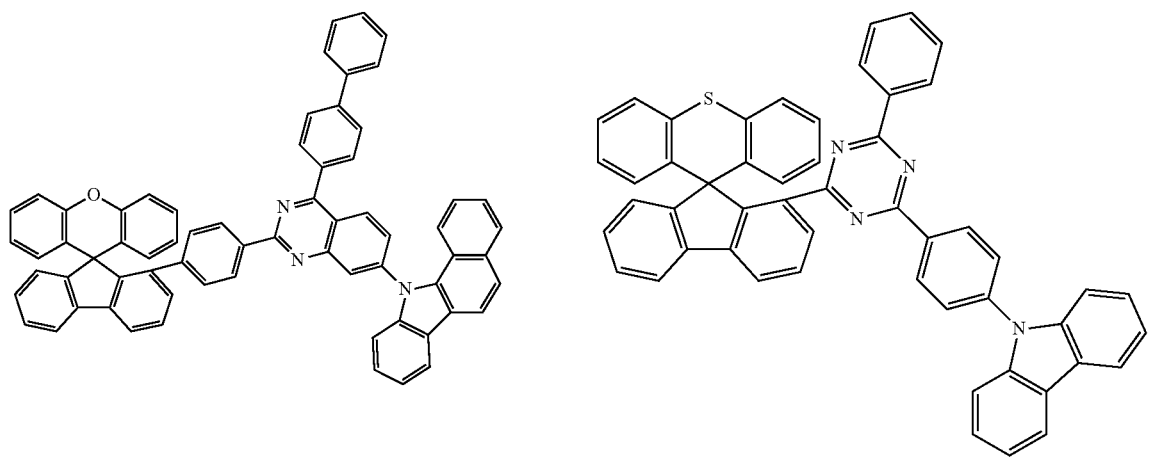
Formula 1-A-19
Formula 1-A-20
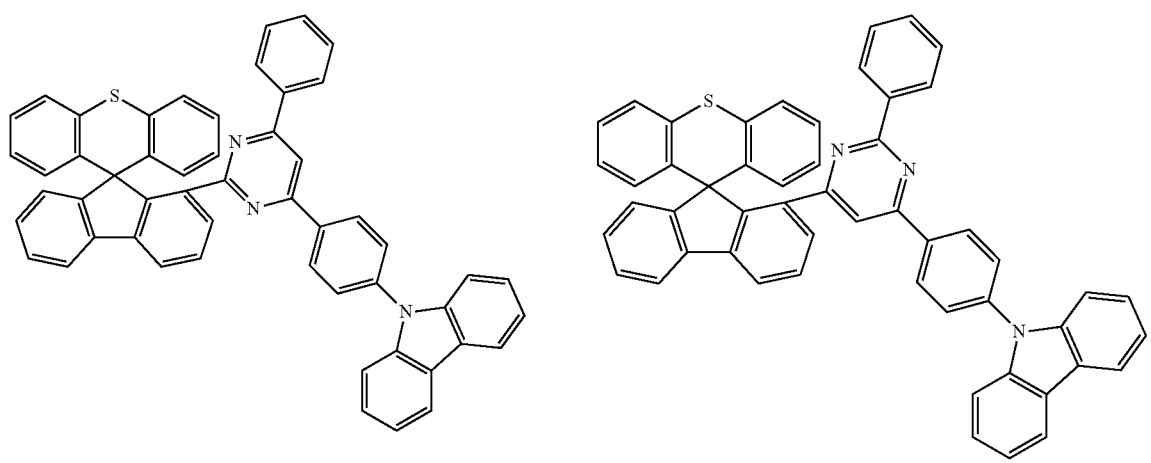

-continued
Formula 1-A-21
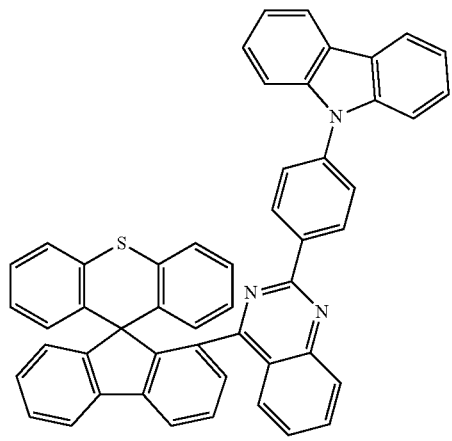
Formula 1-A-22
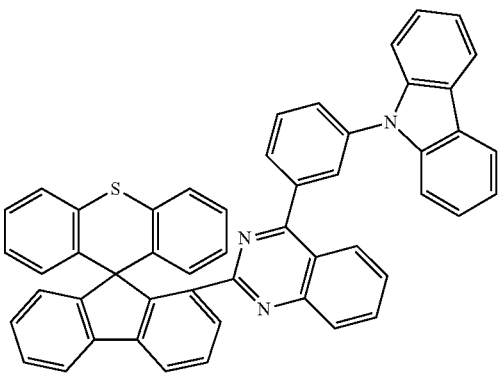
Formula 1-A-23
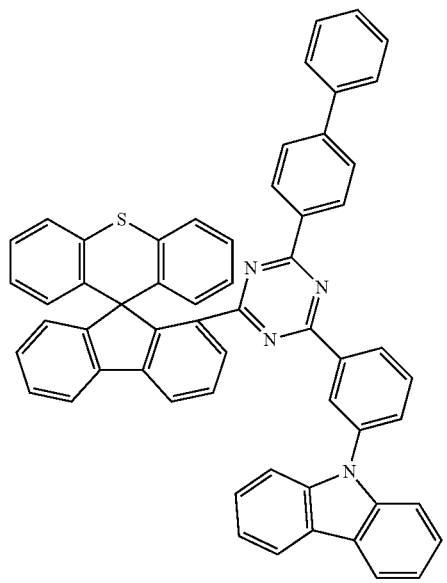
Formula 1-A-24
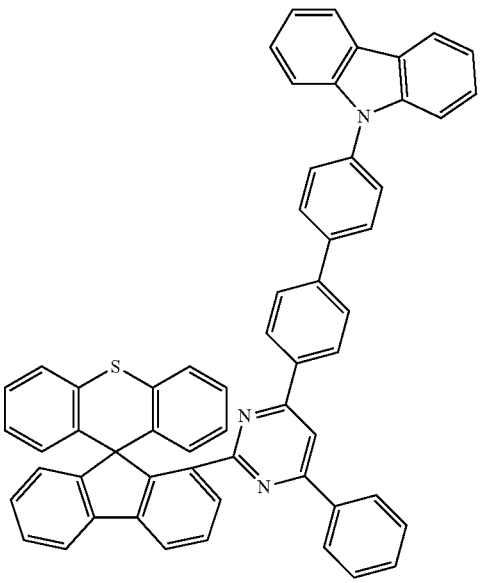
Formula 1-A-25
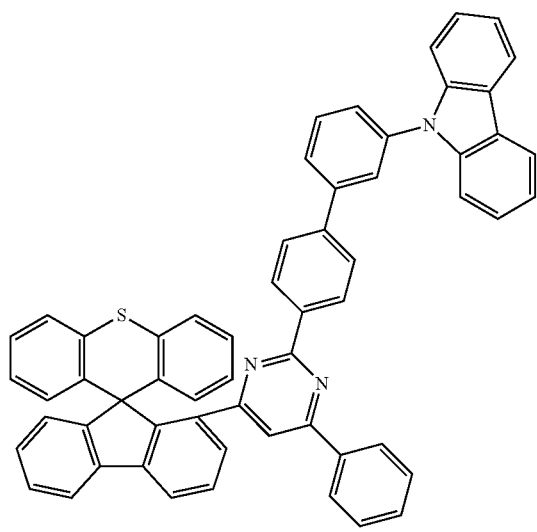
Formula 1-A-26
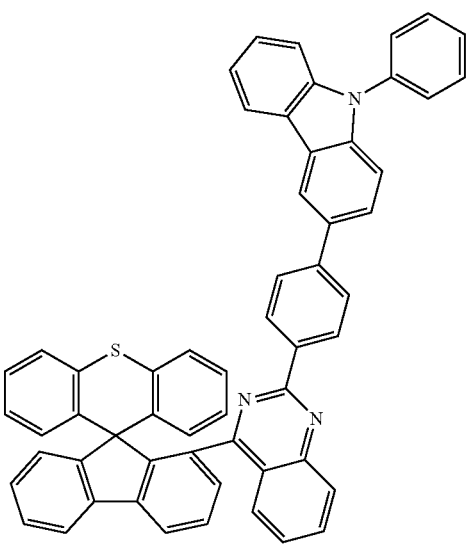

-continued
Formula 1-A-27
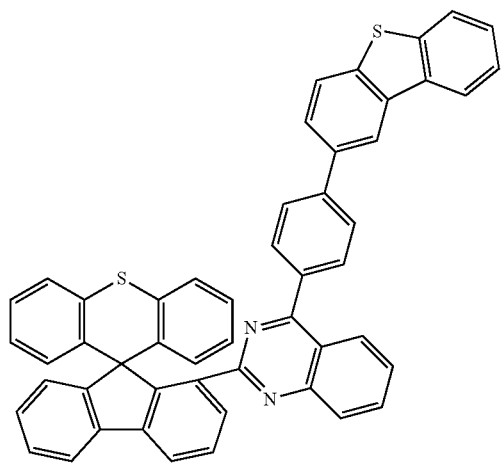
Formula 1-A-28
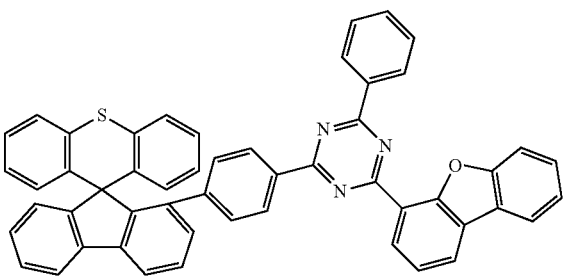
Formula 1-A-29
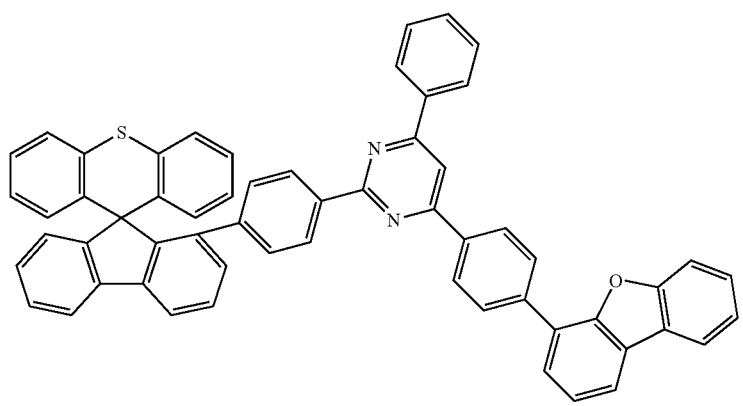
Formula 1-A-30
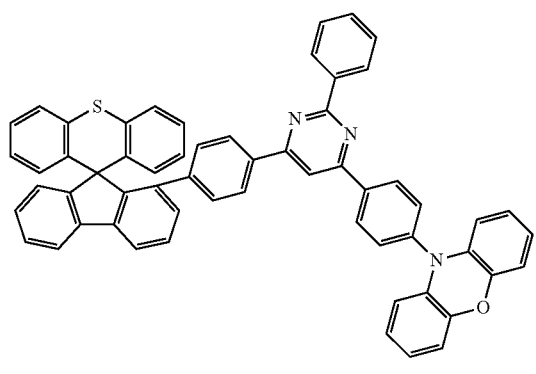
Formula 1-A-31
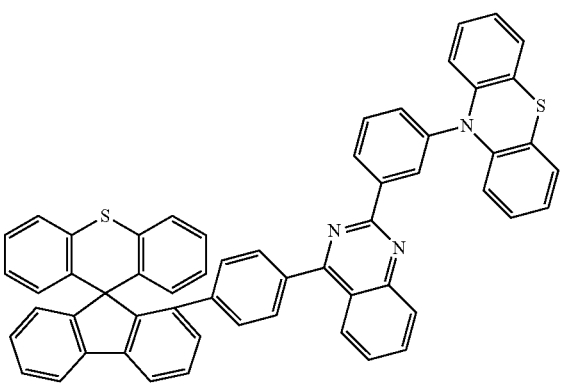
Formula 1-A-32
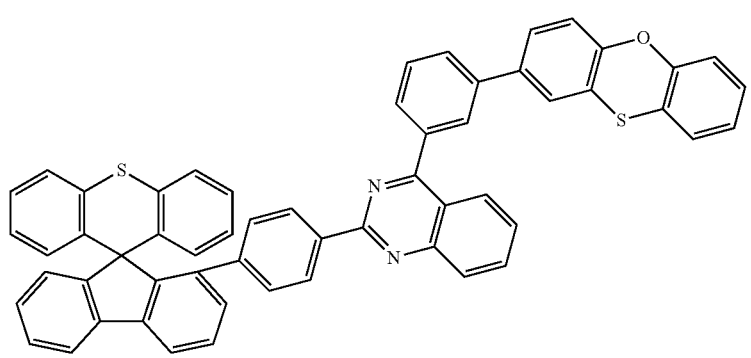

Formula 1-A-33
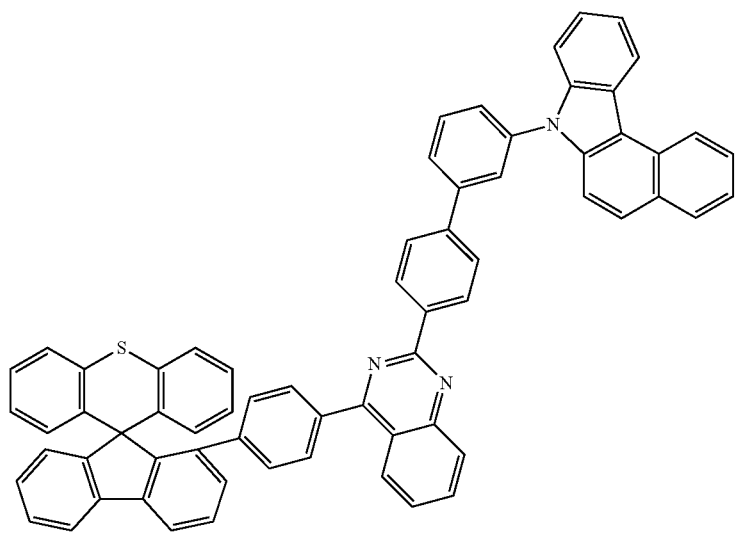
Formula 1-A-34
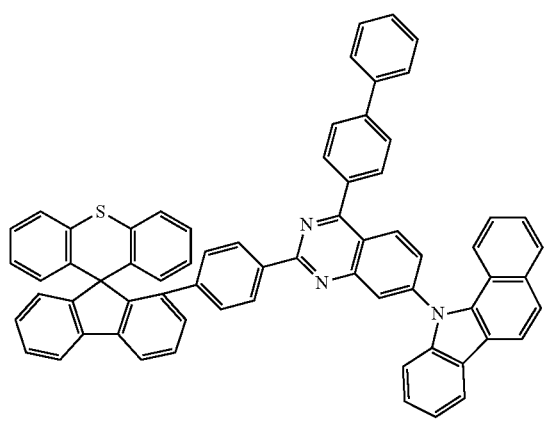
Formula 1-A-35
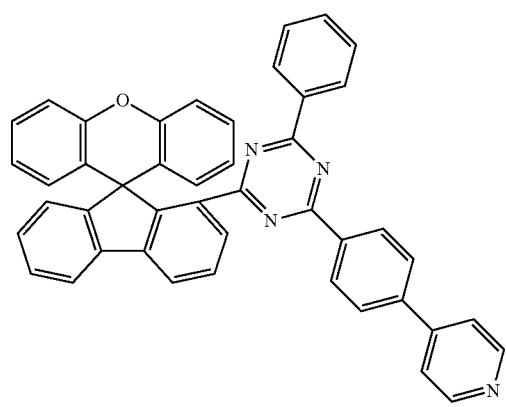
Formula 1-A-36
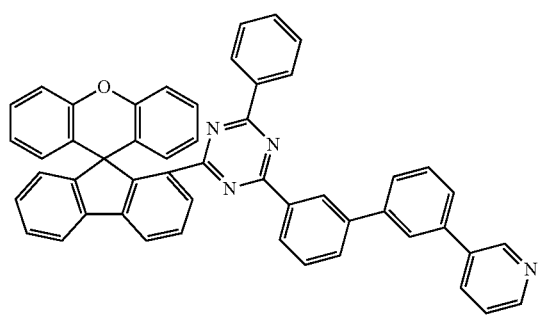
Formula 1-A-37
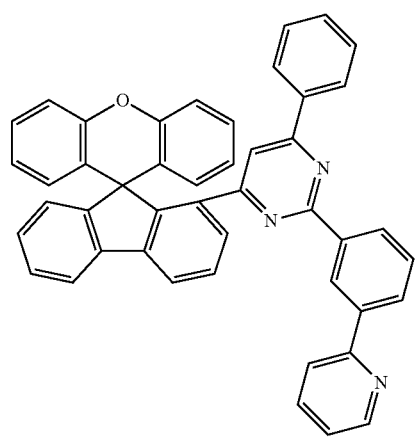

-continued
Formula 1-A-38
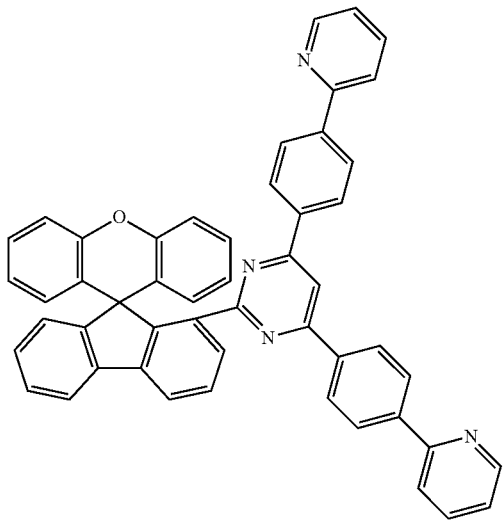
Formula 1-B-1
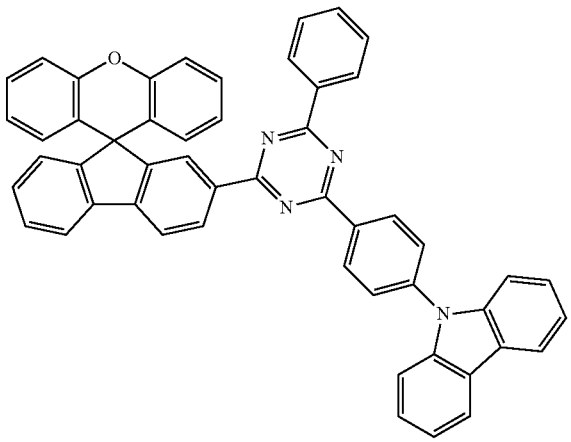
Formula 1-B-2
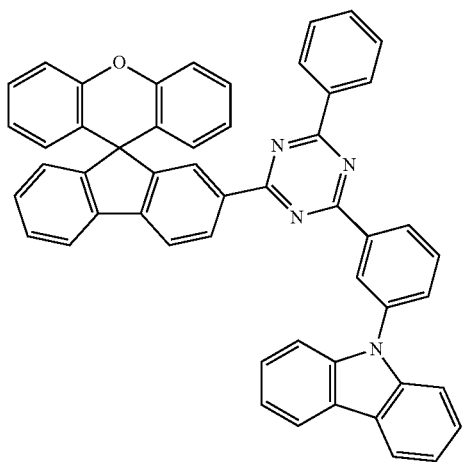
Formula 1-B-3
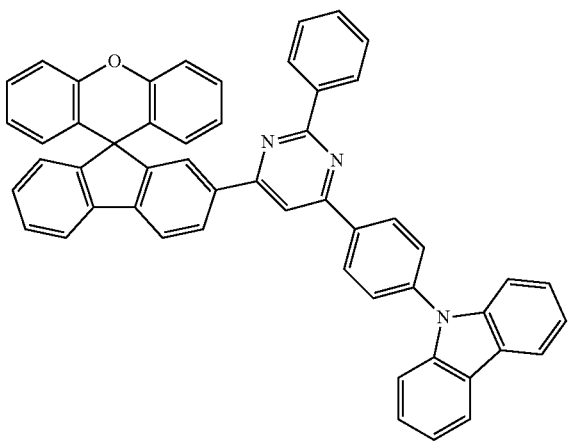
Formula 1-B-4
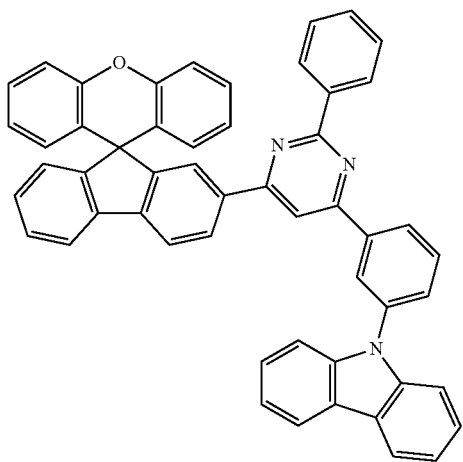
Formula 1-B-5
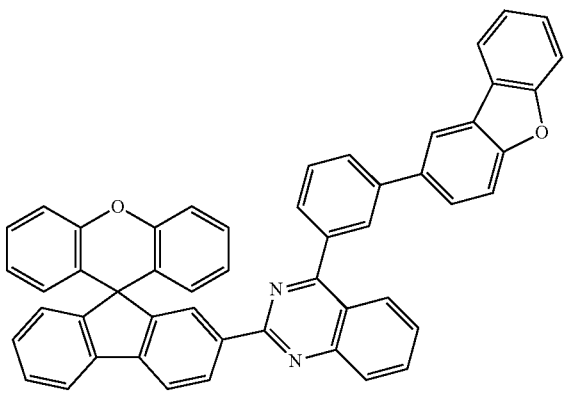

-continued
Formula 1-B-6
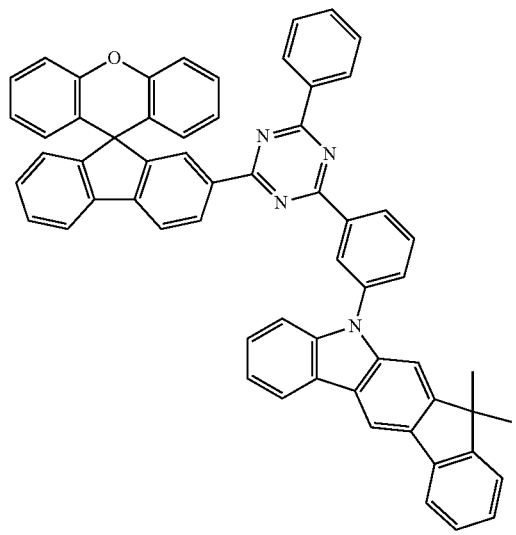
Formula 1-B-7
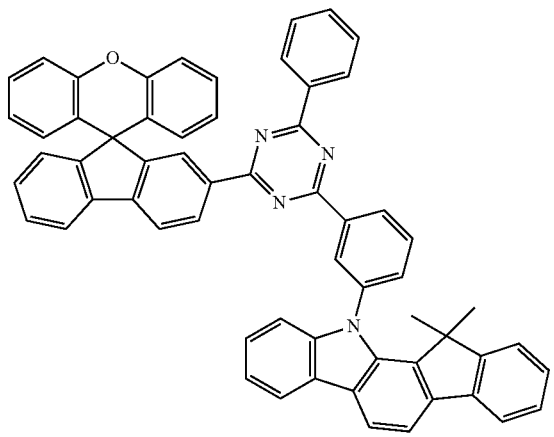
Formula 1-B-8
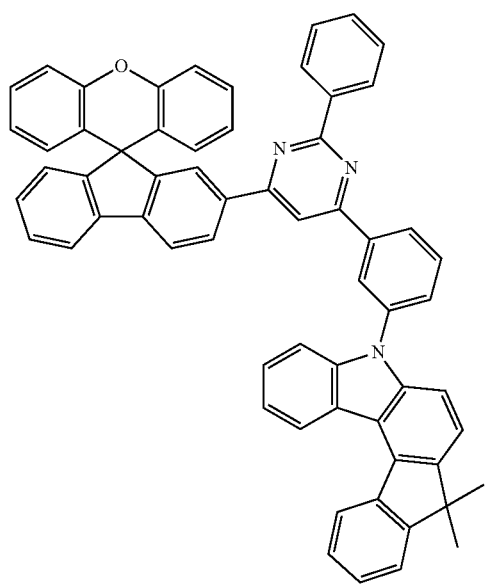
Formula 1-B-9
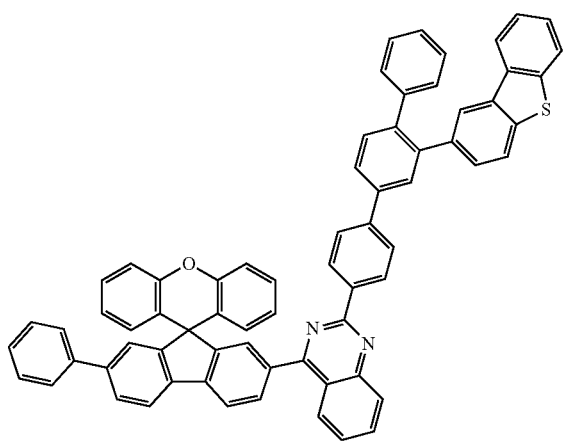
Formula 1-B-10
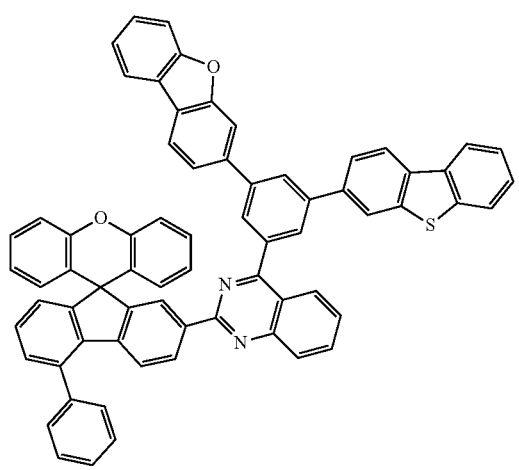
Formula 1-B-11
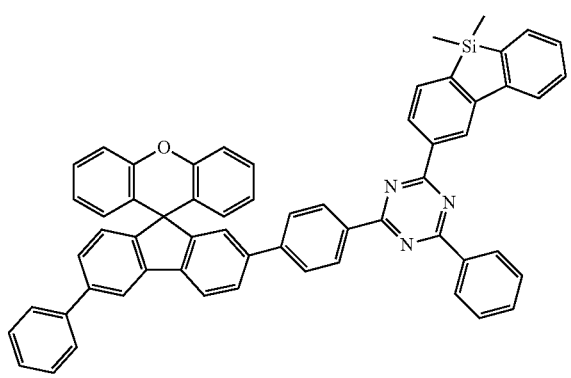

Formula 1-B-12
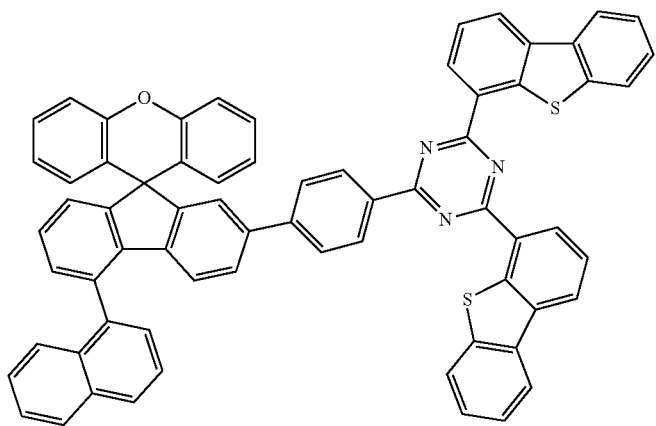
Formula 1-B-13
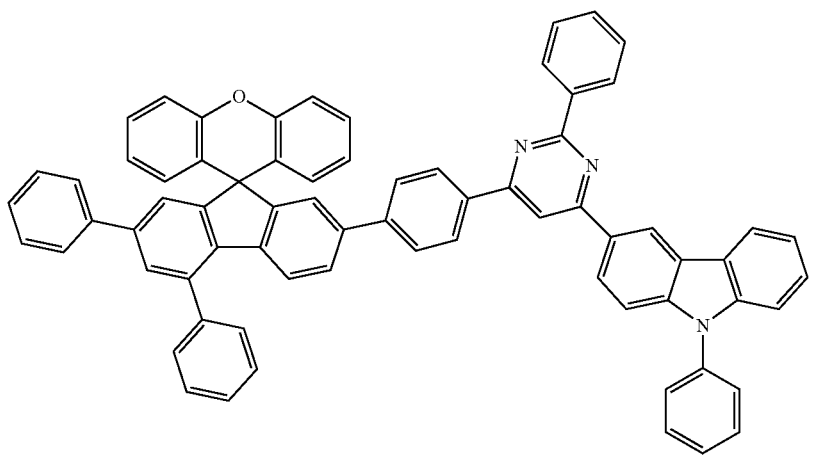
Formula 1-B-14
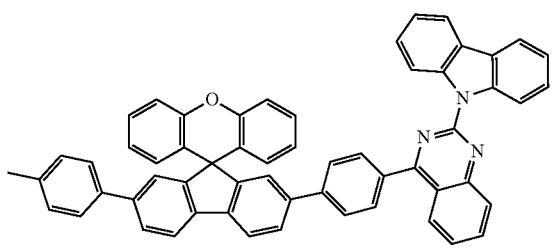
Formula 1-B-15
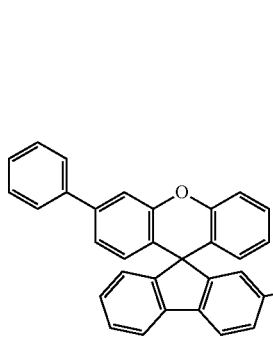

-continued
Formula 1-B-16
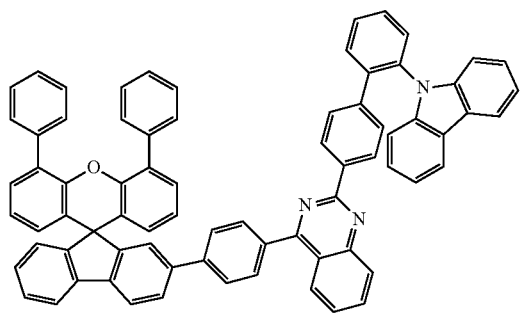
Formula 1-B-17
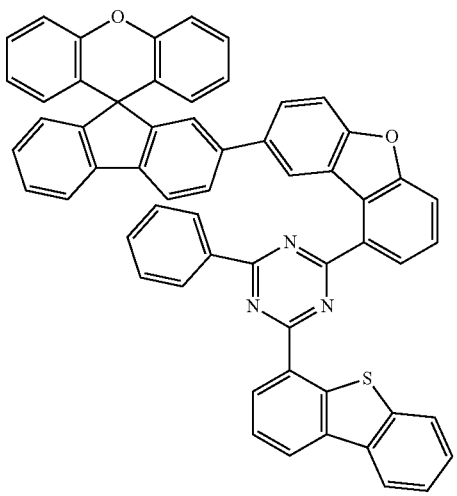
Formula 1-B-18
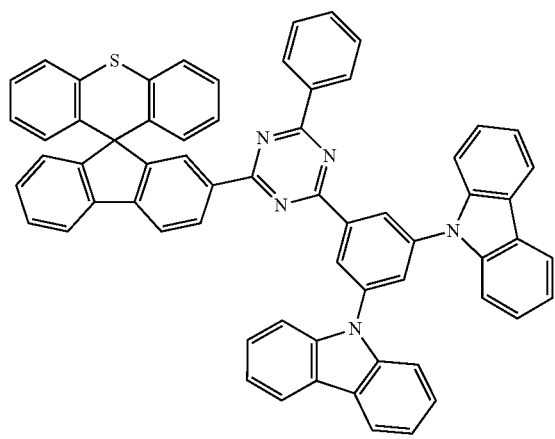
Formula 1-B-19
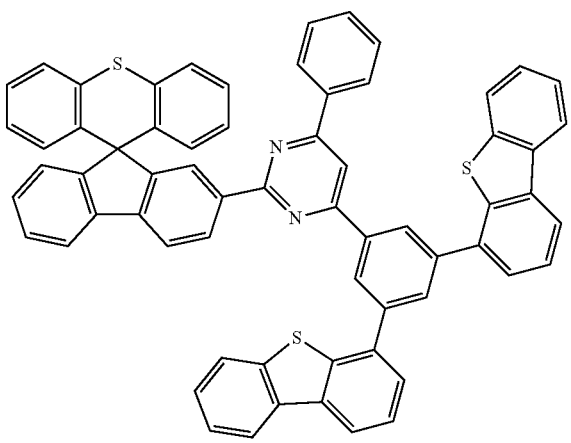
Formula 1-B-20
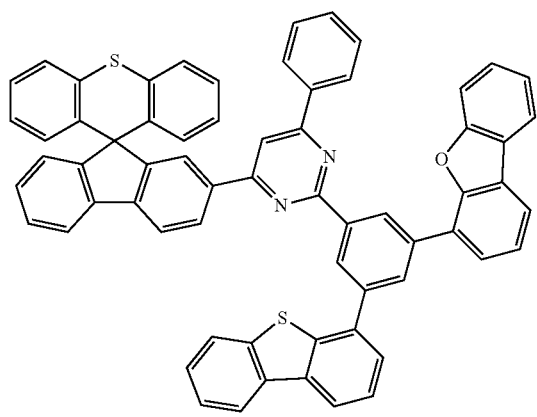
Formula 1-B-21
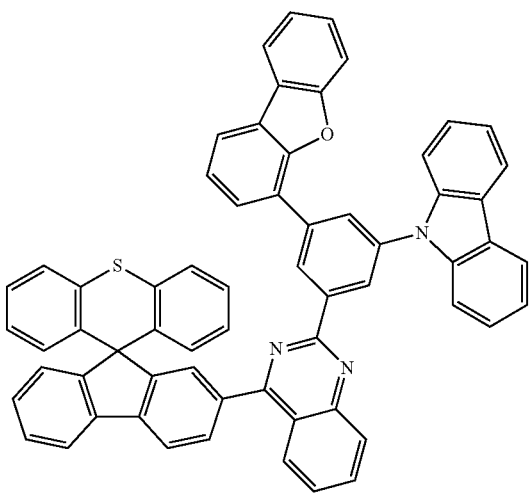

-continued
Formula 1-B-22
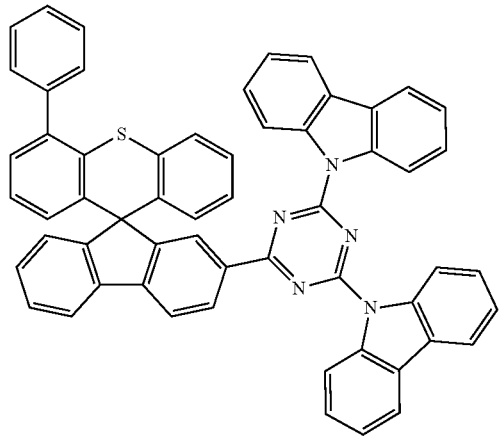
Formula 1-B-23
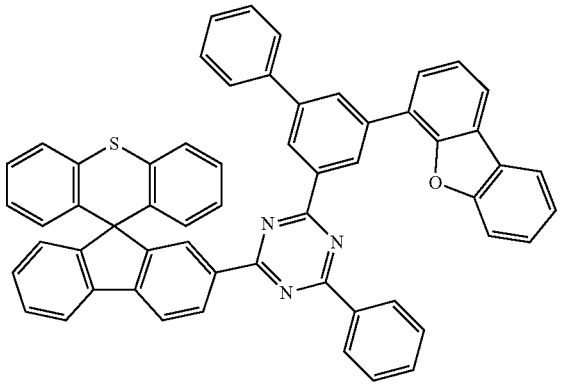
Formula 1-B-24
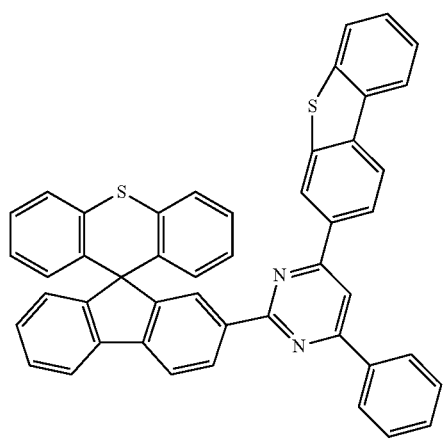
Formula 1-B-25
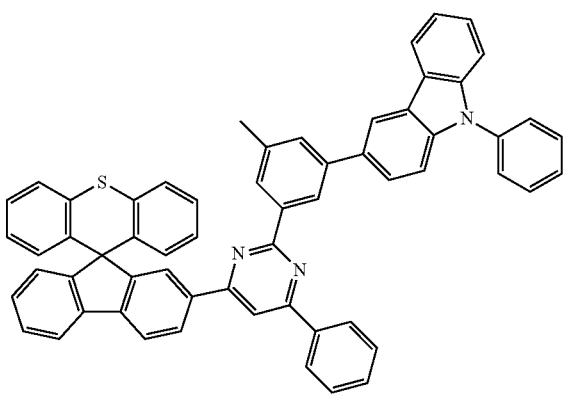
Formula 1-B-26
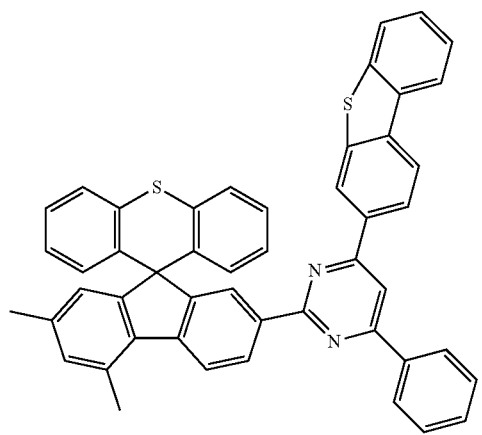
Formula 1-B-27
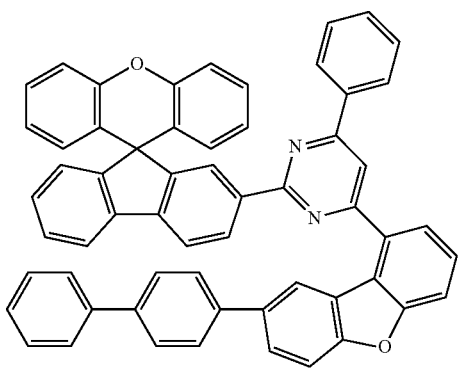

-continued
Formula 1-B-28
Formula 1-B-29
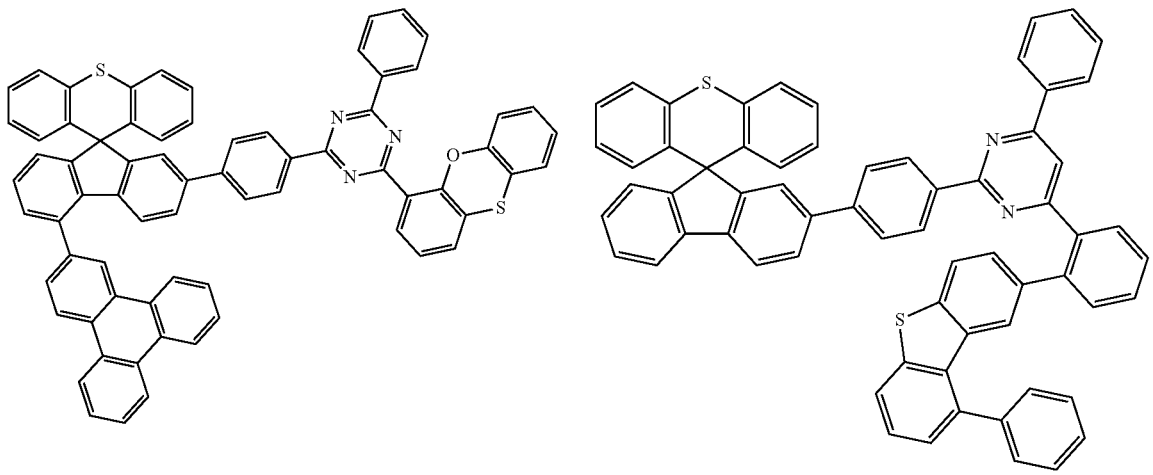
Formula 1-B-30
Formula 1-B-31
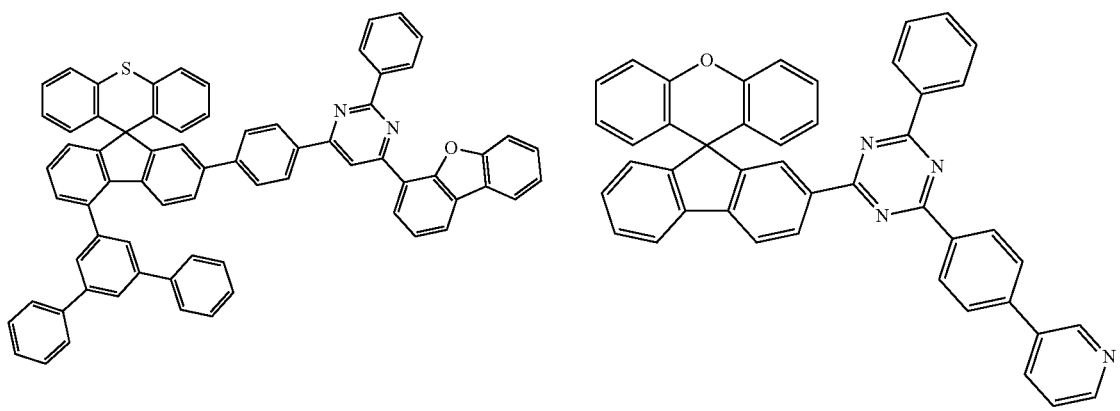
Formula 1-B-32
Formula 1-B-33
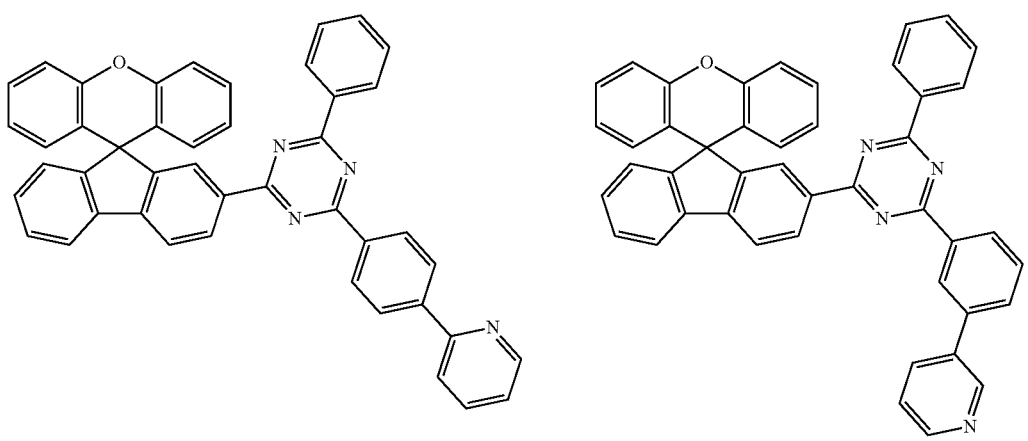

-continued
Formula 1-B-34
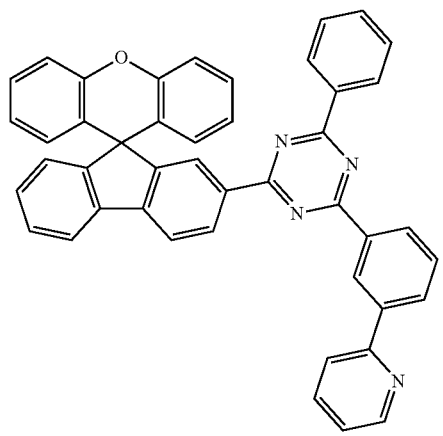
Formula 1-B-35
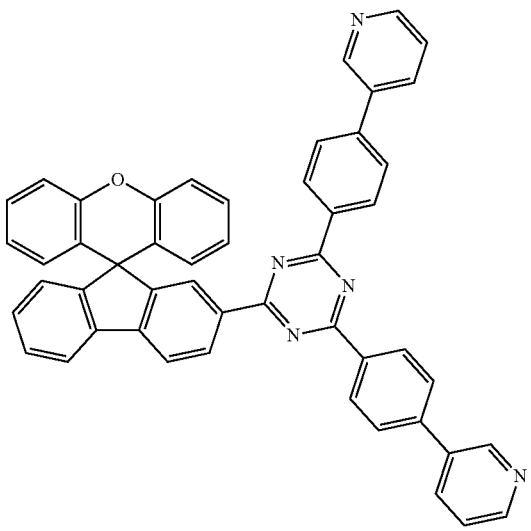
Formula 1-B-36
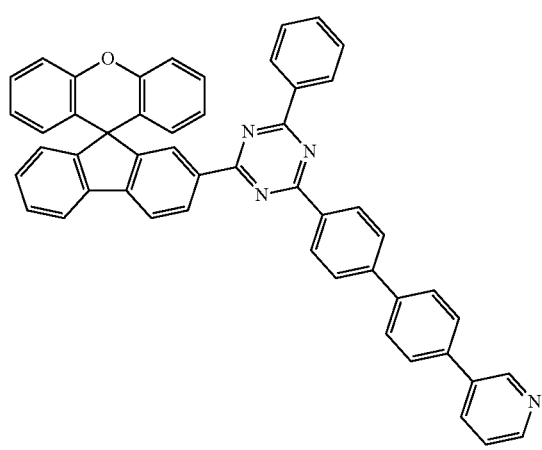
Formula 1-B-37
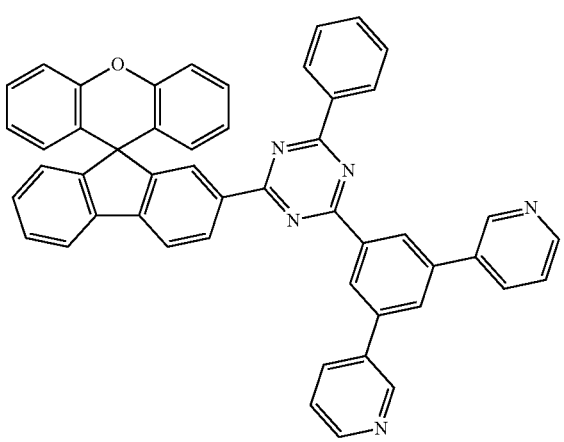
Formula 1-B-38
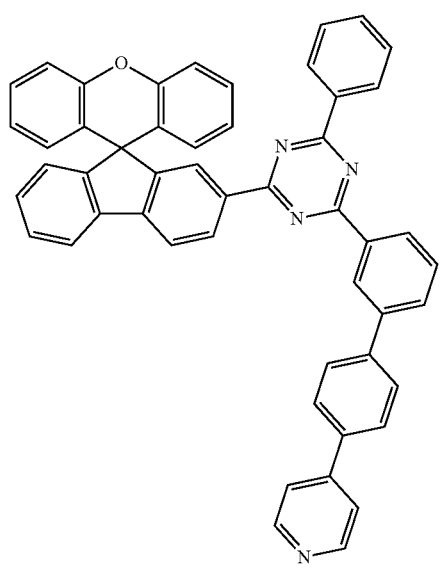
Formula 1-B-39
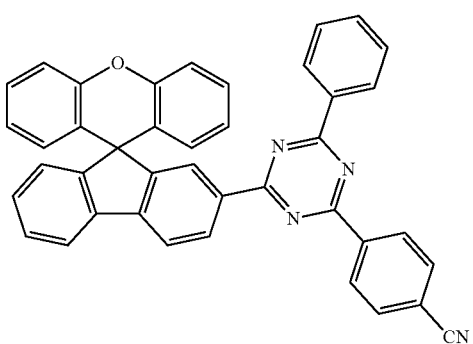

-continued
Formula 1-B-40
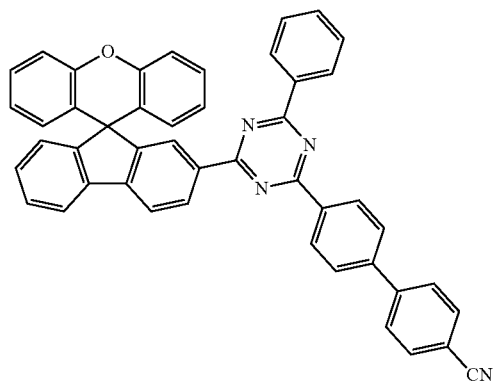
Formula 1-B-41
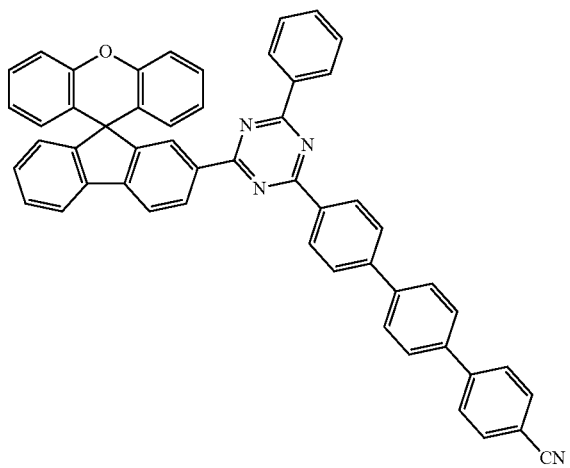
Formula 1-B-42
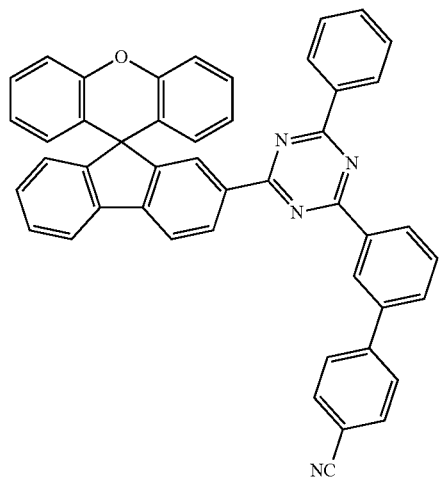
Formula 1-B-43
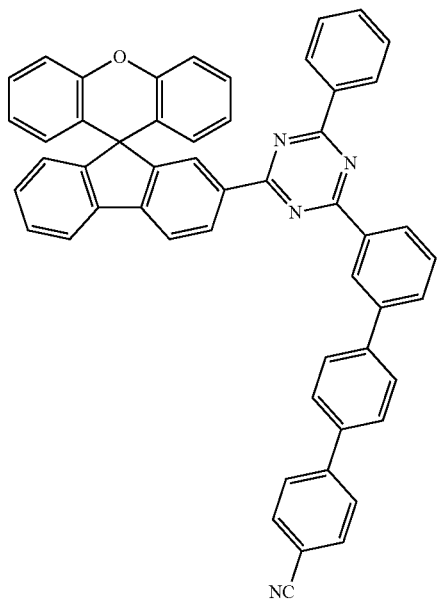
Formula 1-B-44
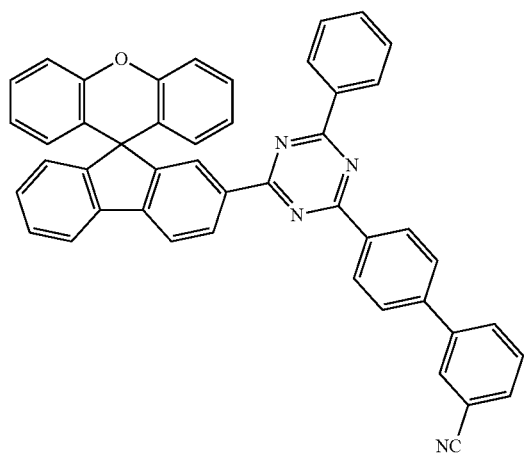
Formula 1-B-45
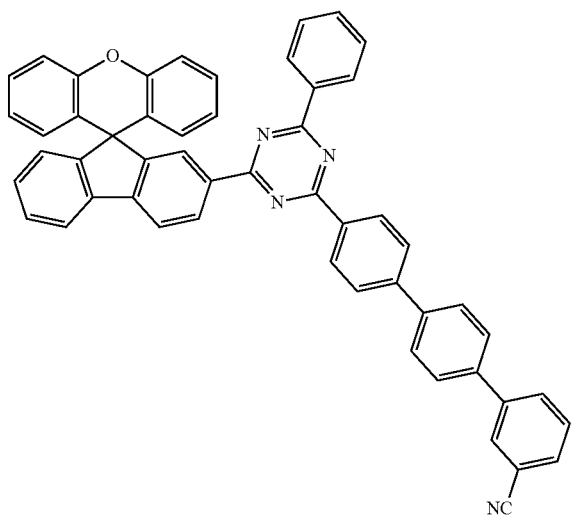

Formula 1-B-46
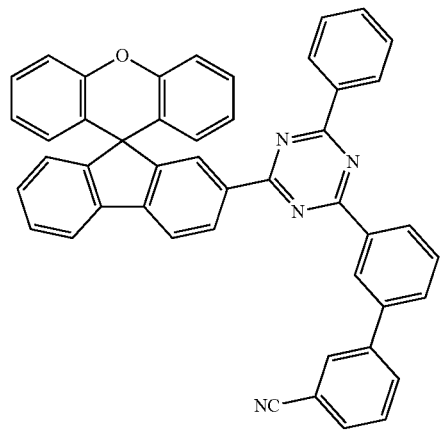
Formula 1-B-47
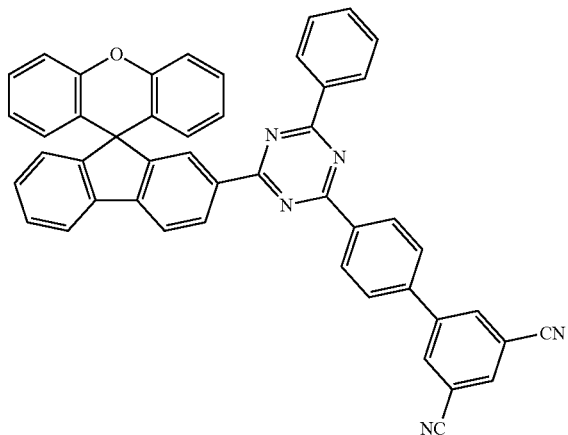
Formula 1-B-48
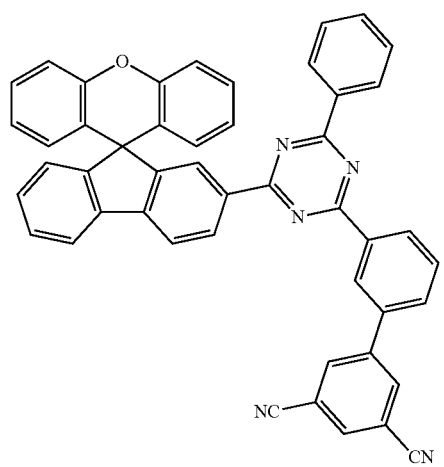
Formula 1-B-49
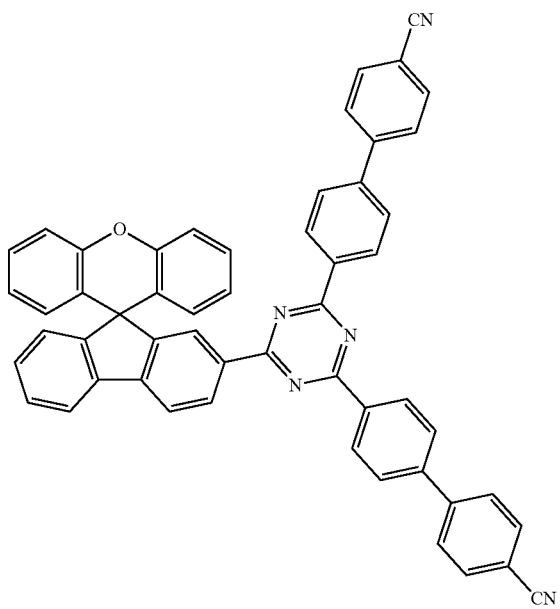

-continued
Formula 1-B-50
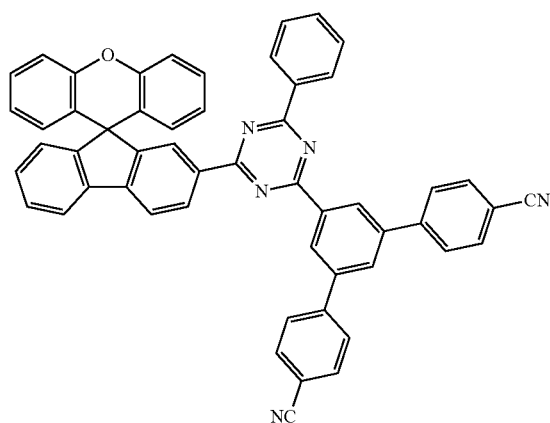
Formula 1-B-51
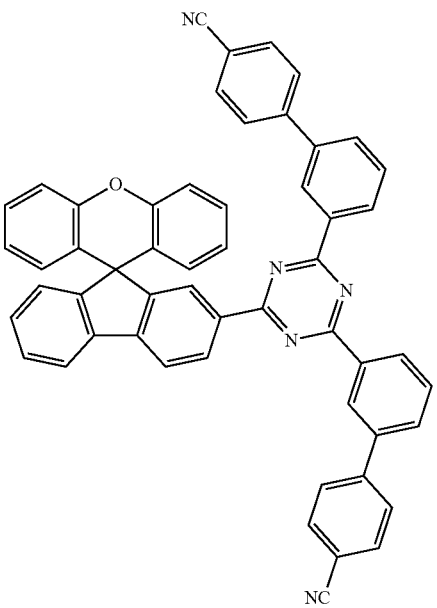
Formula 1-B-52
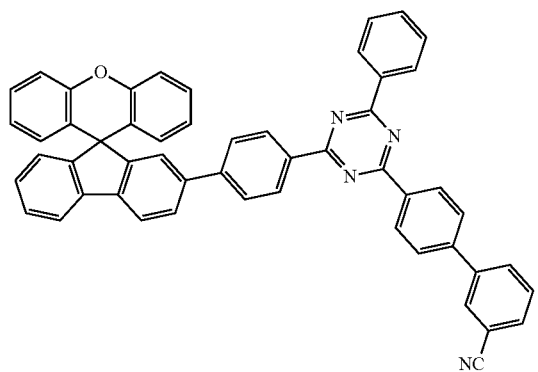
Formula 1-B-53
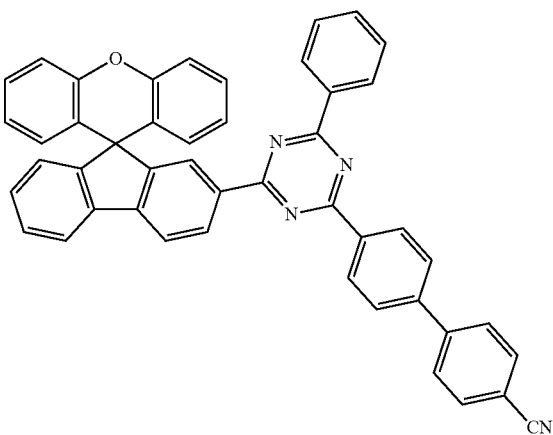
Formula 1-B-54
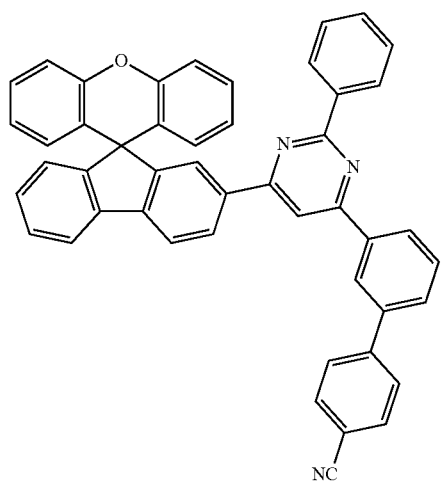
Formula 1-C-1
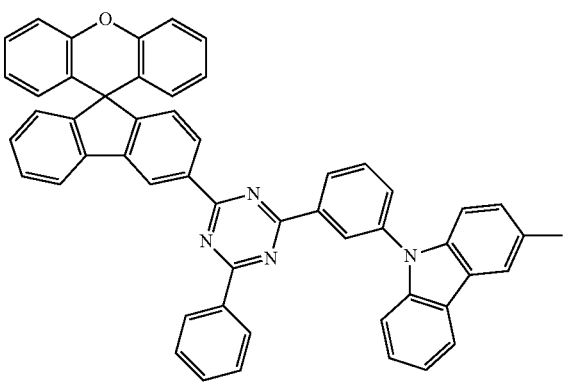

-continued
Formula 1-C-2
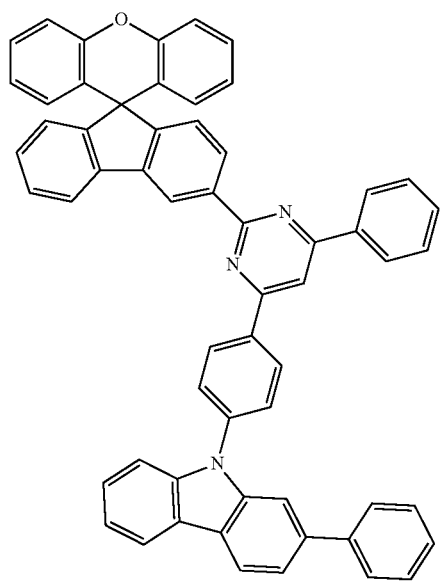
Formula 1-C-3
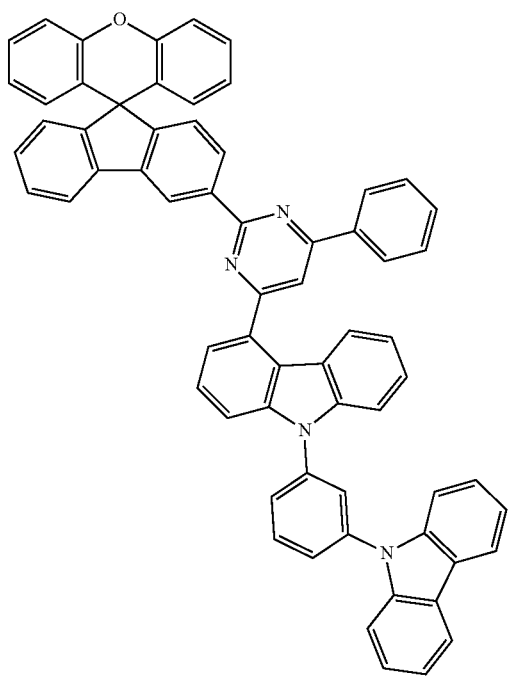
Formula 1-C-4
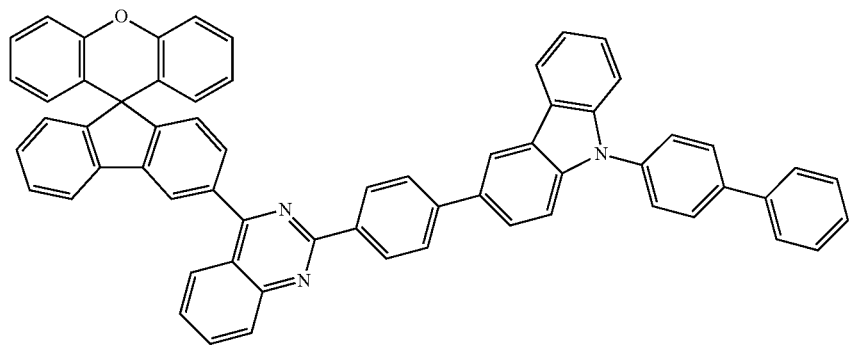
Formula 1-C-5
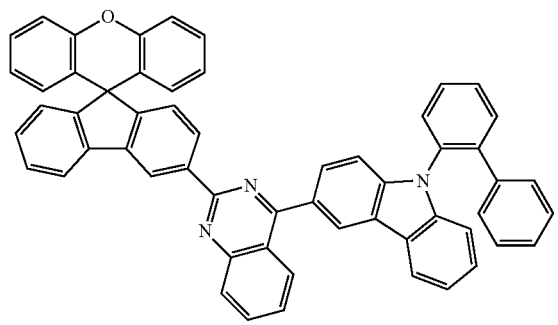
Formula 1-C-6
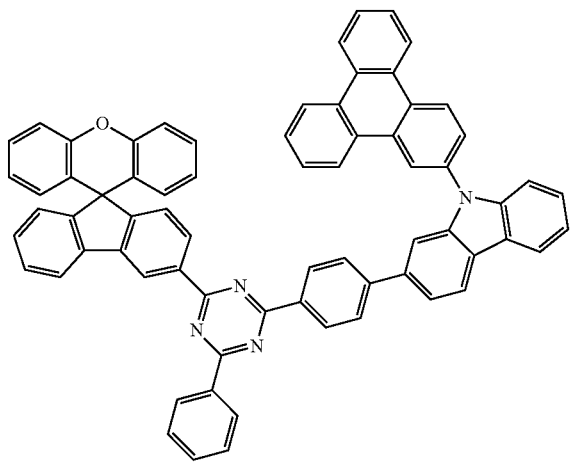

-continued
Formula 1-C-7
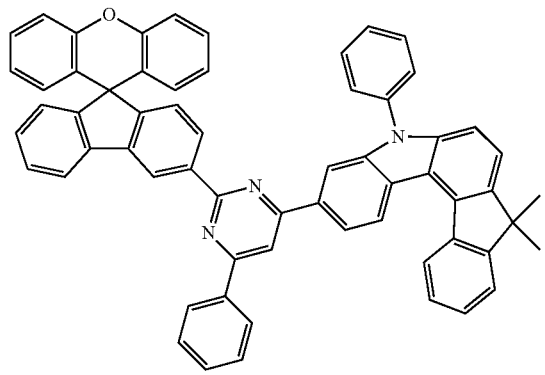
Formula 1-C-8
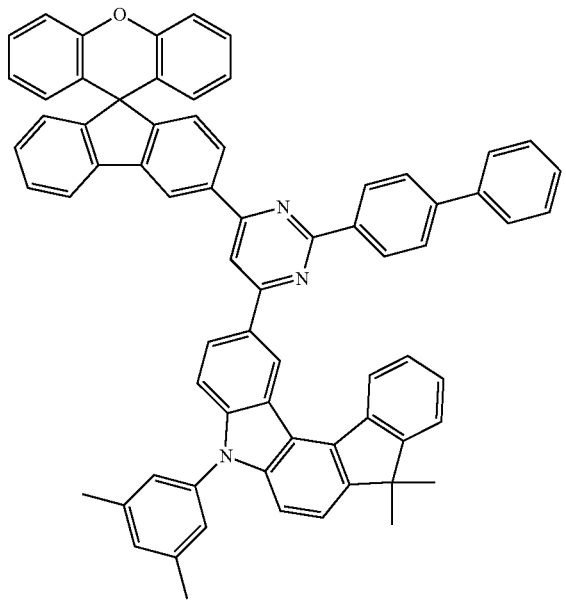
Formula 1-C-9
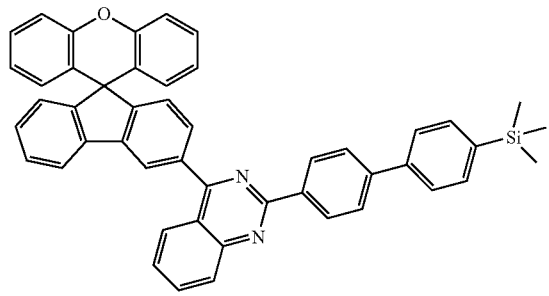
Formula 1-C-10
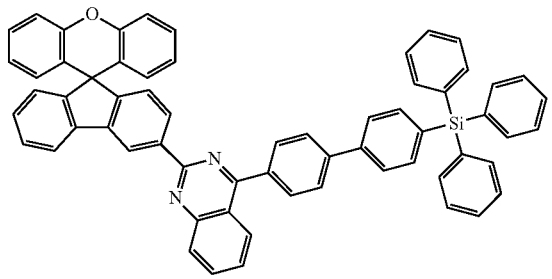
Formula 1-C-11
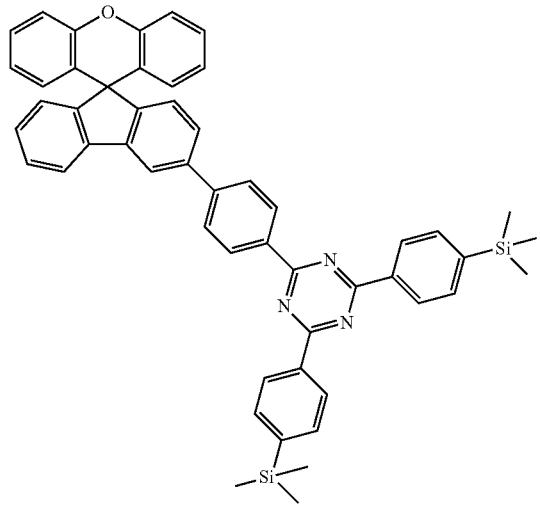
Formula 1-C-12
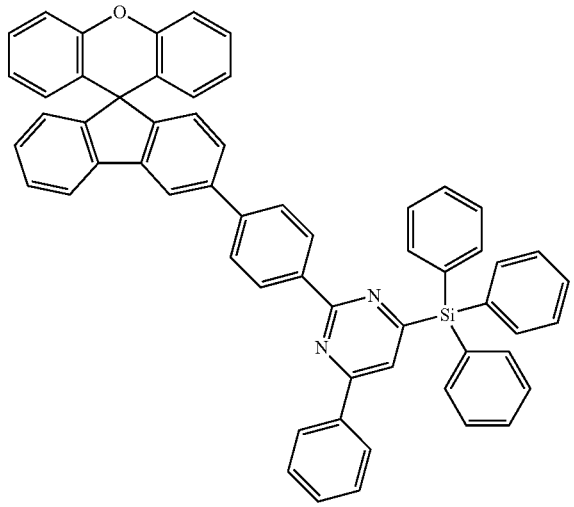

Formula 1-C-17
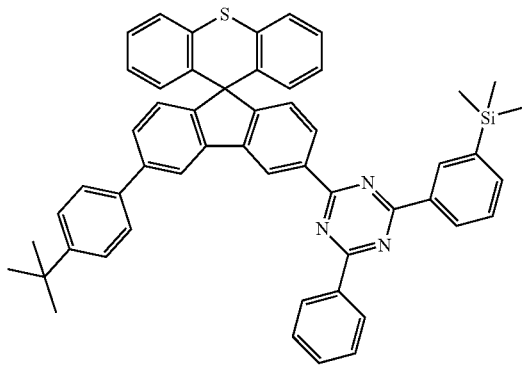
Formula 1-C-18
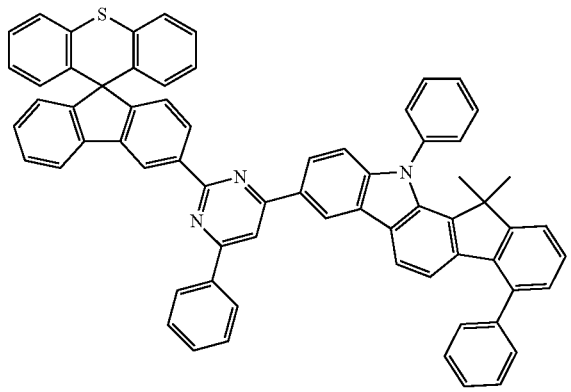
Formula 1-C-19
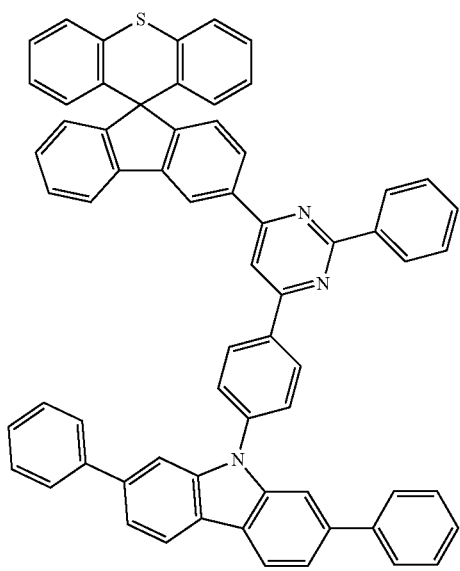
Formula 1-C-20
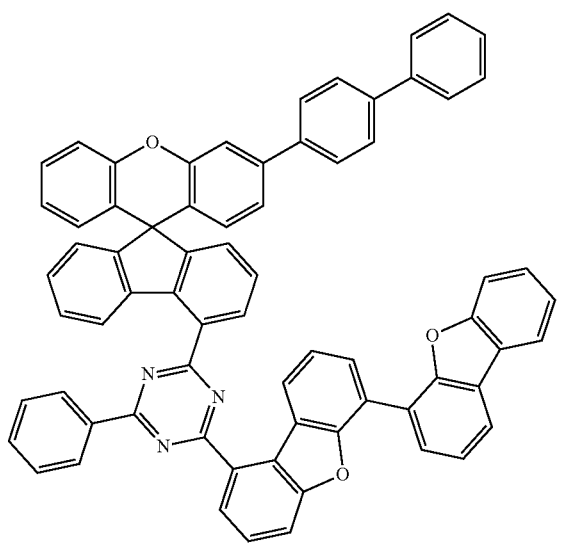
Formula 1-D-1
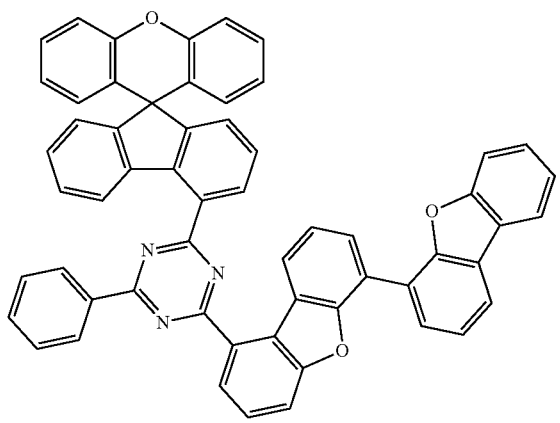
Formula 1-D-2
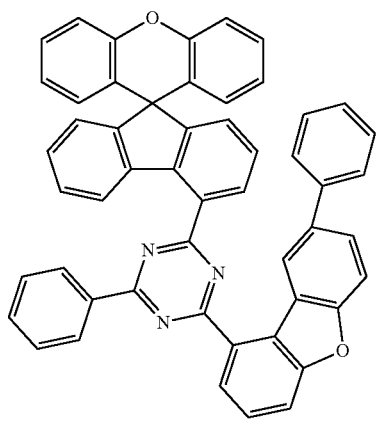

-continued
Formula 1-D-3
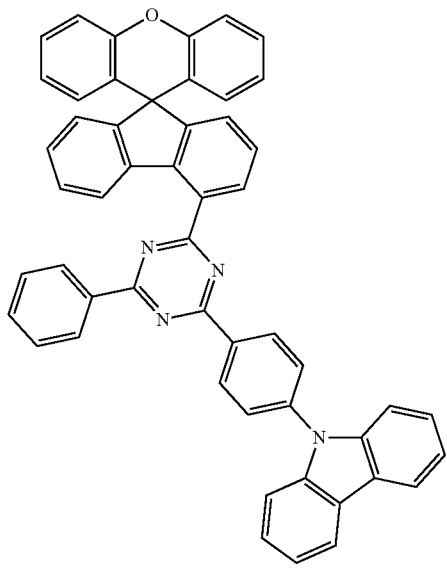
Formula 1-D-4
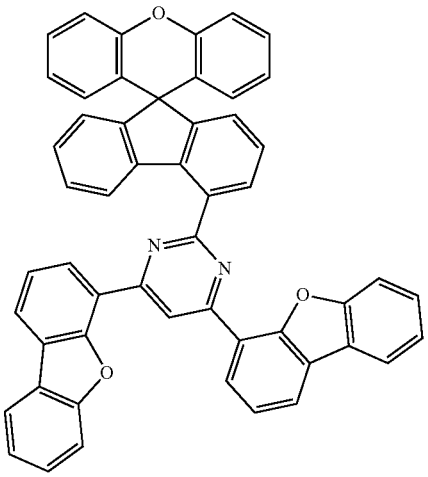
Formula 1-D-5
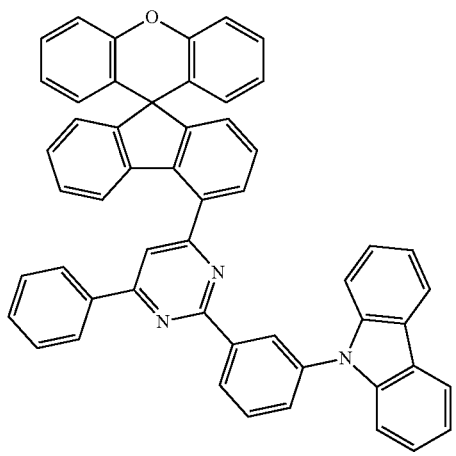
Formula 1-D-6
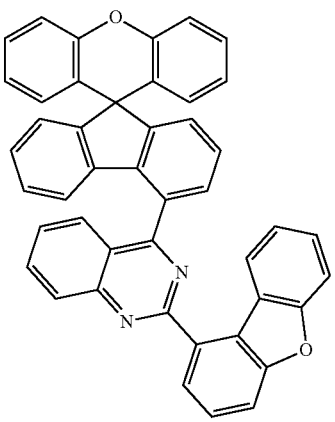
Formula 1-D-7
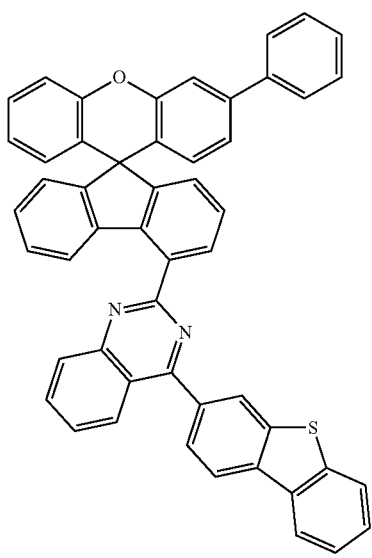
Formula 1-D-8
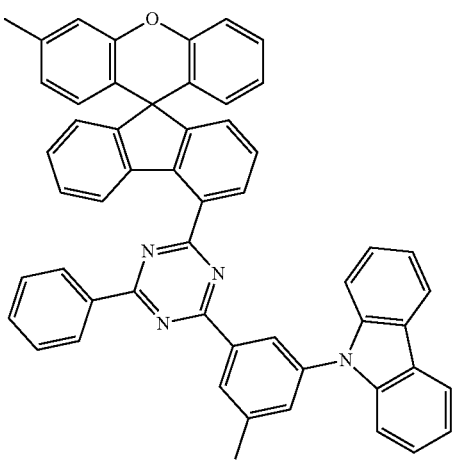

-continued
Formula 1-D-9
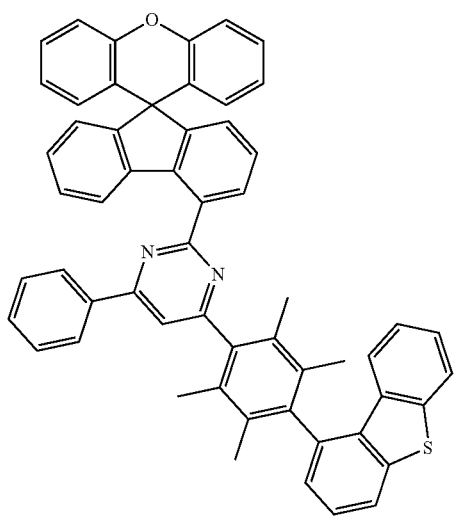
Formula 1-D-10
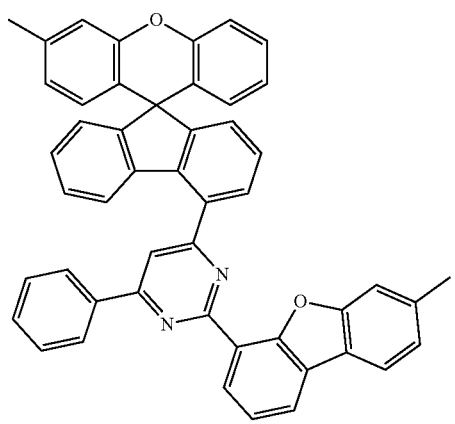
Formula 1-D-9b
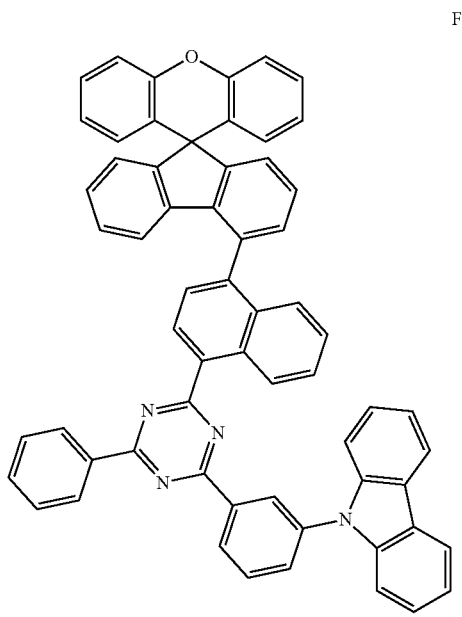
Formula 1-D-10
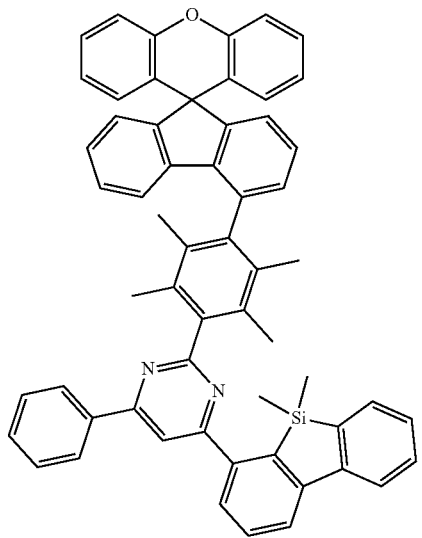

Formula 1-D-11
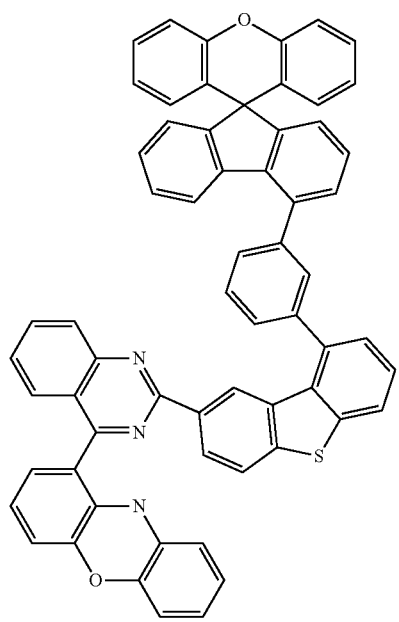
Formula 1-D-12
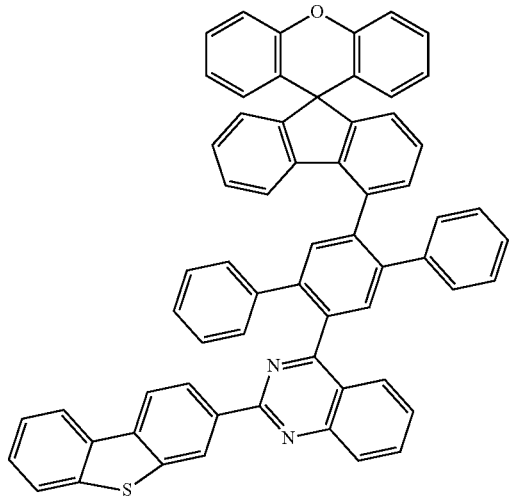
Formula 1-D-13
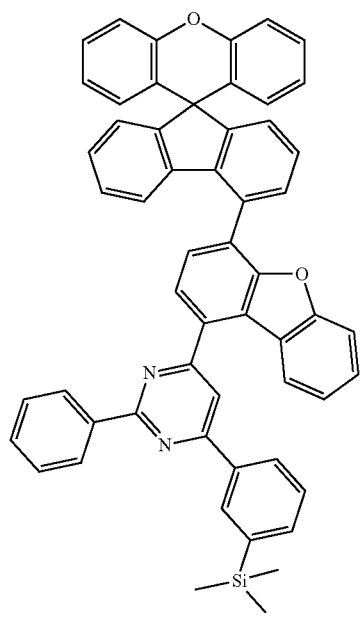
Formula 1-D-14
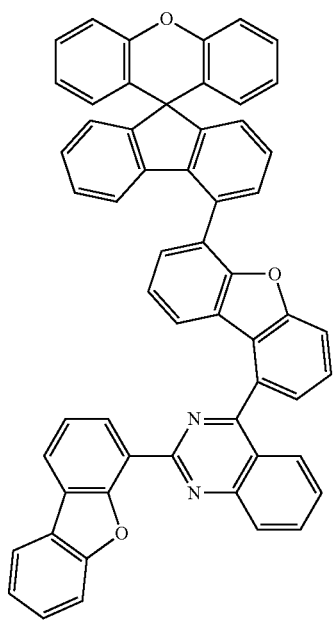

-continued
Formula 1-D-15
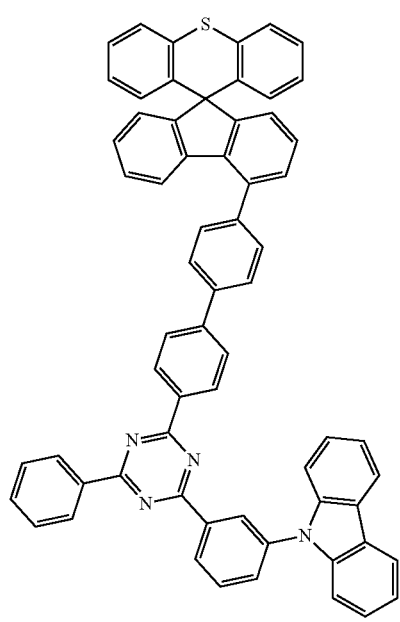
Formula 1-D-16
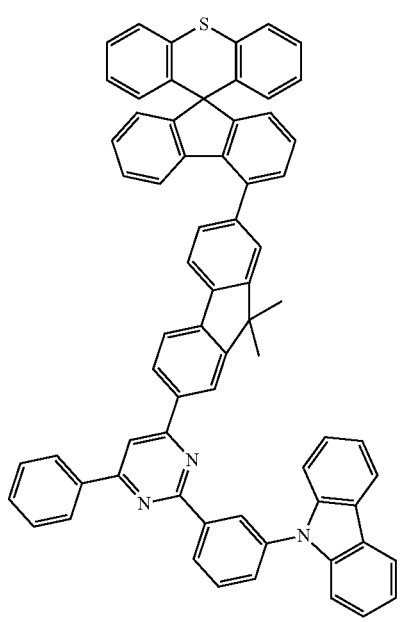
Formula 1-D-17
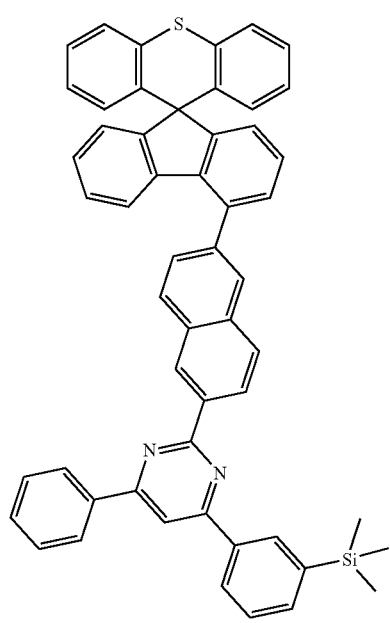
Formula 1-D-18
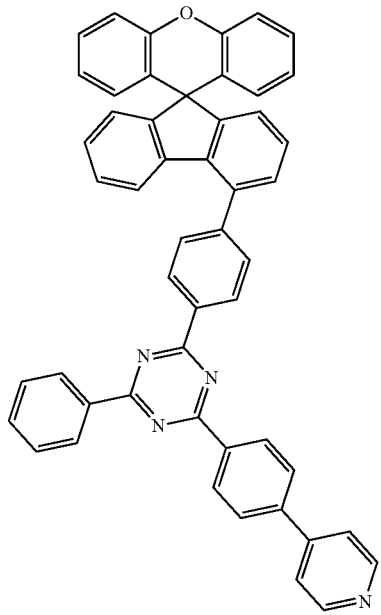

Formula 1-D-19
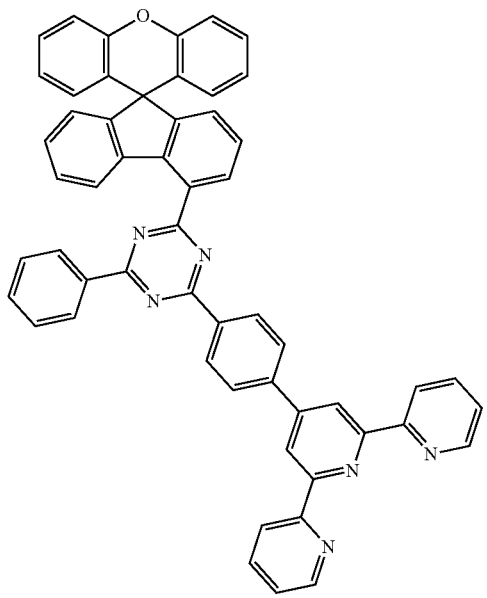
Formula 1-D-20
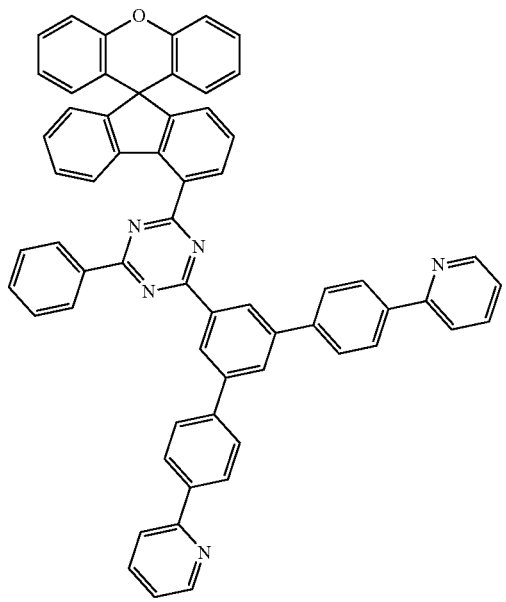
Formula 1-D-21
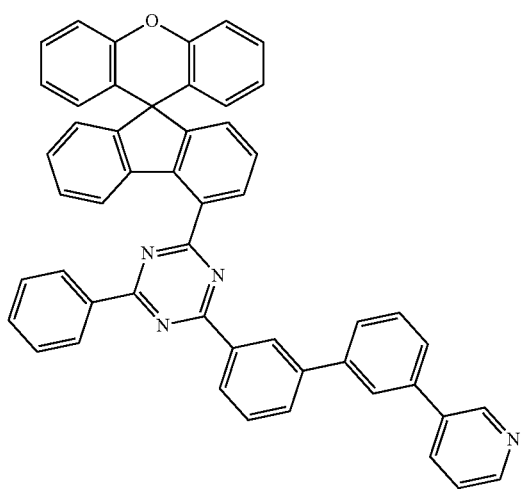
Formula 1-D-22
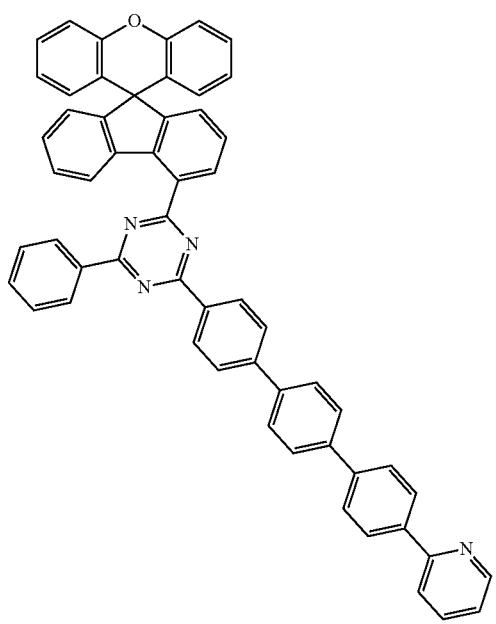

-continued
Formula 1-D-23
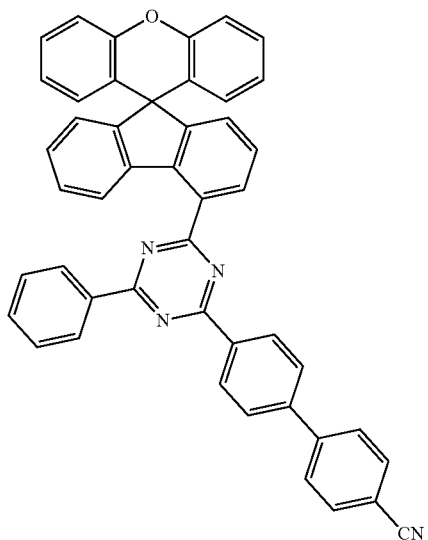
Formula 1-D-24
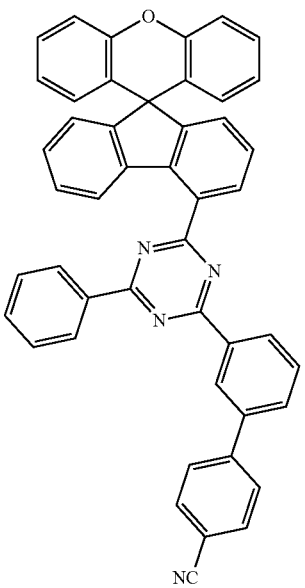
Formula 1-D-25
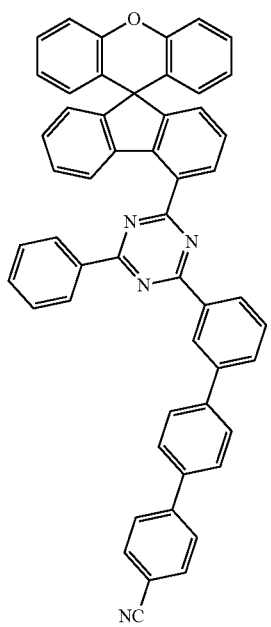
Formula 1-D-26
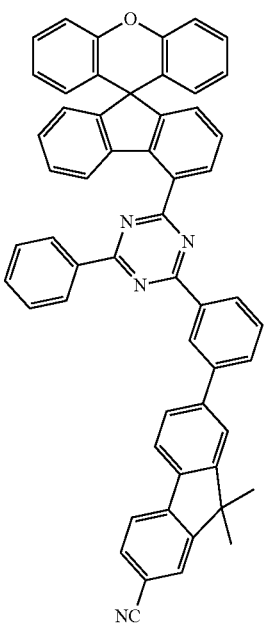
Formula 1-D-27
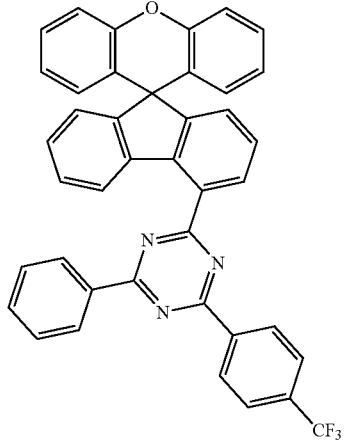
Formula 1-D-28
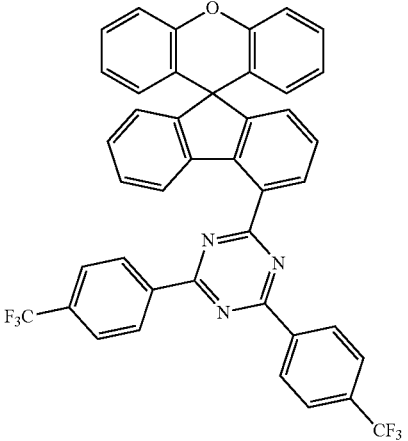

Formula 1-D-29

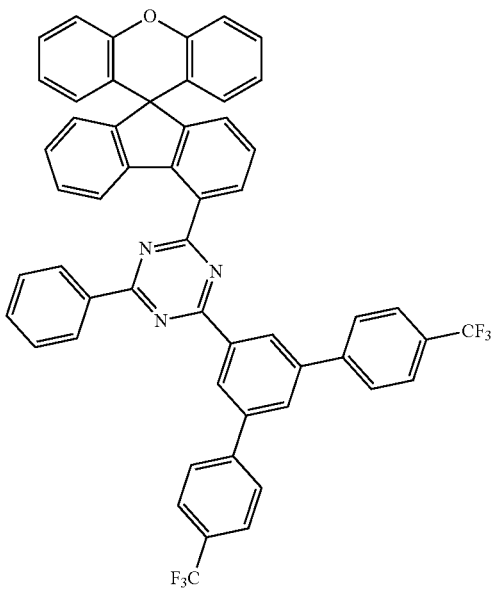

Formula 1-D-30

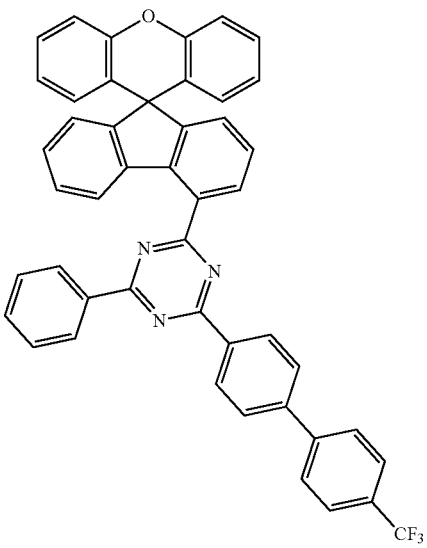

Formula 1-D-31

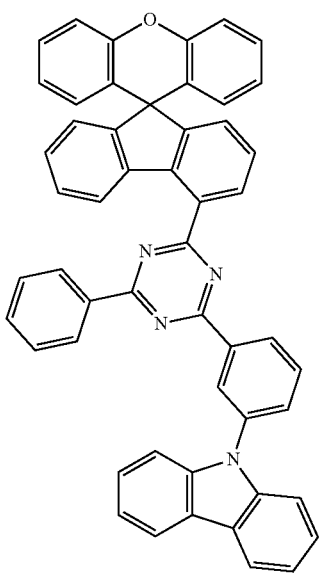

9. An organic light emitting device comprising a first electrode; a second electrode provided opposite to the first electrode; and one or more organic material layers provided between the first electrode and the second electrode, wherein one or more one layers of the organic material layers comprise the compound according to claim 1.

10. The organic light emitting device according to claim 9, wherein the organic material layer containing the compound is an electron injection layer, an electron transport layer, or a layer simultaneously performing electron injection and electron transport.

11. An organic light emitting device comprising a first electrode; a second electrode provided opposite to the first electrode; and one or more organic material layers provided between the first electrode and the second electrode, wherein one or more one layers of the organic material layers comprise the compound according to claim 2.

12. The organic light emitting device according to claim 11, wherein the organic material layer containing the compound is an electron injection layer, an electron transport layer, or a layer simultaneously performing electron injection and electron transport.

13. An organic light emitting device comprising a first electrode; a second electrode provided opposite to the first electrode; and one or more organic material layers provided between the first electrode and the second electrode, wherein one or more one layers of the organic material layers comprise the compound according to claim 3.

14. The organic light emitting device according to claim 13, wherein the organic material layer containing the compound is an electron injection layer, an electron transport layer, or a layer simultaneously performing electron injection and electron transport.

* * * * *